US008771670B2

(12) United States Patent
Harris et al.

(10) Patent No.: US 8,771,670 B2
(45) Date of Patent: *Jul. 8, 2014

(54) IDENTIFICATION OF PROTECTIVE ANTIGENIC DETERMINANTS OF PORCINE REPRODUCTIVE AND RESPIRATORY SYNDROME VIRUS AND USES THEREOF

(75) Inventors: Delbert Linn Harris, Ames, IA (US); Matthew M. Erdman, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 14 days.

This patent is subject to a terminal disclaimer.

(21) Appl. No.: 13/533,167

(22) Filed: Jun. 26, 2012

(65) Prior Publication Data
US 2013/0156800 A1 Jun. 20, 2013

Related U.S. Application Data

(60) Division of application No. 12/782,030, filed on May 18, 2010, now Pat. No. 8,241,847, which is a continuation of application No. 12/345,259, filed on Dec. 29, 2008, now Pat. No. 7,763,428, which is a division of application No. 11/564,717, filed on Nov. 29, 2006, now Pat. No. 7,622,254.

(60) Provisional application No. 60/740,519, filed on Nov. 29, 2005.

(51) Int. Cl.
*C12Q 1/68* (2006.01)
*A61K 38/00* (2006.01)

(52) U.S. Cl.
USPC ...................................... 424/93.2; 435/320.1

(58) Field of Classification Search
CPC ... A61K 39/12; A61K 39/295; A61K 39/135; A61K 39/145; C12N 2770/10022; C12N 2710/18022; C12N 2710/18034; C12N 2720/00022; C12N 2720/00034; C12N 2760/16122; C12N 2760/16134; C12N 2770/32122; C12N 2770/3213; C07K 14/005
See application file for complete search history.

(56) References Cited

U.S. PATENT DOCUMENTS

| | | | |
|---|---|---|---|
| 5,695,766 A | 12/1997 | Paul et al. | |
| 6,110,467 A | 8/2000 | Paul et al. | |
| 6,251,397 B1 | 6/2001 | Paul et al. | |
| 6,251,404 B1 | 6/2001 | Paul et al. | |
| 6,380,376 B1 | 4/2002 | Paul et al. | |
| 6,495,138 B1 | 12/2002 | Van Nieuwstadt et al. | |
| 6,592,873 B1 | 7/2003 | Paul et al. | |
| 6,773,908 B1 | 8/2004 | Paul et al. | |
| 6,977,078 B2 | 12/2005 | Paul et al. | |
| 7,122,347 B2 | 10/2006 | Verheije et al. | |
| 7,223,854 B2 | 5/2007 | Paul et al. | |
| 7,264,802 B2 | 9/2007 | Paul et al. | |
| 7,264,957 B2 | 9/2007 | Paul et al. | |
| 7,622,254 B2 * | 11/2009 | Harris et al. | 435/6.11 |
| 7,714,101 B2 * | 5/2010 | Harris et al. | 530/300 |
| 7,763,428 B2 * | 7/2010 | Harris et al. | 435/6.11 |
| 2008/0233083 A1 | 9/2008 | Ansari et al. | |

FOREIGN PATENT DOCUMENTS

WO WO 98/50426 11/1998
WO WO 2007/040876 A2 4/2007

OTHER PUBLICATIONS

Wissink et al., 2004. Significance of the oligosaccharides of the PRRSV virus glycoproteins GP2a and GP5 for infectious virus production. J. Gen. Virol. 85, 3715-3723.*
Ansari et al., 2006. Influence of N-linked glycosylation of PRRSV GP5 on virus infectivity, antigenicity, ability to induce neutralizing antibodies. J. Virol. 80 (8): 3994-4004.*
Ansari, Israrul H. et al., "Influence of N-linked Glycosylation of Porcine Reproductive and Respiratory Syndrome Virus GP5 on Virus Infectivity, Antigenicity, and Ability to Induce Neutralizing Antibodies", Journal of Virology, vol. 80, No. 8, Apr. 2006, pp. 3994-4004.
Balasuriya, Udeni B.R. et al., "Expression of the Two Major Envelope Proteins of Equine Arteritis Virus as a Heterodimer is Necessary for Induction of Neutralizing Antibodies in Mice Immunized with Recombinant Venezuelan Equine Encephalitis Virus Replicon Particles", Journal of Virology, Nov. 2000, vol. 74, No. 22, pp. 10623-10630.
Balasuriya, Udeni B.R. et al., "Alphavirus replicon particles expressing the two major envelope proteins of equine arteritis virus induce high level protection against challenge with virulent virus in vaccinated horses", Vaccine 20 (2002) pp. 1609-1617.
Balasuriya, Udeni B.R., et al., "The immune response to equine arteritis virus: potential lessons for other arteriviruses", Veterinary Immunology and Immunopathology 102 (2004) pp. 107-129.
Dacheux, Laurent et al., "Evolutionary Dynamics of the Glycan Shield of the Human Immunodeficiency Virus Envelope during Natural Infection and Implications for Exposure of the 2G12 Epitope", Journal of Virology, vol. 78, No. 22, Nov. 2004, pp. 12625-12637.
Delputte, P. L., et al., "Involvement of the Matrix Protein in Attachment of Porcine Reproductive and Respiratory Syndrome Virus to a Heparinlike Receptor on Porcine Alveolar Macrophages", Journal of Virology, vol. 76, No. 9 on May 2002, pp. 4312-4320.

(Continued)

*Primary Examiner* — Bao Li
(74) *Attorney, Agent, or Firm* — McKee, Voorhees & Sease, P.L.C.

(57) ABSTRACT

The invention relates to a polypeptide of a protective antigenic determinant (PAD polypeptide) of porcine reproductive and respiratory syndrome virus (PRRSV) and nucleic acids encoding a PAD polypeptide. The PAD polypeptide and nucleic acids encoding a PAD polypeptide are useful in the development of antibodies directed to PAD, vaccines effective in providing protection against PRRSV infection, and diagnostic assays detecting the presence of PAD antibodies generated by a PAD-specific vaccine. The invention also discloses methods of generating antibodies to PAD, for vaccinating a pig to provide protection from PRRSV infections, a method of preparing the vaccine, a method of treating PRRSV infections in a pig, and a method of detecting antibodies to PAD of PRRSV.

5 Claims, 25 Drawing Sheets

(56) References Cited

OTHER PUBLICATIONS

Delputte, Peter L., et al., "Porcine Arterivirus Infection of Alveolar Macrophages Is Mediated by Sialic Acid on the Virus", Journal of Virology, vol. 78, No. 15, Aug. 2004, pp. 8094-8101.

Delputte, P. L., et al., "Effect of virus-specific antibodies on attachment, internalization and infection of porcine reproductive and respiratory syndrome virus in primary macrophages", Veterinary Immunology and Immunopathology 102, (2004) pp. 179-188.

Faaberg, Kay S. et al., "Neutralizing Antibody Responses of Pigs Infected with Natural GP5 N-Glycan Mutants of Porcine Reproductive and Respiratory Syndrome Virus", Viral Immunology, vol. 19, No. 2, Jun. 2006, pp. 294-304.

Fang, Liurong et al., "Enhanced immunogenicity of the modified GP5 of porcine reproductive and respiratory syndrome virus", Virus Genes (2006) 32:5-11.

Forsberg, Roald et al., "The Genetic Diversity of European Type PRRSV is Similar to That of the North American Type but is Geographically Skewed within Europe." Virology 299, (2002), pp. 38-47.

Harris, D. L. et al., "Introducing PRRSV-Negative Replacement Breeding Stock Into Seropositive Herd", Schering-Plough Animal Health, SPAH-FOC-20, vol. 3, No. 7, (2000), 4 pages.

Jiang, Yun-Bo et al., "Expression of GP5-M fusion protein of porcine reproductive and respiratory syndrone virus (PRRSV) and establishment of ELISA diagnose based on the recombinant fusion protein", Chinese J. of Biotechnology, China, vol. 21(2):259-264 (Mar. 2005). (Chinese).

Jiang, Yun-Bo et al., "Expression of GP5-M fusion protein of porcine reproductive and respiratory syndrome virus (PRRSV) and establishment of ELISA diagnose based on the recombinant fusion protein", Chinese J. of Biotechnology, China, vol. 21(2):259-264 (Mar. 2005). (English translation of the above NPL Citation No. 9).

Database Medline, US National Library of Medicine, Mar. 2005, XP-002436518, (English Abstract) of Jiang,Yun-Bo et al., "Expression of GP5-M fusion protein of porcine reproductive and respiratory syndrome virus (PRRSV) and establishment of ELISA diagnose based on the recombinant fusion protein", 1 page.

Jiang, Wenming et al., "Recombinant adenovirus expressing GP5 and M fusion proteins of porcine reproductive and respiratory syndrome virus induce both humoral and cell-mediated immune responses in mice", Veterinary Immunology and Immunopathology 113 (2006), pp. 169-180.

Jiang, Yunbo et al., "DNA vaccines co-expression GP5 and M proteins of porcine reproductive and respiratory syndrome virus (PRRSV) display enhanced immunogenicity", Vaccine, Butterworth Scientific, Guildford, GB, vol. 24, No. 15, Apr. 5, 2006, pp. 2869-2879.

Jiang, Yunbo et al., "Immunogenicity and protective efficacy of recombinant pseudorabies virus expressing the two major membrane-associated proteins of porcine reproductive and respiratory syndrome virus", Vaccine, 25:547-560 (2007).

Jusa, Enuh R. et al., "Effect of heparin on infection of cells by porcine reproductive and respiratory syndrome virus", AJVR, vol. 58, No. 5, May 1997, pp. 488-491.

Lopez, O. J., et al., "Role of neutralizing antibodies in PRRSV protective immunity", Veterinary Immunology and Immunopathology 102 (2004), pp. 155-163.

Mardassi et al., Virology 221 (1996), pp. 98-122.

Mateu, Enric et al., "Genetic diversity and phylogenetic analysis of glycoprotein 5 of European-type porcine reproductive and respiratory virus strains in Spain", Journal of General Virology (2003), 84, pp. 529-534.

Murtaugh, Michael P., "Immunity and diagnosis of PRRS in homologous and heterologous infection", 36th American Association Swine Veterinarians Annual Meeting (Toronto, Ontario), Seminar #2 "Applying PRRS Diagnostic Tools", Mar. 5, 2005, pp. 1-5.

Osorio, F. A., et al., "Passive Transfer of Virus-Specific Antibodies Confers Protection against Reproductive Failure Induced by a Virulent Strain of Porcine Reproductive and Respiratory Syndrome Virus and Establishes Sterilizing Immunity", Virology 302, (2002), pp. 9-20.

Ostrowski, M., et al., "Identification of Neutralizing and Nonneutralizing Epitopes in the Porcine Reproductive and Respiratory Syndrome Virus GP5 Ectodomain", Journal of Virology, vol. 76, No. 9, May 2002, pp. 4241-4250.

Plagemann, Peter G. W., "Porcine Reproductive and Respiratory Syndrome Virus: Origin Hypothesis", Emerging Infectious Diseases, vol. 9, No. 8, Aug. 2003, pp. 903-908.

Plagemann et al., Archive. Virology, vol. 147, 2002, pp. 2327-2347.

Reitter, Julie N. et al., "A role for carbohydrates in immune evasion in AIDS", Nature Medicine, vol. 4, No. 6, Jun. 1998, pp. 679-684.

Ropp, Susan L. et al., "Characterization of Emerging European-Like Porcine Reproductive and Respiratory Syndrome Virus Isolates in the United States", Journal of Virology, vol. 78, No. 7, Apr. 2004, pp. 3684-3703.

Snijder, Eric J. et al., "Heterodimerization of the Two Major Envelope Proteins is Essential for Arterivirus Infectivity", Journal of Virology, vol. 77, No. 1, Jan. 2003, pp. 97-104.

Snijder, Eric J. et al., "The Molecular biology of arteriviruses" Journal of General Virology, vol. 79, (1998), pp. 961-979.

Wei, Xiping et al., "Antibody neutralization and escape by HIV-1" Nature 422, (Mar. 20, 2003), pp. 307-312. (www.nature.com, Oct. 8, 2004, 8 pages).

Wissink, E.H.J. et al., "Significance of the oligosaccharides of the porcine reproductive and respiratory syndrome virus glycoproteins GP2a and GP5 for infectious virus production", Journal of General Virology, Dec. 2004, vol. 85, No. Pt. 12, pp. 3715-3723.

Yoo, Dongwan et al., "Infectious cDNA clones of porcine reproductive and respiratory syndrome virus and their potential as vaccine vectors", Veterinary Immunology and Immunopathology 102 (2004), pp. 143-154.

Zitzmann, Nicole et al., "Glycobiology against viruses", The Biochemist, Jun. 2006, pp. 23-26.

Zolla-Pazner, Susan, "Identifying epitopes of HIV-1 that induce protective antibodies", Nature Reviews/ Immunology, vol. 4, Mar. 2004, pp. 199-210.

International Search Report, Iowa State Research Foundation, Inc., PCT/US2006/045758, filed Nov. 29, 2006.

\* cited by examiner

| | | | | | | | |
|---|---|---|---|---|---|---|---|
| (HLV013) | MLGRCLTAGC | CSQLPFLWCI | VPFCLVALVN | ANSNSGSHLQ | LIYNLTLCEL | NGTDWLKDKF | SEQ ID NO:1 |
| (HLV093 | MLGRCLTACY | CLRLLSLWCI | VPFWFAVLVS | ANSNSSSHLQ | SIYKLTLCEL | NGTEWLNERF | SEQ ID NO:2 |
| (HLV094) | MLGRCLTAGY | CSQLPSLWCI | VPFWFAVLVS | ANSTSSSYSQ | LIYNLTICEL | NGPDWLNEKF | SEQ ID NO:3 |
| (Lelystad) | MRCSHKLGRF | LTPHSCFWWL | FLLCTGLSWS | FADGNGDSST | YQYIYNLTIC | ELNGTDWLSS | SEQ ID NO:4 |
| (HLV092) | MLGKCLTAGY | CSQLPFLWCI | VPFCLAALVN | ANSNSSSHLQ | LIYNLTICEL | NGTDWLNNHF | SEQ ID NO:5 |
| (VR2332) | MLEKCLTAGC | CSRLLSLWCI | VPFCFAVLAN | ASNDSSSHLQ | LIYNLTLCEL | NGTDWLANKF | SEQ ID NO:6 |
| (ResPRRS) | MLEKCLTAGC | CSQLLSLWCI | VPFCFAVLAN | ASNDSSSHLQ | LIYNLTLCEL | NGTDWLANKF | SEQ ID NO:7 |
| (IA 97-7895) | MLGRCLTAGC | CSRLLSLWCI | VPFCFAALVN | ANSNSSSHLQ | LIYNLTLCEL | NGTDWLKDKF | SEQ ID NO:8 |
| (Prime Pac) | MLGKCLTAGC | CSRLLSFWCI | VPFCFAVLVN | ASYSSSSHLQ | LIYNLTLCEL | NGTDWLANKF | SEQ ID NO:9 |
| (ISU-P) | MLGKCLTAGC | CSRLPSLWCI | VPFCFAVLAS | ASSDSSSHLQ | LIYNLTLCEL | NGTDWLANKF | SEQ ID NO:10 |
| (VR2385) | MLGKCLTAGC | CSQLLFLWCI | VPSCFVALVS | ANGNSGSNLQ | LIYNLTLCEL | NGTDWLANKF | SEQ ID NO:11 |

FIG. 9

Matrix     GP 5

Glycan —

Neutralizing Epitope ▬

FIG. 16

Matrix    GP 5

Glycan —

Neutralizing Epitope ▬

FIG. 17

Matrix    GP 5

Glycan —

Neutralizing Epitope ▬

FIG. 18

Matrix    GP 5

Glycan —

Neutralizing Epitope ▬

FIG. 19

ORF5
ATGTTGGGGAGATGCTTGACCGCGGGCTGTTGCTCGCGATTGCTTTCTTTGTGGTGTATCGTGCCATT
TTGTTTTGTTGCGCTCGTCAACGCCAACAGCAACAGCGGCTCTCATCTTCAGTTAATTTACAACTTGA
CGCTATGTGAGCTGAATGGCACAGATTGGCTGAAAGACAAATTTGATTGGGCAGTGGAGACTTTTGT
CATCTTTCCCGTGTTGACTCACATTGTCTCATATAGTGCACTCACCACTAGCCATTTCCTTGACACAG
CCGGTCTGGTTACTGTGTCTACTGCCGGGTTCTACCACGGGCGGTATGTTCTGAGTAGCATCTACGC
GGTCTGCGCTCTGGCCGCATTGACTTGCTTCGTCATTAGGCTTGCGAAGAACTGCATGTCCTGGCGCT
ACTCTTGTACCAGATATACTAACTTCCTTCTGGACACTAAGGGCAGACTCTATCGCTGGCGGTCGCC
CGTTATCATAGAGAAAGGGGGTAAGGTTGAGGTCGAAGGTCACCTGATCGACCTCAAAAGAGTTGT
GCTTGATGGTTCCGTGGCAACCCCTTTAACCAGAGTTTCAGCGGAACAATGGGGTCGTCTTTAG
SEQ ID NO:25

GP5
MLGRCLTAGC CSRLLSLWCI VPFCFVALVN ANSNSGSHLQ LIYNLTLCEL NGTDWLKDKF
DWAVETFVIF PVLTHIVSYS ALTTSHFLDT AGLVTVSTAG FYHGRYVLSS IYAVCALAAL
TCFVIRLAKN CMSWRYSCTR YTNFLLDTKG RLYRWRSPVI IEKGGKVEVE GHLIDLKRVV
LDGSVATPLT RVSAEQWGRL SEQ ID NO:26

ORF6
ATGGGGTCGTCTTTAGACGACTTTTGCTATGATAGCACGGCTCCACAAAAGGTGCTTTTGGCGTTTTC
CATTACCTACACGCCAGTGATGATATATGCTCTAAAGGTAAGTCGCGGCCGACTTTTAGGGCTTCTG
CACCTTTTGATCTTTCTGAATTGTGCTTTTACCTTCGGGTACATGACATTCGTGCACTTTAATAGCAC
AAATAAGGTCGCGCTCACTATGGGAGCAGTAGTTGCACTTCTTTGGGGGGTGTACTCAGCCATAGAA
ACCTGGAAGTTCATCACCTCCAGATGTCGTTTGTGCTTGCTAGGCCGCAAGTACATTCTGGCCCCCG
CCCACCACGTCGAAAGTGCCGCGGGCTTTCATCCGATCGCGGCAAATGATAACCACGCATTTGTCGT
CCGGCGTCCCGGCTCCACTACGGTTAACGGCACATTGGTGCCCGGGTTGAAAAGCCTCGTGTTGGGT
GGCAGAAAAGCTGTTAAACAGGGAGTGGTAAACCTTGTCAAATATGCCAAATAA SEQ ID NO:27

Matrix
MGSSLDDFCY DSTAPQKVLL AFSITYTPVM IYALKVSRGR LLGLLHLLIF LNCAFTFGYM
TFVHFNSTNK VALTMGAVVA LLWGVYSAIE TWKFITSRCR LCLLGRKYIL APHHVESAA
GFHPIAANDN HAFVVRRPGS TTVNGTLVPG LKSLVLGGRK AVKQGVVNLV KYAK SEQ ID NO:28

FIG. 20

Vr2332
MGSSLDDFCHDSTAPQKVLLAFSITYTPVMIYALKVSRGRLLGLLHLLIFLNCAFTFGYMTFAHFQSTNKVALTMG
AVVALLWGVYSAIETWKFITSRCRLCLLGRKYILAPAHHVESAARFHPIAANDNHAFVVRRPGSTTVNGTLVPGLK
SLVLGGRKAVKQGVVNLVKYAK   SEQ ID NO:29

ResPRRS
MGSSLDDFCHDSTAPEKVLLAFSITYTPVMIYALKVSRGRLLGLLHLLIFLNCAFTFGYMTFAHFQSTNKVALTMG
AVVALLWGVYSAIETWKFITSRCRLCLLGRKYILAPAHHVESAAGFHPIAANDNHAFVVRRPGSTTVNGTLVPGLK
SLVLGGRKAVKQGVVNLVKYAK   SEQ ID NO:30

Olot/91
MGSLDDFCNDSTAAQKLVLAFSITYTPIMIYALKVSRGRLLGLLHILIFLNCSFTFGYMTYVHFQSTNRVALTLGA
VVALLWGVYSFTESWKFVTSRCRLCLGRRYILAPAHHVESAAGLHSIPASGNRAYAVRKPGLTSVNGTLVPGLRSL
VLGGKRAVKRGVVNLVKYGR   SEQ ID NO:31

FJ-1
MGSSLDDFCHDSTAPQKVLLAFSITYTPVMIYALKVSRGRLLGLLHLLIFLNCAFTFGYMTFTHFQSTNKVALTMG
AVVALLWGVYSAIESWRFITSRCRLCLLGRKYILAPAHHVESAAGFHPIAANDNHAFVVRRPGSTTVNGTLVPGLK
SLVLGGKKAVKQGVVNLVKYAK   SEQ ID NO:32

JA 142
MGSSLDDFCYDSTAPQKVLLAFSITYTPVMIYALKVSRGRLLGLLHLLIFLNCTFTFGYMTFVHFNSTNKVALTMG
AVVALLWGVYSAIETWKFITSRCRLCLLGRKYILAPAHHVESAAGFHPIAANDNHAFVVRRPGSTTVNGTLVPGLK
SLVLGGRKAVKQGVVNLVKYAK   SEQ ID NO:33

NVSL-14
MGSSLDDFCHDSTAPQKVLLAFSITYTPVMIYALKVSRGRLLGLLHLLIFLNCAFTFGYMTFVHFQSTNRVALTMG
AVVALLWGVYSAIETWKFITSRCRLCLLGRKYILAPAHHVESAAGFHPITANDNHAFVVRRPGSTTVNGTLVPGLK
SLVLGGRKAVKQGVVNLVKYAK   SEQ ID NO:34

NADC-9
MGSSLDDFCHDSTAPQKVLLAFSITYTPVMIYALKVSRGRLLGLLHLLIFLNCVFTFGYMTFVHFQSTNKVALTMG
AVVALLWGVYSAIETWKFITSRCRLCLLGRKYILAPAHHVESAAGFHPIAANDNHAFVVRRPGSTTVNGTLVPGLK
SLVLGGRKAVKQGVVNLVKYAK   SEQ ID NO:35

NADC-8
MGSSLDDFCHDSTAPQKVLLAFSITYTPVMIYALKVSRGRLLGLLHLLIFLNCAFTFGYMTFVHFQSTNKVALTMG
AVVALLWGVYSAIETWKFITSRCRLCLLGRKYILAPAHHVESAAGFHPIAANDNHAFVVRRPGSTTVNGTLVPGLK
SLVLGGRKAVKQGVVNLVKYAK   SEQ ID NO:36

PL97-1 Korea
MGSSLDDFCHDSTAPQKVLLAFSITYTPVMIYALKVSRGRLLGLLHLLIFLNCAFTFGYMTFAHFQSTNKVALTMG
AVVALLWGVYSAIETWKFITSRCRLCLLGRKYILAPAHHVESAAGFHPIAANDNHAFVVRRPGSTTVNGTLVPGLK
SLVLGGRKAVKQGVVNLVKYAK   SEQ ID NO:37

NVSL-97-7895
MGSSLDDFCYDSTAPQKVLLAFSITYTPVMIYALKVSRGRLLGLLHLLIFLNCTFTFGYMTFVHFNSTNKVALTMG
AVVALLWGVYSAIETWKFITSRCRLCLLGRKYILAPAHHVESAAGFHPIAANDNHAFVVRRPGSTTVNGTLVPGLK
SLVLGGRKAVKQGVVNLVKYAK   SEQ ID NO:38

EuroPRRSV
MGGLDDFCNDPTAAQKLVLAFSITYTPIMIYALKVSRGRLLGLLHILIFLNCSFTFGYMTYVHFQSANRVALTLGA
VVALLWGVYSLTESWKFITSRCRLCCLGRRYILAPAHHVESAAGLHSISASGNRAYAVRKPGLTSVNGTLVPGLRS
LVLGGKRAVKRGVVNLVKYGR   SEQ ID NO:39

FIG. 21A

```
BJ 4
MGSSLDDFCHDSTAPEKVLLAFSITYTPVMIYALKVSRGRLLGLLHLLIFLNCAFTFGYMTFAHFQSTNKVALTMG
AVVALLWGVYSAIETWKFITSRCRLCLLGRKYILAPAHHVESAAGFHPIAANDNHAFVVRRPGSTTVNGTLVPGLK
SLVLGGRKAVKQGVVNLVKYAK    SEQ ID NO:40

Lelystad
MGGLDDFCNDPIAAQKLVLAFSITYTPIMIYALKVSRGRLLGLLHILIFLNCSFTFGYMTYVHFQSTNRVALTL

FIG. 22A

```
(42628 JL)         MLGKCLTAGC CSRLLSLWCI VPSWFAVLVN ANSASSSHLQ LIYNLTICEL NGTDWLADKF DWAVETFVLY PVLEHIVSYG ALTTSHFLDT VGHVTVSTAG
(HLV093)           MLGRCLTACY CLRLLSLWCI VFFWFAVLVS ANSMSSSHLQ STYKLTLCEL NGTEWLMNEKF
(HLV094)           MLGRCLTAGY CSQLPSLWCI VFFWFAVLVS ANSTSSSY

ORF5 of HLV092

ATGTTGGGGAAATGCTTGACCGCGGGCTATTGCTCGCAATTGCCTTTTTTGTG
GTGTATCGTGCCGTTCTGTCTTGCTGCGCTCGTCAACGCCAGCAGCAACAGCA
GCTCCCACTTACAGTTGATTTATAACTTAACGATATGTGAGCTGAATGGCACA
GACTGGCTGAATGATCATTTTAGTTGGGCAGTGGAGACTTTCGTTATCTTTCCT
GTGTTGACTCACATTGTTTCCTACGGCGCCCTCACTACCAGCCACTTCCTTGAC
ACGGTCGGCCTGATCACTGTGTCCACCGCCGGATACTACCATGCGCGGTATGT
CTTGAGTAGCATCTATGCCGTCTGCGCCCTGGCTGCGCTGATTTGCTTCGTCAT
CAGGTTGACGAAAAATTGTATGTCCTGGCGCTACTCATGTACCAGATATACCA
ACTTTCTTCTGGACACCAAGGGCAGACTCTATCGCTGGCGGTCACCCGTCATC
ATAGAGAAAAGGGGTAAAATTGAGGTTGGAGGTGACCTGATCGACCTCAAGA
GAGTTGTGCTTGATGGCTCCGCGGCAACCCCTGTAACCAAAGTTTCAGCGGAA
CAATGGGGTCGTCCTTAG SEQ ID NO:88

GP5 of HLV092

MLGKCLTAGYCSQLPFLWCIVPFCLAALVNASSNSSSHLQLIYNLTICELNGTDWL
NDHFSWAVETFVIFPVLTHIVSYGALTTSHFLDTVGLITVSTAGYYHARYVLSSIY
AVCALAALICFVIRLTKNCMSWRYSCTRYTNFLLDTKGRLYRWRSPVI
IEKRGKIEVGGDLIDLKRVVLDGSAATPVTKVSAEQWGRP SEQ ID NO:89

FIG. 23

ORF 5 of HLV093

ATGTTGGGGAAATGCTTGACCGCGGGCTATTGCTCGCAATTGCCTTTTTTGTG
GTGTATCGTGCCGTTCTGTCTTGCTGCGCTCGTCAACGCCAACAACGACAGCA
GCTCCCACTTACAGTTGATTTATAGCTTAACGATATGTGAGCTGAATGGCACA
GAATGGCTGAACGAACATTTCAGTTGGGCAGTGGAGACCTTCGTCATCTTTCC
TGCGTTGACTCATATTGTTTCCTACGGCGCCCTCACTACCAGCCACTTCCTTGA
CACGGTCGGCCTGATCACTGTGTCCACCGCCGGATACTACCATAAGCGGTATG
TCTTGAGTAGCATCTATGCTGTCTGCGCCCTGGCTGCGCTGATTTGCTTCGTCA
TCAGGTTGACGAAAAATTGTATGTCCTGGCGCTACTCATGTACCAGATATACC
AACTTTCTTCTGGACACCAAGGGCAGACTCTATCGCTGGCGGTCACCCGTCAT
CATAGAGAAAAAGGGTAAGATTGAGGTTGGAGGTGACCTAATCGACCTCAAG
AGAGTTGTGCTTGATGGTTCCGCGGCAACCCCTGTAACCAAAGTTTCAGCGGA
ACAATGGGGTCGTCCTTAG  SEQ ID NO:90

GP5 of HLV093

MLGKCLTAGYCSQLPFLWCIVPFCLAALVNANNDSSSHLQLIYSLTICELNGTEW
LNEHFSWAVETFVIFPALTHIVSYGALTTSHFLDTVGLITVSTAGYYHKRYVLSSIY
AVCALAALICFVIRLTKNCMSWRYSCTRYTNFLLDTKGRLYRWRSPVIIEKKGKIE
VGGDLIDLKRVVLDGSAATPVTKVSAEQWGRP  SEQ ID NO:91

FIG. 24

IDENTIFICATION OF PROTECTIVE ANTIGENIC DETERMINANTS OF PORCINE REPRODUCTIVE AND RESPIRATORY SYNDROME VIRUS AND USES THEREOF

CROSS-REFERENCE TO RELATED APPLICATIONS

This is a Divisional of U.S. application Ser. No. 12/782,030 filed May 18, 2010, which is a Continuation of U.S. Ser. No. 12/345,259 filed Dec. 29, 2008, now U.S. Pat. No. 7,763,428 issued on Jul. 27, 2010, which is a Divisional of U.S. application Ser. No. 11/564,717 filed Nov. 29, 2006, now U.S. Pat. No. 7,622,254, issued on Nov. 24, 2009, which claims priority under 35 U.S.C. §119 of Provisional Application Ser. No. 60/740,519 filed Nov. 29, 2005, and which applications are hereby incorporated by reference in their entirety.

GRANT REFERENCE

This invention was made with government support under Grant No. 2004-35605-14197 awarded by USDA/CREES. The United States government has certain rights in the invention.

FIELD OF THE INVENTION

Embodiments of the invention relate generally to the field of porcine reproductive and respiratory syndrome virus (PRRSV) and more particularly to the discovery of a novel protective antigenic determinant (PAD) of PRRSV and its use in vaccines, treatments, and diagnostic assays.

BACKGROUND OF THE INVENTION

In 1987, the swine-producing industry in the United States experienced an unknown infectious disease which had a serious economic impact on the swine industry. The disease syndrome was reported in Europe including Germany, Belgium, the Netherlands, Spain and England.

The disease is characterized by reproductive failure, respiratory disease and various clinical signs including loss of appetite, fever, dyspnea, and mild neurologic signs. A major component of the syndrome is reproductive failure which manifests itself as premature births, late term abortions, pigs born weak, stillbirths, mummified fetuses, decreased farrowing rates, and delayed return of estrus. Clinical signs of respiratory disease are most pronounced in pigs under 3-weeks-of-age but are reported to occur in pigs at all stages of production. Affected piglets grow slowly, have roughened hair coats, respiratory distress ("thumping"), and increased mortality.

The disease syndrome has been referred to by many different terms including mystery swine disease (MSD), porcine epidemic abortion and respiratory syndrome (PEARS), swine infertility and respiratory syndrome (SIRS). The name now commonly used is porcine reproductive and respiratory syndrome (PRRS); this term will be employed throughout this patent application.

PRRSV preferentially grows in alveolar lung macrophages (Wensvoort et al., 1991). A few cell lines, such as CL2621 and other cell lines cloned from the monkey kidney cell line MA-104 are also susceptible to the virus. Some well known PRRSV strains are known under accession numbers CNCM I-1102, I-1140, I-1387, I-1388, ECACC V93070108, or ATCC VR 2332, VR 2385, VR 2386, VR 2429, VR 2474, and VR 2402. The genome of PRRSV is 15 kb in length and contains genes encoding the RNA dependent RNA polymerase (ORF1a and ORF1b) and genes encoding structural proteins (ORFs 2 to 7; Meulenberg et al., 1993 and Meulenberg et al., 1996). ORF5 encodes the major envelope glycoprotein, designated GP5. The ORFs 2, 3, and 4 encode glycoproteins designated GP2, GP3, and GP4, respectively. These glycoproteins are less abundantly present in purified virions of the Lelystad virus isolate of PRRSV. The GP5 protein is approximately 200 amino acids in length and is 25 kDa in molecular weight and forms a di-sulfide-linked heterodimer with the matrix protein M encoded by ORF6 in the ER. The M protein is approximately 190 amino acids in length, is 19 kDa and is non-glycosylated. The nucleocapsid protein N is encoded by ORF7. The analysis of the genome sequence of PRRSV isolates from Europe and North America, and their reactivity with monoclonal antibodies has proven that they represent two different antigenic types. The isolates from these continents are genetically distinct and must have diverged from a common ancestor relatively long ago (Murtaugh et al., 1995).

The genomic organization of arteriviruses resembles coronaviruses and toroviruses in that their replication involves the formation of a 3'-coterminal nested set of subgenomic mRNAs (sg mRNAs) (Chen et al., 1993, J. Gen. Virol. 74:643-660; Den Boon et al., 1990, J. Virol., 65:2910-2920; De Vries et al., 1990, Nucleic Acids Res., 18:3241-3247; Kuo et al., 1991, J. Virol., 65:5118-5123; Kuo et al., 1992; U.S. application Ser. Nos. 08/131,625 and 08/301,435). Partial sequences of several North American isolates have also been determined (U.S. application Ser. Nos. 08/131,625 and 08/301,435; Mardassi et al., 1994, J. Gen. Virol., 75:681-685). Currently available vaccines either do not induce viral neutralizing VN antibodies or induce them at inadequate levels needed for protection against PRRSV infection. There are currently no commercially available products containing antibodies for the prevention of PRRSV infection or treatment of PRRS. Currently available commercial vaccines do not provide adequate protection against PRRS. Conservative estimates indicate that PRRS is costing the US industry $600 million per year.

For these and other reasons, there is a need for the present invention.

BRIEF SUMMARY OF THE INVENTION

The present inventors are the first to recognize a protective antigenic determinant (PAD) for porcine reproductive and respiratory syndrome virus (PRRSV) that provides treatment for and protection against PRRSV infection. Surprisingly, the present inventors have identified that glycoprotein 5 (GP5), matrix (M) protein, or a heterodimer of the GP5 and M protein of PRRSV linked by a disulfide bond gives rise to a PAD that provides protection against PRRSV infections. The disulfide bond connecting the M protein with the GP5 protein results from a cysteine amino acid of the M protein at position 9 in North American and at position 8 EU PRRSV strains and a cysteine amino acid of the GP5 protein located at position 48 of North American PRRSV strains and position 50 of European PRRSV strains.

In one embodiment, the invention provides one or more isolated polypeptides comprising an antigenic sequence comprising glycoprotein 5 (GP5) of porcine reproductive and respiratory syndrome virus (PRRSV), wherein the GP5 protein has varying N-glycosylation patterns of asparagine amino acids located at positions 1-44 of the GP5 protein in North American PRRSV strains or at positions 1-46 of the GP5 protein in European PRRSV strains. In yet another embodiment, the invention provides an isolated polypeptide comprising an antigenic sequence comprising matrix (M) protein of porcine reproductive and respiratory syndrome virus (PRRSV). In another embodiment, the antigenic sequence includes the GP5 sequence as described above and a matrix protein (M protein) of PRRSV, wherein the GP5 protein is linked to said M protein by a disulfide bond, resulting from a cysteine amino acid of the M protein at position 9 in North American and at position 8 in EU PRRSV strains and a cysteine amino acid located at position 48 of the GP5 protein in North American PRRSV strains or from a cysteine amino acid located at position 50 in European PRRSV strains so that a GP5-M heterodimer is produced. In one aspect of the invention, the PAD includes a GP5-M heterodimer comprising the ectodomain of GP5 and the ectodomain of M.

In yet another embodiment, the invention provides an isolated nucleic acid encoding any of the PAD polypeptides of the present invention. Consequently, the invention provides for methods for generating antibodies against one or more protective antigenic determinant (PAD) of PRRSV, for preparing a vaccine against at least one PAD of PRRSV, of vaccinating pigs, for preventing or treating a PRRSV infection in a pig, and for detecting antibodies against at least one protective antigenic determinant (PAD) of PRRSV in an animal.

The present inventors contemplate a method for generating antibodies against at least one protective antigenic determinant (PAD) of PRRSV comprising providing at least one PAD polypeptide or nucleic acid encoding a PAD polypeptide and administering the peptide or nucleic acid to an animal subject. Also disclosed herein is a method for generating antibodies against at least one protective antigenic determinant (PAD) of PRRSV comprising: providing a PAD polypeptide or a nucleic acid encoding a PAD polypeptide and administering the peptide or nucleic acid to an animal subject. The invention also provides a method for preparing a vaccine against at least one PAD of PRRSV including a PAD polypeptide or a nucleic acid encoding a PAD polypeptide. In another embodiment, a method of vaccinating pigs includes administering to a pig, the vaccine that includes at least one PAD polypeptide or a nucleic acid encoding a PAD polypeptide in an amount effective for protecting against PRRSV infection when administered to a susceptible pig. The present inventors contemplate a method for preventing or treating a PRRSV infection in a pig comprising administering to a pig a therapeutically effective amount of a vaccine that has at least one PAD polypeptide or a nucleic acid encoding at least one PAD polypeptide. Yet another method for treating PRRSV infections in a pig comprises administering an antibody against at least one protective antigenic determinant (PAD) of PRRSV to an animal in need of treatment. Also contemplated is a method for detecting antibodies against at least one protective antigenic determinant (PAD) of PRRSV in an animal. This method includes incubating a biological sample, including antiserum, from an animal, for example, a pig, with a PAD polypeptide for a time sufficient for antibody binding to take place, and determining the binding of the antibody to the polypeptide.

In another embodiment, the invention provides an isolated antibody directed against at least one PAD polypeptide or a nucleic acid encoding a PAD polypeptide. The invention also discloses a vaccine for protecting against PRRSV infection comprising administering at least one PAD polypeptide or a nucleic acid encoding at least one PAD polypeptide in an amount effective for protecting against PRRSV infection. In another aspect, the vaccine also includes a physiologically acceptable carrier. In yet another embodiment, the invention provides for a kit that comprises at least one of the following: a PAD polypeptide, a nucleic acid encoding a PAD polypeptide, an antibody directed against a PAD polypeptide, or a vaccine including a PAD polypeptide or a nucleic acid encoding a PAD polypeptide.

Accordingly, an object of the present invention is to provide an isolated polypeptide comprising a PAD of PRRSV that includes the GP5 of PRRSV.

An object of the present invention is to provide an isolated polypeptide comprising a PAD of PRRSV that includes the matrix protein (M) of PRRSV.

A further still object of the present invention is to provide an isolated polypeptide comprising a PAD of PRRSV that includes the GP5 of PRRSV linked by a disulfide bond to the M protein of PRRSV.

Yet another object of the present invention is to provide an isolated nucleic acid encoding a PAD polypeptide.

Still another object of the present invention is to provide a method for generating antibodies against a protective antigenic determinant (PAD) of PRRSV.

A further object of the present invention is to provide a method for preparing a vaccine.

Another object of the present invention to provide a method of vaccinating pigs against PAD of PRRSV effective for protecting pigs against PRRSV infections.

It is an object of the present invention to provide a vaccine against PAD of PRRSV capable of protecting pigs against PRRSV infections.

It is a further object of the present invention to provide a method of treating or preventing a PRRSV infection in a pig.

Still another object of the present invention is to provide a method for detecting antibodies against a protective antigenic determinant (PAD) of PRRSV in an animal.

It is a further object of the present invention to provide an antibody that immunologically binds to a PAD polypeptide of PRRSV.

Yet another object of the present invention is to provide a vaccine effective for protecting against PRRSV infection.

It is a further object of the present invention to provide a diagnostic kit for assaying or detecting antibodies to PAD of PRRSV.

These and other embodiments of the invention will become apparent upon reference to the following Detailed Description. All references disclosed herein are hereby incorporated by reference in their entireties as if each was incorporated individually.

BRIEF DESCRIPTION OF THE DRAWINGS

FIG. 1: Amino acid comparison of PRRSV GP5 signal sequence and ectodomain (amino acids 1-60). The neutralizing epitope of GP5 is underlined. N-glycosylation sites are in bold. Presence or location of N-glycans in the ectodomain may be related to susceptibility to or development of PRRSV neutralizing antibodies.

Figure 9:
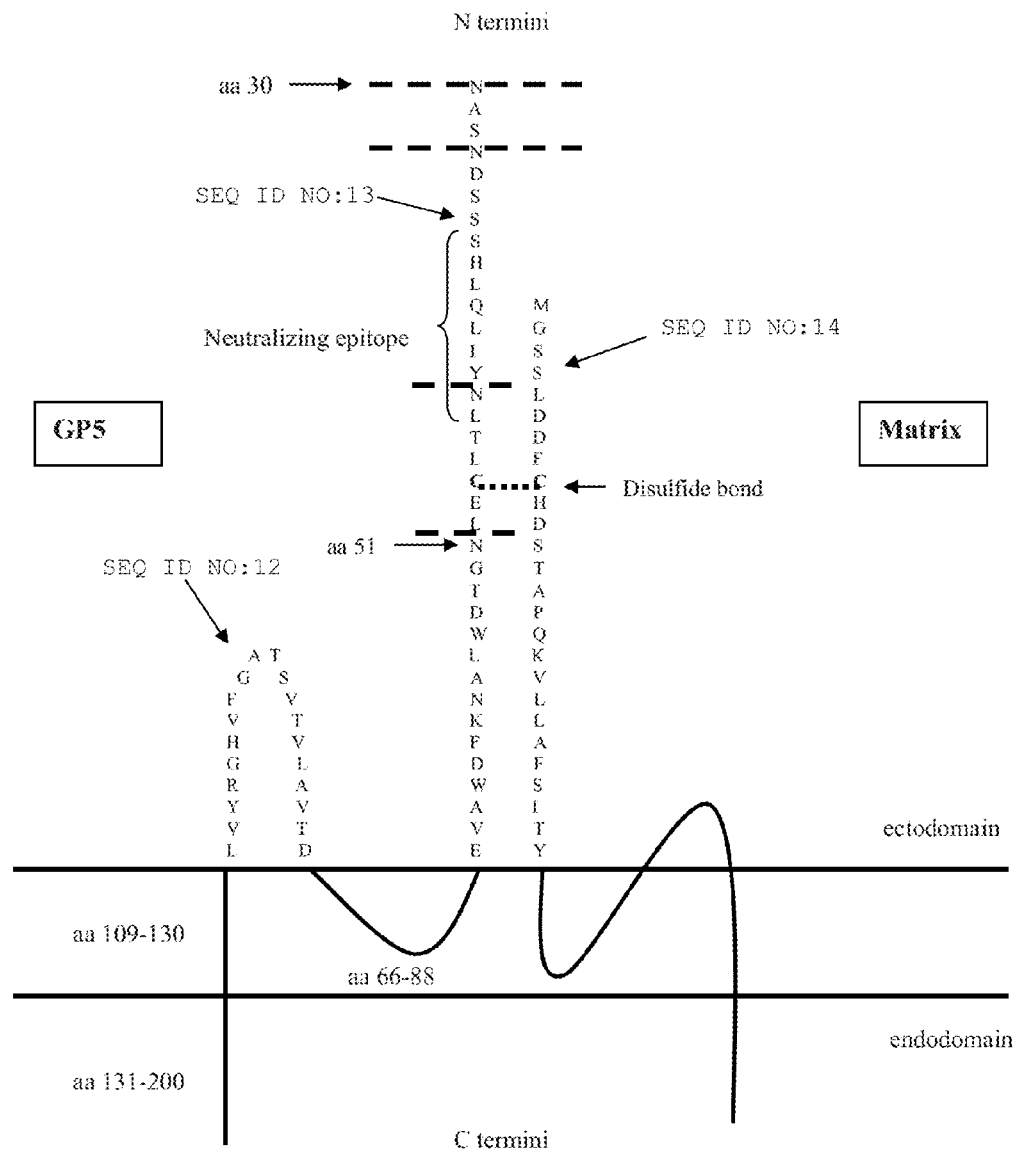

FIG. 9: VR2332GP5-M Heterodimer. Dashed lines indicate N-linked glycans (not to scale).

FIG. 16. Neutralizing epitope with no glycan block or shield.

FIG. 17. Neutralizing epitope with glycan block (BNE).

FIG. 18. Neutralizing epitope with glycan shield only.

FIG. 19. Highly glycosylated strain with glycan block and glycan shield.

FIG. 20. HLV013 complete ORF 5 and 6, corresponding to GP5 and M protein respectively.

FIGS. 21A and 21B. ORF6 sequences that encode the matrix protein.

FIGS. 22A and 22B. Examples of amino acid sequences of PRRSV GP5 signal sequence and ectodomain (SEQ ID NOS: 44-87 et. seq.).

FIG. 23. HLV092 complete ORF 5 corresponding to GP5.

FIG. 24. HLV093 complete ORF 5 corresponding to GP5.

DETAILED DESCRIPTION OF THE PREFERRED EMBODIMENT

Figure 2:
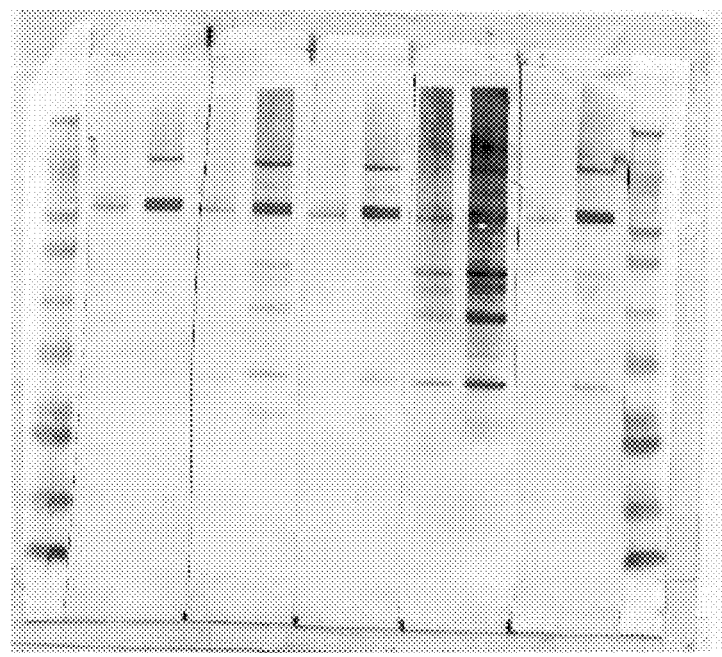
FIG. 2: Nonreduced Western immunoblot comparing VR2332 and HLV013 antisera. Pigs were immunized with either VR2332 or HLV013 on Day 1. All pigs were challenged with VR2332 on Day 90. Protein concentration was the same for both antigens tested. Antisera was diluted 1:4000. Lane 1 is standard ladder. Lane 2 is IA97-7895 antigen and normal swine serum. Lane 3 is HLV013 antigen and normal swine serum. Lane 4 is IA97-7895 antigen and HLV013 antisera 42 days post-inoculation (p.i.). Lane 5 is HLV013 antigen and HLV013 antisera 42 days p.i. Lane 6 is IA97-7895 antigen and VR2332 antisera 42 days p.i. Lane 7 is HLV013 antigen and VR2332 antisera 42 days p.i. Lane 8 is IA97-7895 antigen and HLV013 antisera 104 days p.i. Lane 9 is HLV013 antigen and HLV013 antisera 104 days p.i. Lane 10 is IA97-7895 antigen and VR2332 antisera 104 days p.i. Lane 11 is HLV013 antigen and VR2332 antisera 104 days p.i. Lane 12 is standard ladder.

The present inventors are first to identify a protective antigenic determinant (PAD) for porcine reproductive and respiratory syndrome virus (PRRSV) that provides treatment for and protection against PRRSV infection.

It is known that there is reduced or no heterologous protection with PRRSV vaccines. The present inventors propose that changes in the N-glycosylation patterns of asparagines in the glycoprotein 5 (GP5) ectodomain of PRRSV or changes in the conformation of GP5 from interactions with another protein, for example, the M protein of PRRSV, play an important role in providing protection against PRRSV. In one aspect, the GP5's structure is altered by forming a heterodimer with the M protein of PRRSV. See FIGS. 9-12. These changes in nucleotide or amino acid sequences may result in a conformational change or the addition or subtraction of N-linked glycosylation sites on the GP5 ectodomain. The present inventors also contemplate that changes to the M protein of PRRSV may also affect the heterodimer conformation. The present inventors believe that changes in the N-glycosylation patterns of asparagines in the glycoprotein 5 (GP5) ectodomain of PRRSV or a GP5-M heterodimer of glycoprotein 5 (GP5) and a matrix protein (M protein) of PRRSV linked by a disulfide bond gives rise to a PAD that provides protection against PRRSV infections. The disulfide bond connecting the M protein with the GP5 protein results from a cysteine amino acid located on the GP5 protein at position 48 for North American strains and at position 50 for European strains. In one aspect, the cysteine is located at position 9 of the M protein in North American PRRSV strains and at position 8 in European PRRSV strains.

In one embodiment, the invention provides one or more PADs that includes isolated polypeptides comprising an antigenic sequence comprising glycoprotein 5 (GP5) of PRRSV, wherein the GP5 protein has varying N-glycosylation patterns of asparagine amino acids located at positions 1-44 of the GP5 protein in North American PRRSV strains or at positions 1-46 of the GP5 protein in European PRRSV strains. In one aspect, the PAD includes the ectodomain of GP5. In another aspect, the PAD includes the neutralizing epitope of the ectodomain of GP5. In one aspect, the neutralizing epitope has an amino acid sequence of SHLQLIYNL (SEQ ID NO:92).

In yet another embodiment, the invention provides a PAD that includes an isolated polypeptide comprising an antigenic sequence comprising matrix (M) protein of PRRSV. In one aspect, the antigenic sequence is the ectodomain of the M protein. In one aspect, the ectodomain includes the first 30 amino acids or less of the M protein of NA or EU PRRSV strains.

In another embodiment, the antigenic sequence includes the GP5 sequence as described herein and a matrix protein (M protein) of PRRSV as described herein, wherein the GP5 protein is linked to the M protein by a disulfide bond, resulting from a cysteine amino acid of the M protein at position 9 in North American and at position 8 in EU PRRSV strains and a cysteine amino acid located at position 48 of the GP5 protein in North American PRRSV strains or from a cysteine amino acid located at position 50 in European PRRSV strains so that a GP5-M heterodimer is produced.

In one embodiment of the invention, a PAD of GP5 may have no glycans from amino acids 1-35 in the NA PRRSV GP5 protein. In another aspect, a PAD of GP5 may have a glycan at position 44 in the NA PRRSV GP5 protein. In another aspect, a PAD of GP5 may have a glycan at position 44 in the NA PRRSV GP5 and have glycans present or absent in amino acids 1-35 in the NA PRRSV GP5 protein, for example, as found in some NA PRRSV strains.

In one embodiment of the invention, a PAD of GP5-M heterodimer may have no glycans from amino acids 1-35 in the NA PRRSV GP5 protein. In another aspect, a PAD of GP5-M heterodimer may have a glycan at position 44 in the NA PRRSV GP5 protein. In another aspect, a PAD of GP5-M heterodimer may have a glycan at position 44 in the NA PRRSV GP5 and have glycans present or absent in amino acids 1-35 in the NA PRRSV GP5 protein, for example, as found in some NA PRRSV strains.

In one embodiment of the invention, a PAD of GP5 may have no glycans from amino acids 1-37 in the EU PRRSV GP5 protein, as found in Lelystad. In another aspect, a PAD of GP5 may have a glycan at position 46 in the EU PRRSV GP5 protein. In another aspect, a PAD of GP5 may have a glycan at position 46 in the EU PRRSV GP5 and have glycans present or absent in amino acids 1-37 in the EU PRRSV GP5 protein, for example, as found in some EU PRRSV strains.

In one embodiment of the invention, a PAD of GP5-M heterodimer may have no glycans from amino acids 1-37 in the EU PRRSV GP5 protein, as found in Lelystad. In another aspect, a PAD of GP5-M heterodimer may have a glycan at position 46 in the EU PRRSV GP5 protein. In another aspect, a PAD of GP5-M heterodimer may have a glycan at position 46 in the EU PRRSV GP5 and have glycans present or absent in amino acids 1-37 in the EU PRRSV GP5 protein, for example, as found in some EU PRRSV strains.

In another embodiment, the PAD includes an antigenic sequence comprising amino acids 36-45 of GP5 of NA PRRSV and the ectodomain of the M protein of PRRSV. In another aspect, the M protein ectodomain includes amino acids 1-30. In another embodiment of the invention the PAD includes an antigenic sequence comprising amino acids 38-47 of GP5 of EU PRRSV and the ectodomain of the M protein of PRRSV. The GP5 protein may have varying N-glycosylation patterns of asparagine amino acids located at positions 1-44 of the GP5 protein in North American PRRSV strains or at positions 1-46 of the GP5 protein in European PRRSV strains. These variations are also included in PADs of the invention.

Thus, with the identification of a PAD comprising a GP5 protein that is N-glycosylated or non-N-glycosylated from amino acids 1-46 of the GP5 ectodomain or an M protein or a GP5-M heterodimer of a M protein disulfide linked to a GP5 protein that is N-glycosylated or non-N-glycosylated from amino acids 1-46 of the GP5 ectodomain of PRRSV, it is possible to develop an effective vaccine against PRRSV.

A vaccine according to the present invention may include a PAD polypeptide as described herein, and may include but is not limited immunogenic fragments, derivatives, homologues or variants thereof, comprising an amino acid sequence at least 65% identical, 80% identical, 95% identical or 100% identical to any one of the PAD amino acid sequences of FIG. 1. SEQ ID NOS: 1-11.

The PADs according to the invention will include derivatives, homologues or variants thereof of, which fragments can be readily screened for immunogenic activity, as well as immunogenic fragments, for example, of those shown in FIGS. 1 and 21 (SEQ ID NOS: 1-11 and 29-43). Thus, derivatives, homologues or variants thereof can be tested using neutralizing assays or tested for the derivatives, homologues or variants thereof ability to provide protection against pigs challenged with a heterologous PRRSV using assays such as the fluorescent focusing neutralizing (FFN) test or Western blot assay for the heterodimer may be used to give an indication of heterologous antibody production. Thus, specific fragments may include but are not limited to fragments having amino acid sequences shown in FIGS. 1 and 21 (SEQ ID NO: 1-11 and 29-43). It is logical to presume that fragments of GP5-M heterodimers may provide similar degrees of protection.

In one aspect, the vaccine may be attenuated, inactivated, subunit, recombinant, vector, or DNA based. In still a further aspect, the vaccines may be used in an immunization scheme or protocol. In another aspect of the invention, a PAD may be utilized to produce antibodies to diagnose whether a PSSRV vaccination based on a PAD was successful or to produce vaccines for prophylaxis and/or treatment of PRRSV infections. In addition to use as vaccines, PAD polypeptides of the present invention can be used as antigens to stimulate the production of antibodies for use in passive immunotherapy, for use as diagnostic reagents, and for use as reagents in other processes such as affinity chromatography.

Definitions

As used herein, a "porcine reproductive and respiratory syndrome virus" or "PRRSV" refers to a virus which causes the diseases PRRS, PEARS, SIRS, MSD and/or PIP (the term "PIP" now appears to be disfavored), including the Iowa strain of PRRSV, other strains of PRRSV found in the United States (e.g., VR 2332), strains of PRRSV found in Canada (e.g., IAF-exp91), strains of PRRSV found in Europe (e.g., Lelystad virus, PRRSV-10), and closely-related variants of these viruses which may have appeared and which will appear in the future.

An unaffected pig is a pig which has either not been exposed to a porcine reproductive and respiratory disease infectious agent, or which has been exposed to a porcine reproductive and respiratory disease infectious agent such as PRRSV but is not showing symptoms of the disease. An affected pig is one which shows symptoms of PRRS or from which PRRSV can be isolated.

The terms "treating" or "treatment", as used herein, refer to reduction or alleviation of at least one adverse effect or symptom of PRRSV infection. The clinical signs or symptoms of PRRS may include weight loss, decreased weight gain, lethargy, respiratory distress, "thumping" (forced expiration), fevers, roughened haircoats, sneezing, coughing, eye edema and occasionally conjunctivitis. Lesions may include gross and/or microscopic lung lesions, myocarditis, lymphadenitis, encephalitis and rhinitis. In addition, less virulent and non-virulent forms of PRRSV and of the Iowa strain have been found, which may cause either a subset of the above symptoms or no symptoms at all. Less virulent and non-virulent forms of PRRSV can be used according to the present invention to provide protection against porcine reproductive and respiratory diseases nonetheless.

As used herein, an "ORF" refers to an open reading frame, or polypeptide-encoding segment, isolated from a viral genome, including a PRRSV genome. In the present polynucleic acid, an ORF can be included in part (as a fragment) or in whole, and can overlap with the 5'- or 3'-sequence of an adjacent ORF.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules, i.e., cDNA, mRNA, DNA-DNA, DNA-RNA and RNA-RNA hybrids, as well as "protein nucleic acids" (PNA) formed by conjugating bases to an amino acid backbone. This also includes nucleic acids containing modified bases.

A "vector" is any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. Viral vectors include alphavirus, retrovirus, adeno-associated virus, pox, baculovirus, vaccinia, herpes simplex, Epstein-Barr and adenovirus vectors. Non-viral vectors include, but are not limited to plasmids, liposomes, electrically charged lipids (cytofectins), DNA-protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell.

A cell has been "transformed" by exogenous or heterologous DNA when the transfected DNA effects a phenotypic change. The transforming DNA can be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, a "polypeptide" refers generally to peptides and proteins having more than eight amino acids.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a PAD are preferably optimized for expression in a particular host cell (e.g., yeast, mammalian, plant, fungal, and the like) used to produce the enzymes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994). Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, Proteins).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 86%, 87%, 88%, 89%, 90%, 91%, 92%, 93%, 94%, 95%, 96%, 97%, 98%, 99%, or higher identity over a specified region (e.g., the sequence of the neutralizing epitope of a GP5 protein of PRRSV), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to the compliment of a test sequence. The definition also includes sequences that have deletions and/or additions, as well as those that have substitutions. As described below, the preferred algorithms can account for gaps and the like. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1991, Adv. Appi. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement).

Another example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. Software for performing BLAST analyses is publicly available through the National Center for Biotechnology Information (http://world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions.

Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

As used herein, a protein or peptide is said to be "isolated" or "purified" when it is substantially free of cellular material or free of chemical precursors or other chemicals. The variant peptides of the present invention can be purified to homogeneity or other degrees of purity. The level of purification will be based on the intended use. The critical feature is that the preparation allows for the desired function of the variant peptide, even if in the presence of considerable amounts of other components.

In some uses, "substantially free of cellular material" includes preparations of the variant peptide having less than about 30% (by dry weight) other proteins (i.e., contaminating protein), less than about 20% other proteins, less than about 10% other proteins, or less than about 5% other proteins. When the variant peptide is recombinantly produced, it can also be substantially free of culture medium, i.e., culture medium represents less than about 20% of the volume of the protein preparation.

The language "substantially free of chemical precursors or other chemicals" includes preparations of the variant peptide in which it is separated from chemical precursors or other chemicals that are involved in its synthesis. In one embodiment, the language "substantially free of chemical precursors or other chemicals" includes preparations of the variant protein having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated variant proteins can be purified from cells that naturally express it, purified from cells that have been altered to express it (recombinant), or synthesized using known protein synthesis methods. For example, a nucleic acid molecule encoding the variant PAD protein is cloned into an expression vector, the expression vector introduced into a host cell and the variant protein expressed in the host cell. The variant protein can then be isolated from the cells by an appropriate purification scheme using standard protein purification techniques. Many of these techniques are described in detail below.

A protein is comprised of an amino acid sequence when the amino acid sequence is at least part of the final amino acid sequence of the protein. In such a fashion, the protein may be a PAD polypeptide, a variant PAD polypeptide and/or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. A brief description of how various types of these proteins can be made/isolated is provided below.

The variant proteins of the present invention can be attached to heterologous sequences to form chimeric or fusion proteins. Such chimeric and fusion proteins comprise a variant protein operatively linked to a heterologous protein having an amino acid sequence not substantially homologous to the variant protein. "Operatively linked" indicates that the variant protein and the heterologous protein are fused in-frame. The heterologous protein can be fused to the N-terminus or C-terminus of the variant protein.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

Polypeptides sometimes contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art. Accordingly, the variant peptides of the present invention also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cysteine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The present invention further provides fragments of the variant proteins of the present invention, in addition to proteins and peptides that comprise and consist of such fragments, provided that such fragments act as an antigenic determinant and/or provide treatment for and/or protection against PRRSV infections as provided by the present invention.

As used herein, a fragment comprises at least 8 or more contiguous amino acid residues from a PAD polypeptide or variant protein.

The terms "fragment," "derivative" and "homologue" when referring to the polypeptides according to the present invention, means a polypeptide which retains essentially the same biological function or activity as said polypeptide, that is, act as an antigenic determinant and/or provide treatment for and/or protection against PRRSV infections. Such fragments, derivatives and homologues can be chosen based on the ability to retain one or more of the biological activities of a PAD polypeptide, that is, act as an antigenic determinant and/or provide treatment for and/or protection against PRRSV infections. Thus, a homologue includes a polypeptide from a different strain or genus that retains essentially the same biological function or activity as the PAD polypeptide. The polypeptide vaccines of the present invention may be recombinant polypeptides, natural polypeptides or synthetic polypeptides, preferably recombinant polypeptides.

An "antigenic determinant" is, unless otherwise indicated, a molecule that is able to elicit an immune response in a particular animal or species. Antigenic determinants include proteinaceous molecules, i.e. polyaminoacid sequences, polypeptides, fragments, derivatives or variants that may include other moieties, for example, carbohydrate moieties, such as glycans, and/or lipid moieties.

Antigenic determinants of the present invention may also be heterologous, including antigenic determinants of neutralizing epitopes from other viruses, PRRSV strains or family, that cross-react with antibody or antiserum produced in response to a PAD of the present invention, for example, GP5-M heterodimers, and are able to elicit an immune response in a particular animal, such as a pig.

"M" as used herein refers to a matrix protein or polypeptide of PRRSV. The term "M" as used herein also includes fragment, derivatives or homologs thereof that can form a heterodimer with a GP5 protein and provide cross-reactivity with PRRSV strains.

"GP5" as used herein refers to a glycoprotein 5 of PRRSV. The term "GP5" as used herein also includes fragment, derivatives or homologs thereof that can form a heterodimer with a M protein and provide cross-reactivity with PRRSV strains. Thus, a homolog of GP5, for example, from another arterivirus virus, is contemplated as part of the invention. The position in the GP5 homolog that corresponds to position 44 of GP5 in NA PRRSV strains or to position 46 of GP5 in EU PRRSV strains can be determined by one skilled in the art and are also included as part of the invention.

The term "GP5-M heterodimer" as used herein also includes a GP5 protein associated with the M protein of PRRSV or any other protein or peptide that alters the conformation of GP5 such that when administered to a pig provides protection against PRRSV. One skilled in the art would be able to test for conformational changes of GP5 using standard techniques and methods, for example, using a monoclonal antibody that only recognizes the GP5 protein when it is not in heterodimeric form. Thus, one aspect of the invention includes GP5 or M proteins from the same or from differing strains or viruses, including but not limited to equine arteritis virus (EAV), lactate dehydrogenase-elevating virus (LDV), and simian hemorrhagic fever virus (SHFV) family members. Therefore according to the invention, chimeric GP5-M heterodimers may be employed as PAD, for example, for use in immunization protocols.

As used herein, the ectodomain of the GP5 protein is approximately 60-65 amino acids in length includes a signal peptide and post-processing a short N-terminal region of approximately 30 amino acids in length which may include N-glycosylation sites. See FIG. 1. As used herein, the term "hypervariable" region refers to a region of the ectodomain of the GP5 protein, for example, amino acids 1 to 35 of GP5 in (NA) North American strains of PRRSV and amino acids 1 to 37 of GP5 in (EU) European like PRRSV strains or of a GP5 homolog or equivalent thereof. Corresponding regions and positions of the ectodomain in other fragments, homologs or derivatives of GP5 can be determined for example by alignment and used in the present invention. Also, contemplated as part of the invention are mutations of one or more amino acids in the ectodomain of GP5 that result in the glycosylation of that amino acid. Thus, it may be possible to generate a GP5 that has glycosylation in the ectodomain at a position other than 44 in NA PRRSV strains or 46 in EU PRRSV strains that has the same effect (protection against PRRSV infection). These variants may also be used in the present invention.

As used herein, the ectodomain of the M protein refers to the first 30 amino acids of the N-terminus of the M protein or of a homolog or equivalent thereof. Corresponding regions and positions of the ectodomain in other fragments, homologs or derivatives of M protein can be determined for example by alignment and used in the present invention.

The phrase "biological sample" refers to a fluid or tissue of a mammal (e.g., a pig, rabbit, horse) that commonly contains antibodies or viral particles. Such components are known in the art and include, without limitation, blood, plasma, serum, spinal fluid, lymph fluid, secretions of the respiratory, intestinal or genitourinary tracts, tears, saliva, milk, white blood cells, and myelomas.

As used herein, an antibody is defined in terms consistent with that recognized within the art: they are multi-subunit proteins produced by a mammalian organism in response to an antigen challenge. The antibodies of the present invention include monoclonal antibodies and polyclonal antibodies, as well as fragments of such antibodies, including, but not limited to, Fab or F(ab')hd 2, and Fv fragments.

As used herein, the term "subunit" refers to a portion of the PRRSV which is itself antigenic, i.e., capable of inducing an immune response in an animal. The term should be construed to include subunits which are obtained by both recombinant and biochemical methods.

As used herein, the term "multivalent" means a vaccine containing more than one isolate from the PRRSV, whether from the same species (i.e., different isolates of PRRSV) or from a different PRRSV. Even for a given genus and species of PRRSV each isolate may share some antigens with other isolates (i.e., "common" antigens), while other antigens will be unique to that isolate. Because a multivalent vaccine provides a greater variety of antigens to the host's immune system, the immune response stimulated in the host is broader than that stimulated by only a single isolate.

As used herein, the term "isolate" refers to a virus obtained from a specific source. Isolate is used interchangeably with the term "strain".

As used herein, the term "virulent" means an isolate that retains its ability to be infectious in an animal host.

As used herein, the term "inactivated" means a vaccine containing an infectious organism that is no longer capable of replication and/or growth.

As used herein, the term "PRRSV" as used herein refers to all viruses belonging to species PRRSV in the genus Arterivirus within the family Arteriviridae.

As used herein, the term "vaccine" as used herein refers to a pharmaceutical composition comprising at least one immunologically PAD that induces an immunological response in an animal and possibly, but not necessarily, one or more additional components that enhance the immunological activity of said active component. A vaccine may additionally comprise further components typical to pharmaceutical compositions. The immunologically active component of a vaccine may comprise complete live virus in either its original form or as attenuated virus in a so-called modified live vaccine or virus inactivated by appropriate methods in a so-called killed vaccine. In another form, the immunologically active component of a vaccine may comprise appropriate elements of said viruses (subunit vaccines) whereby these elements are generated either by destroying the whole organism or the growth cultures of such viruses and subsequent purification steps yielding in the desired structure(s), or by synthetic processes induced by an appropriate manipulation of a suitable system such as, but not restricted to, bacteria, insects, mammalian, or other species, plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above.

The terms "protecting", "protection", "protective immunity" or "protective immune response," as used herein, are intended to mean that the host pig mounts an active immune response to the vaccine or polypeptides of the present invention, such that upon subsequent exposure to the virus or a virulent viral challenge, the pig is able to combat the infection. Thus, a protective immune response will decrease the incidence of morbidity and mortality from subsequent exposure to the virus among host pigs. Those skilled in the art will understand that in a commercial pig setting, the production of a protective immune response may be assessed by evaluating the effects of vaccination on the herd as a whole, e.g., there may still be morbidity and mortality in a minority of vaccinated pigs. Furthermore, protection also includes a lessening in severity of any gross or histopathological changes (e.g., lesions in the lung) and/or of symptoms of the PPRS disease, as compared to those changes or symptoms typically caused by the isolate in similar pigs which are unprotected (i.e., relative to an appropriate control). Thus, a protective immune response will decrease the symptoms of PRRSV, including but not limited to a reduction in the clinical signs or symptoms of PRRS comprising weight loss, decreased weight gain, lethargy, respiratory distress, "thumping" (forced expiration), fevers, roughened haircoats, sneezing, coughing, eye edema, conjunctivitis, gross lesions microscopic lung lesions, myocarditis, lymphadenitis, encephalitis and rhinitis compared to the control pig.

As used herein, the term "live virus" refers to a virus that retains the ability of infecting an appropriate subject (as opposed to inactivated (killed) or subunit vaccines).

As used herein, "immunogenically effective amount" refers to an amount, which is effective in reducing, eliminating, treating, preventing or controlling the symptoms of the PRRSV infections, diseases, disorders, or condition.

In one embodiment, the present invention relates to a polypeptide comprising a PAD of PRRSV, herein referred to as a PAD polypeptide. The present inventors contemplate that the polypeptide may be a homologue, a derivative, or a variant of the PAD, or an immunologically active or a functional fragment thereof. The polypeptide may be isolated, synthesized, or recombinantly expressed using the PAD-encoding nucleic acids described herein.

Examples of PADs of the present invention include but are not limited to the amino acid sequences shown in FIGS. 1, 20, 21 and 22 (SEQ ID NOS: 1-11 and 25-87). These PADs may be administered as fragments, polypeptides, proteins, or as a PRRSV having the desired glycosylation of the ectodomain of the GP5-M heterodimer according to the immunization protocols described herein. Further examples of nucleic acid molecules of the present invention include, but are not limited to the polynucleotide sequences that encode the polypeptide of (HLV013) MLGRCLTAGC CSQLPFLWCI VPFCL-VALVN ANSNSGSHLQ LIYNLTLCEL NGTDWLKDKF (SEQ ID NO: 93) or the polypeptide of and HLV093 MLGR-CLTACY CLRLLSLWCI VPFWFAVLVS ANSNSSSHLQ SIYKLTLCEL NGTEWLNERF (SEQ ID NO: 94).

The present invention also provides isolated and/or recombinant nucleic acids that encode a PAD polypeptide of the invention. According to an embodiment of the invention, the nucleotide sequence of a PAD encodes a neutralizing epitope of PRRS. In addition, it should be understood based on the general state of the art that other equivalent sequences to the nucleotide or amino acid sequences of the PADs are covered by the present invention. For example, some deletions, insertions and substitutions in the amino acid sequence of the ectodomain of the GP5 are covered by the present invention, unless such mutation abolishes the ability of the PAD to induce the generation of neutralizing antibody.

The PAD-encoding nucleic acids of the invention are useful for several purposes, including the recombinant expression of the corresponding PAD polypeptides.

Nucleic acids of the invention include those that encode an entire PAD as well as those that encode a subsequence of a PAD polypeptide. For example, the invention includes nucleic acids that encode a polypeptide which is not a full-length PAD, but nonetheless has protective antigenic activity against PRRSV infection. The invention includes not only nucleic acids that include the nucleotide sequences as set forth herein, but also nucleic acids that are substantially identical to, or substantially complementary to, the exemplified embodiments. For example, the invention includes nucleic acids that include a nucleotide sequence that is at least about 70% identical to one that is set forth herein, more preferably at least 75%, still more preferably at least 80%, more preferably at least 85%, still more preferably at least 90%, and even more preferably at least about 95% identical to an exemplified nucleotide sequence. The nucleotide sequence may be modified as described previously, so long as the polypeptide encoded is capable of inducing the generation of neutralizing antibodies.

The nucleic acids that encode a PAD polypeptide of the invention can be obtained using methods that are known to those of skill in the art. Suitable nucleic acids (e.g., cDNA, genomic, or subsequences) can be cloned, or amplified by in vitro methods such as the polymerase chain reaction (PCR) using suitable primers, the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Amheim & Levinson (Oct. 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Nucleic acids that encode the PAD polypeptide of the invention, or subsequences of these nucleic acids, can be prepared by any suitable method as described above, including, for example, cloning and restriction of appropriate sequences.

A nucleic acid encoding a PAD polypeptide may then be introduced into either a prokaryotic or eukaryotic host cell through the use of a vector, plasmid or construct and the like to produce the PAD polypeptide of the invention. A typical expression cassette contains a promoter operably linked to a nucleic acid that encodes the glycosyltransferase or other enzyme of interest. The expression cassettes are typically included on expression vectors that are introduced into suitable host cells, including for example, bacterial, insect, fungal, plant or animal cells. Either constitutive or regulated promoters can be used in the present invention. Promoters suitable for use in eukaryotic host cells are well known to those of skill in the art. The expression vectors of the invention can be transferred into the chosen host cell by methods known to those of ordinary skill in the art including, for example, calcium phosphate transfection, DEAE-dextran mediated transfection, transvection, microinjection, cationic lipid-mediated transfection, electroporation, transduction, scrape loading, ballistic introduction, infection or other methods. (See *Molecule Cloning: A Laboratory Manual*, $2^{nd}$ ed., Vol. 1-3, ed. Sambrook et al., Cold Spring Harbor Laboratory Press (1989)). Transformed cells can be selected, for example, by resistance to antibiotics conferred by genes contained on the plasmids, such as the amp, gpt, neo and hyg genes.

A PAD polypeptide, homologue, fragments or other derivatives, or variants thereof, or cells expressing it can be used as an antigen to produce antibodies thereto. The present invention includes, for examples monoclonal and polyclonal antibodies, chimeric, single chain, as well as Fab fragments. Thus, the present invention also encompasses a method of generating antibodies directed against one or more PAD polypeptides described above comprising providing a polypeptide of the PAD or a biologically functional homologue or derivative or variant thereof and administering the polypeptide to an animal subject in an amount sufficient to induce an immunological response to generate antibodies directed towards the PAD polypeptide. Thus, the invention includes a method for generating antibodies against a protective antigenic determinant (PAD) of PRRSV that includes administering to an animal a first GP5-M heterodimer, where the GP5 of the first GP5-M heterodimer has glycosylation at position 44 of the GP5 of a North American (NA) PRRSV or glycosylation at position 46 of the GP5 of a European (EU) PRRSV. The method also includes administering to the animal a second GP5-M heterodimer, where the GP5 of the second GP5-M heterodimer does not have glycosylation at position 44 of GP5 of a North American (NA) PRRSV or at position 46 of the GP5 of a European (EU) PRRSV. The inventors also contemplate that amino acids of 51 and 53 in GP5 in NA and EU PRRSV respectively may be important for use as a PAD and believe that they may be involved in viral attachment and that VN antibodies may react with them. The PADs of the invention may be administered according to the immunization protocol described herein. In another aspect of the invention, the animal is a non-human, for example, a rat, horse, cow, mouse, pig, sheep, rabbit, or chicken.

Thus, the invention provides antibodies that selectively bind to the PAD polypeptide, a derivative, a homologue or a variant as well as fragments thereof. Such antibodies may be used to quantitatively or qualitatively detect the PAD polypeptide or variants as described previously.

Many methods are known for generating and/or identifying antibodies to a given target peptide, such as a PAD polypeptide. Several such methods are described by Harlow, *Antibodies*, Cold Spring Harbor Press, (1989). The full-length PAD polypeptide, derivative, homologue or variant or fragments or a fusion protein can be used.

For preparation of monoclonal antibodies, any technique known in the art which provides antibodies produced by continuous cell line cultures can be used. Examples include various techniques, such as those in Kohler, G. and Milstein, C., *Nature* 256:495-497 (1975); Kozbor et al., *Immunology Today* 4:72 (1983); (Cole et al., pg. 77-96 in Monoclonal Antibodies and Cancer Therapy, Alan R. Liss, Inc. (1985). Monoclonal antibodies can be produced by hybridomas, which are immortalized cell lines capable of secreting a specific monoclonal antibody. The immortalized cell lines can be created in vitro by fusing two different cell types, usually lymphocytes, one of which is a tumor cell.

The anti-PAD antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PAD polypeptide, derivative, a homologue or a variant as well as fragments or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

In another embodiment of the present invention, a method is provided for preparing a vaccine against PRRSV. In one aspect, the method comprises providing a PAD polypeptide, a derivative, a homologue or a variant or fragments thereof. Alternately, the method for preparing a vaccine against PRRSV may include mixing the PAD polypeptide with a physiologically acceptable carrier or diluent. Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical or physiological carriers are generally added that are compatible with the active ingredients and acceptable for pharmaceutical use. Examples of such carriers include, but are not limited to, water, saline solutions, dextrose, or glycerol. Combinations of carriers may also be used. One of ordinary skill in the art would be familiar with pharmaceutically or physiologically acceptable carriers or diluents.

In view of the above, the present invention also provides for a vaccine. In another embodiment, there is provided a vaccine which includes at least one PAD polypeptide, a derivative, a homologue or a variant or fragment thereof. In another aspect, the vaccine comprises a nucleic acid encoding a PAD polypeptide, a derivative, a homologue or a variant or fragment thereof.

The present invention provides for vaccines that are killed (inactivated), attenuated (live modified), subunit, DNA, or recombinant vector based. The invention provides in a further aspect a vaccine for use in the protection of pigs against disease conditions resulting from a PRRSV infection. The vaccines of the present invention are generally intended to be a prophylactic treatment which immunizes pigs against disease caused by virulent strains of PRRSV. However, the vaccines are also intended for the therapeutic treatment of pigs already infected with a virulent strain of PRRSV.

Figure 16:
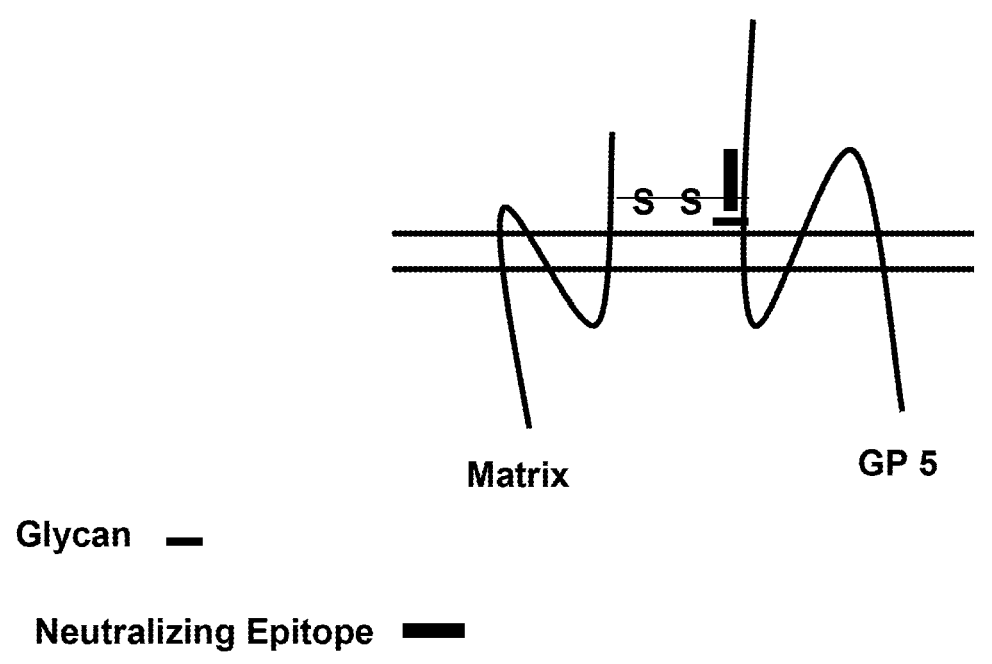
Figure 17:
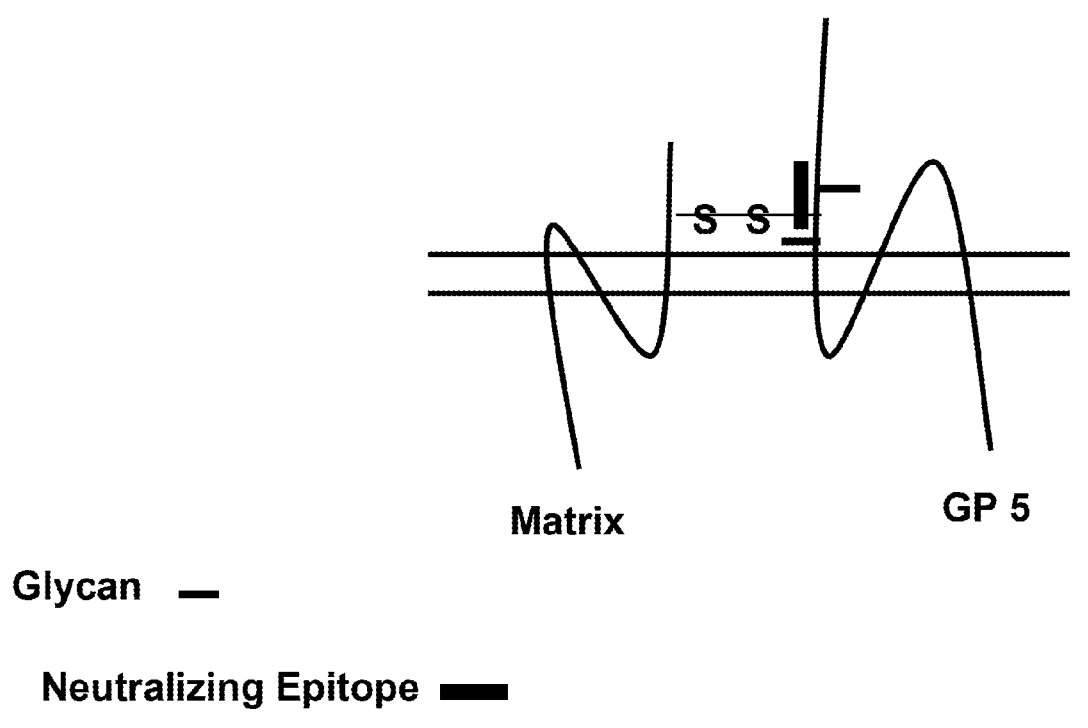

The present inventors contemplate that PRRSV treatment and prevention may be based on an entirely different theory than current vaccine strategies, e.g. strategies involving mechanisms associated with either cell mediated immunity (CMI) and/or virus neutralizing (VN) antibodies. The inventors believe that the PRRSV has a "glycan shield" that may either block or shield neutralizing epitopes (NE). The shield prevents the humoral immune response from recognizing key neutralizing epitopes containing asparagine-linked glycans or other sugar moieties, so that the neutralizing epitopes are unavailable for generation of neutralizing antibodies. The inventors also believe that PRRSV has a NE block glycan in some situations (FIG. 17). When a host "species jump" occurs by an RNA virus, neutralizing antibody (Nab) to the NE may be readily induced (FIG. 16). These first "species jump" trains with no glycans in block or shield positions are readily eliminated by Nab to NE.

Figure 10:
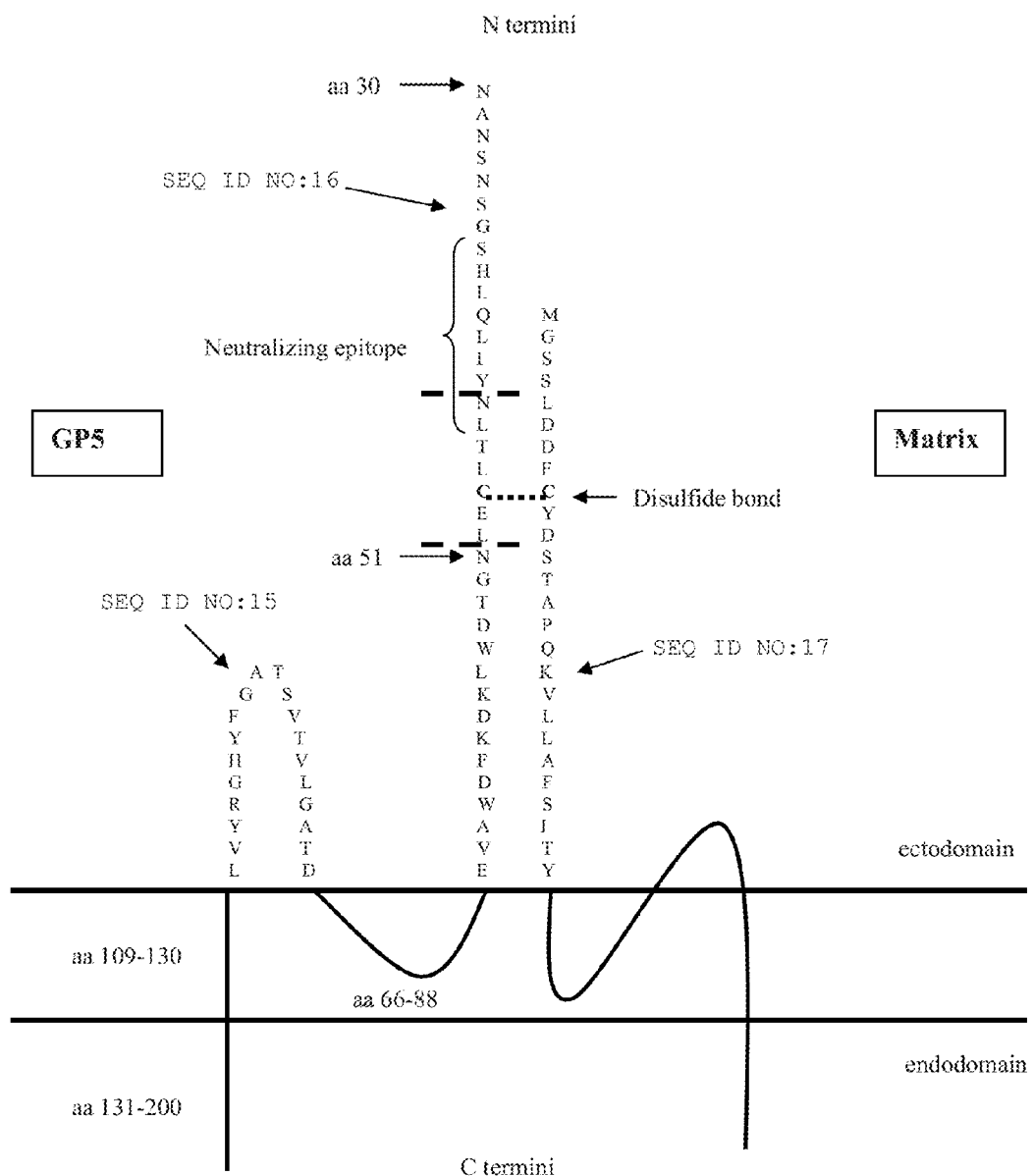
FIG. 10: HLV013 GP5-M Heterodimer.
Figure 11:
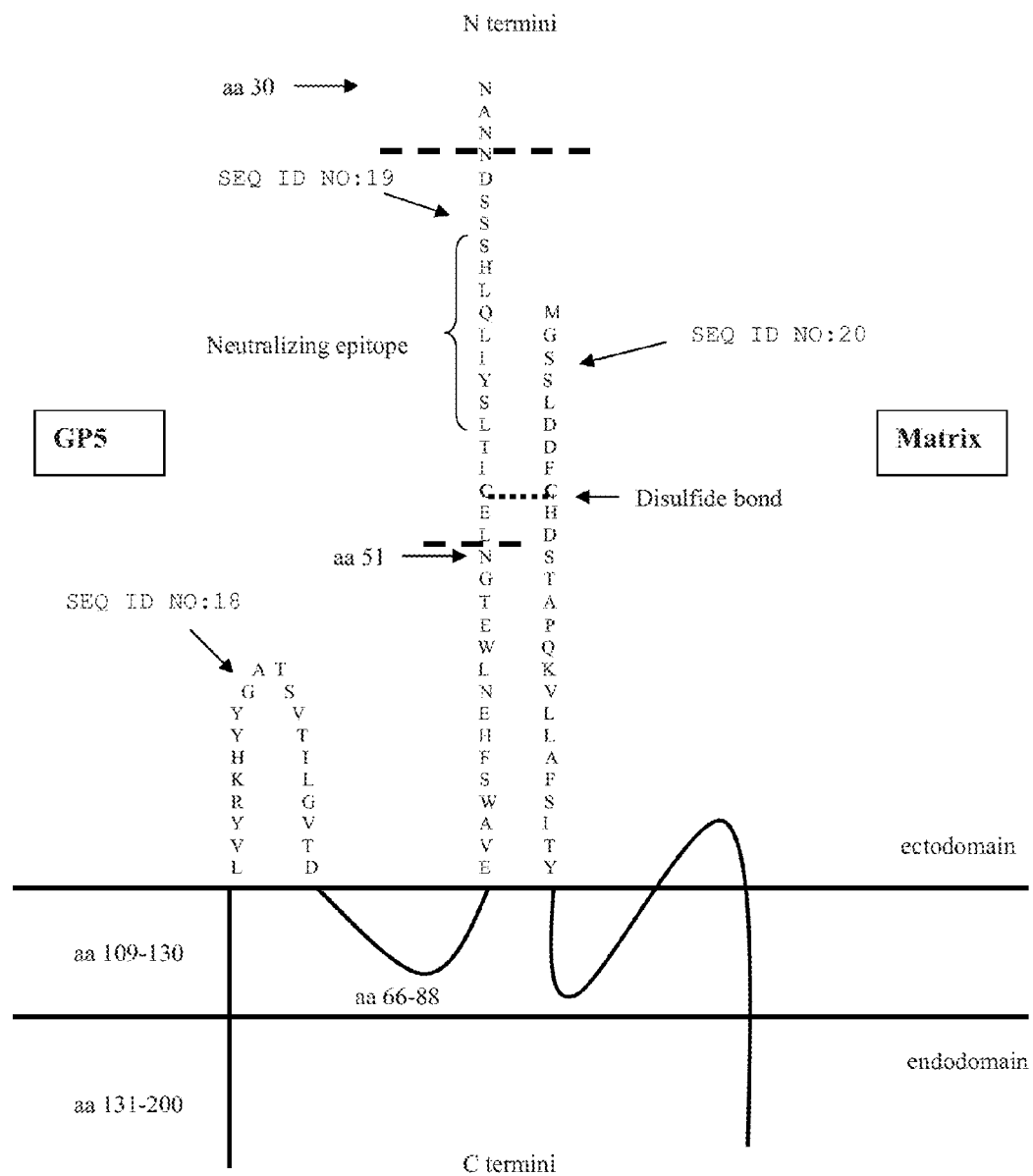
FIG. 11: HLV093 GP5-M Heterodimer.
Figure 12:
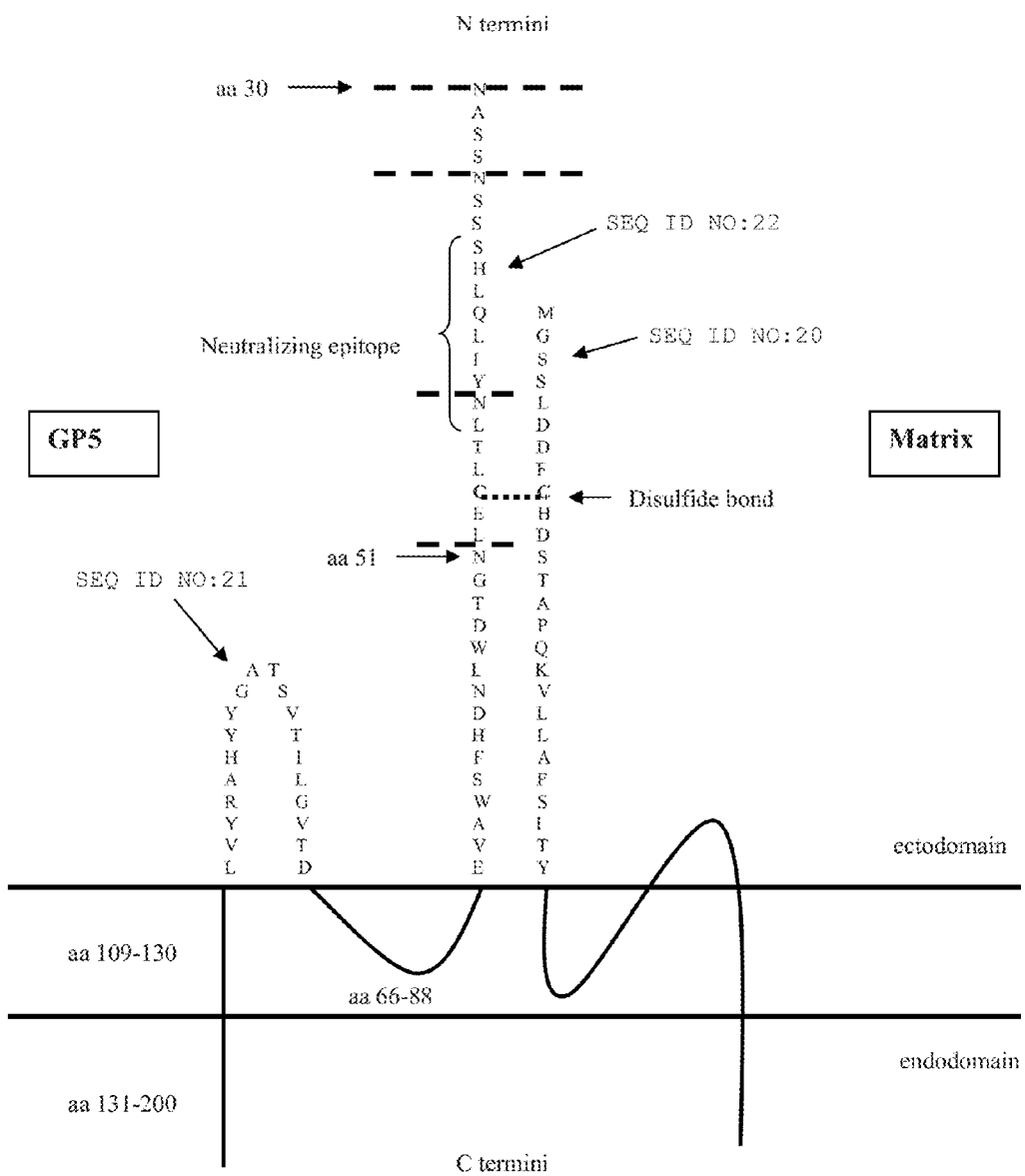
FIG. 12: HLV092 GP5-M Heterodimer.
Figure 13:
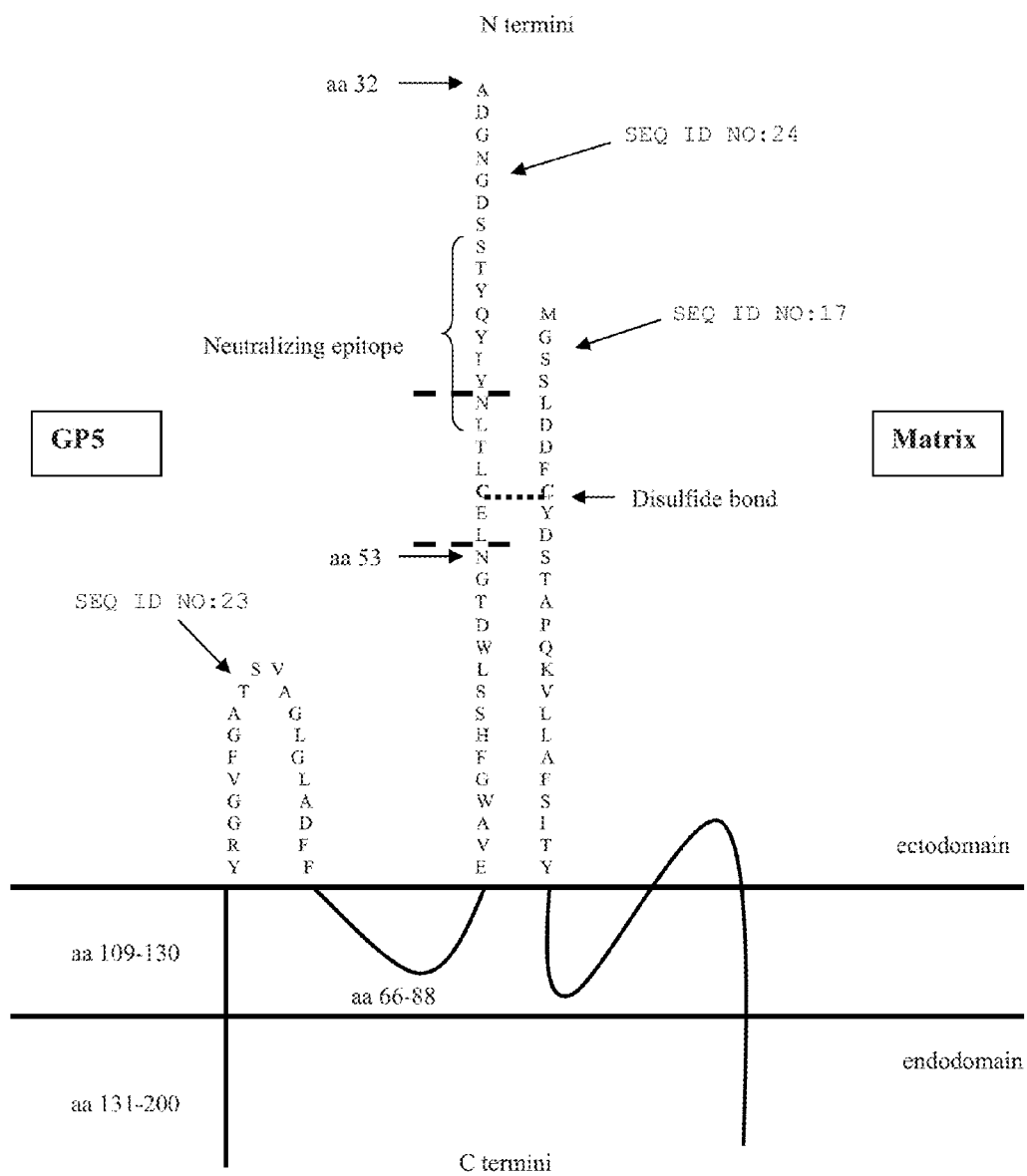
FIG. 13: Lelystad GP5-M Heterodimer.
Figure 14:
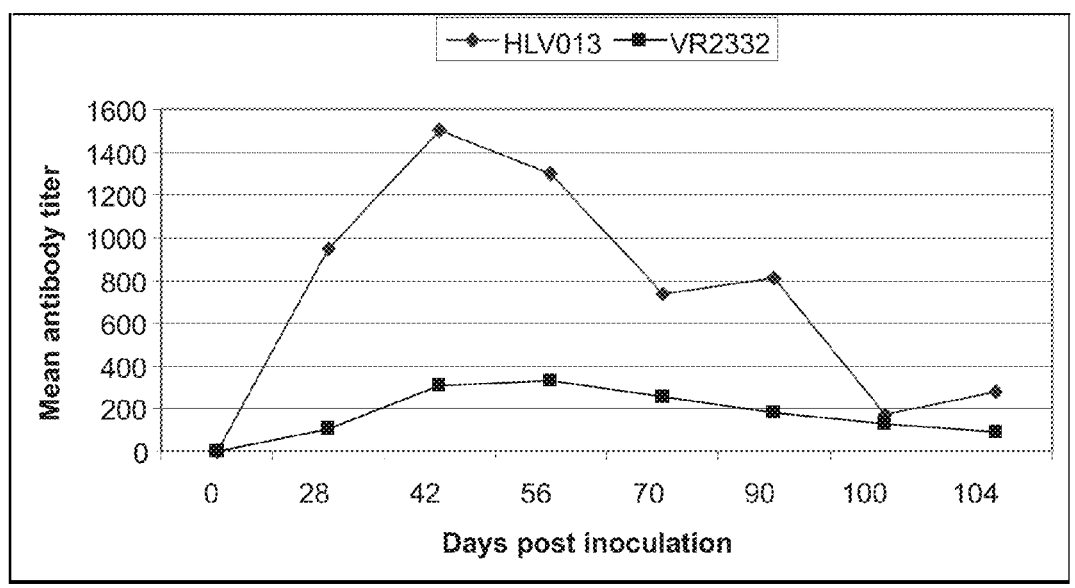
FIG. 14: Peptide ELISA data. The peptide ELISA detects antibody to the virus neutralizing epitope of PRRSV GP5. Pigs (n=6 per group) were inoculated with equal titers of either HLV013 or VR2332PRRSV on Day 0.

As new host species become infected or quasispecies develop, the NE becomes blocked (BNE) by glycan(s) in direct proximity (conserved region) of the NE (FIG. 17), for example, the sequence of HLV013 in FIG. 10. Subsequently, Nab is created to the BNE. Next a shield of glycans (SNE) evolves on emerging quasispecies in hypervariable region(s) in proximity of the NE. Thus, Nab may be slow to develop and/or be ineffective against escape mutants containing both BNE and SNE (FIG. 19).

Figure 18:
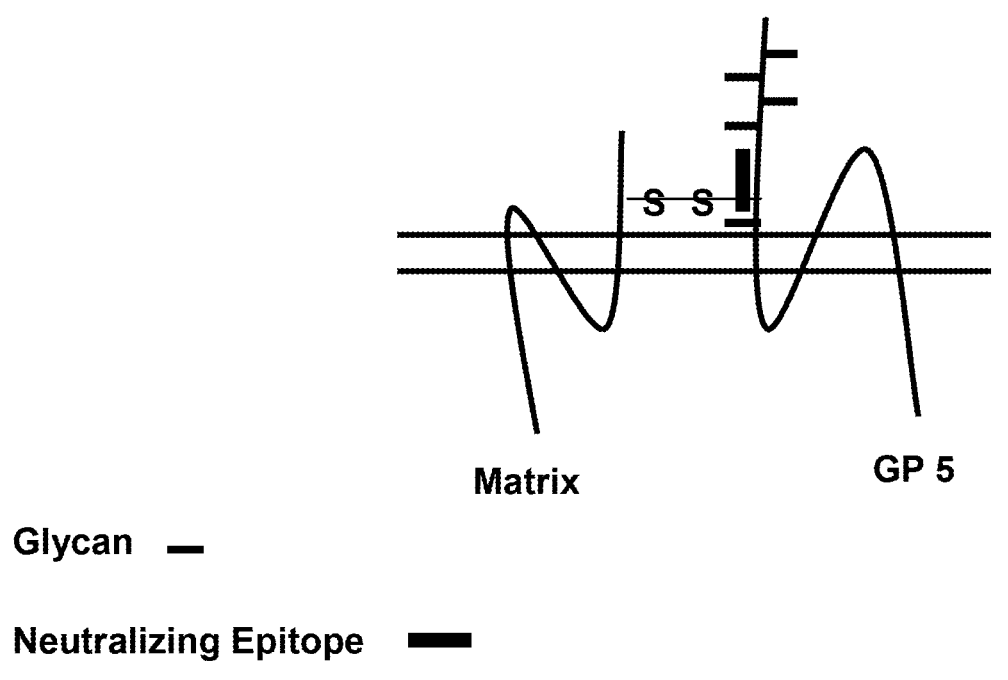

If only the glycan shield is present e.g. rare wild type mutants, then Nab is induced to the NE (FIG. 19), for example, HLV093. See FIG. 11. This Nab protects against strains with only the glycan shield. Thus, strains with only a glycan shield are not maintained in the susceptible host population. The sequential immunization of wild type mutants possessing no glycan shield (BNE [FIG. 17] followed by NE [FIG. 18]) results in polyclonal Nab which protects against predominant emerging heterologous virus strains and provides cross-reactivity (FIG. 19).

Figure 19:
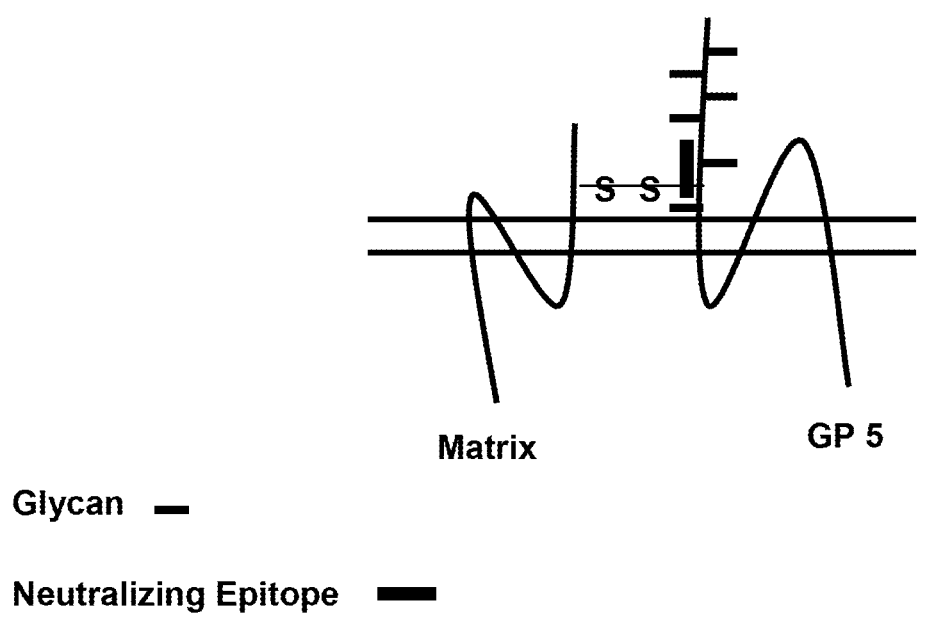

Thus, viruses emerge by first forming a glycan block and then a glycan shield (FIG. 19). Heterologous Nab may be produced by first inoculating a glycan blocked epitope (BNE) without a glycan shield followed by a NE without the glycan block which is referred to as reversed epitope evolution immunization.

Thus, the present inventors believe that when a pig is exposed to an initial and then a subsequent differing strain of PRRSV that is more glycosylated in the hypervariable ectodomain of GP5, the pig's immune system only recognizes non-glycosylated regions on GP5 and M in the neutralizing epitope and shared epitopes between the serotypes. As a consequence, the immune system is unable to recognize new glycosylated epitopes on PRRSV resulting in ineffective immunity.

The present inventors are first to recognize that this theory can be exploited for use in the development and administration of single or multivalent PRRSV vaccines and PRRSV immunization schemes using glycantyping of PRRSV isotypes. Thus, glycosylation patterns (glycantypes) of PRRSV may be used for initial grouping of PRRSV strains.

According to the present invention, PRRSV strains within the North American and European genotypes are grouped based on their glycosylation patterns. This discovery is referred to by the inventors as a glycantyping scheme. Glycantyping is a more accurate means of discerning heterologous PRRSV strains as new strains emerge in the population than sequence homology of ORFS. The present inventors contemplate that the discernment of glycosylation patterns can be used in single or multivalent vaccines or in the development of vaccination schemes and protocols. In one aspect, the strains are classified based on whether they are European or North American strains. In another aspect of typing the PRRSV strains, the first letter is either EU (European like) or NA (North American like) to designate the genotype cluster. As used herein, EU refers to isotypes of PRRSV characterized by conserved glycans at position 46, 53, or both in GP5. As used herein, NA refers to isotypes of PRRSV characterized by conserved glycans at position 44, 51, or both in GP5. Each strain is given a number corresponding to the number of glycosylation sites located in the ectodomain of GP5 amino acid sequence shown in Table 7, but excludes highly conserved glycans located at aa44 and 51 for NA strains and aa46 and 53 for EU strains. Thus, NA-0 refers to the ectodomain of GP5 of NA strain that has no glycan and EU-0 refers to the ectodomain of GP5 of an EU strain that has no glycan. For example, NA-1 refers to the ectodomain of GP5 of a North American strain that has 1 glycan located on the ectodomain of GP5 excluding highly conserved glycans located at aa44 and 51 for NA strains.

The present invention also contemplates that newly identified PRRSV strains may be glycantyped using the above described methodology and accordingly used in embodiments of the present invention. The inventors also contemplate that glycantyping schemes described herein may also be applicable in treating or preventing other viruses that utilize a "glycan shield" to evade the immune system, for example, in designing immunization protocols. New or known PRRSV strains can also be isolated from the field using standard techniques and methods known in the art.

According to the invention, virulent or avirulent PRRSV may be used in a vaccine or in an immunization protocol. The inventors have found that this method of administering PRRS viral strain with N-glycosylation in the ectodomain of GP5, in particular a glycan at position 44 (or 46) depending on whether the GP5 mimics a North American or European PRRSV in the GP5-M heterodimer to vaccinate pigs is particularly capable of priming a pig's immune system to elicit a greater immune response when followed by administration with a PRRSV strain having no glycosylated amino acids in the GP5 ectodomain and subsequently challenged with a PRRSV having glycosylation ectodomain in its GP5 polypeptide. See Table 6. This rational is based on the fact that glycans in the GP5 hypervariable region may inhibit/delay a protective antibody response to the PADs. Furthermore, it is believed that the absence of a glycan at position 44 contributes to protection against heterologous strains of the virus. For example, a strain such as HLV093 that is deficient of glycans in its neutralizing epitope in GP5 may be used to prime the immune response prior to encountering other glycantypes of PRRSV. Fore example, a strain such as HLV013 that is deficient of glycans in its hypervariable region (1-37) in GP5 may be used to prime the immune response prior to encountering other glycantypes of PRRSV.

In one aspect of the immunization protocol against a PPRSV infection, a virus having a PAD of a GP5-M heterodimer of PRRSV of the present invention with glycosylation at position 44 of GP5 in a North American strain is administered, followed by administration of a virus having a PAD of a GP5-M heterodimer of PRRSV of the present invention without glycosylation at position 44 of GP5 in a North American strain, and then challenged with a PRRSV having glycosylation in the neutralizing epitope of GP5.

In another aspect, a virus having a PAD of a GP5-M heterodimer of PRRSV of the present invention with glycosylation at position 46 in GP5 in a European strain is administered, followed by administration of a virus having a PAD of a GP5-M heterodimer of PRRSV of the present invention without glycosylation at position 46 in GP5 in a European strain, and then challenged with a PRRSV having glycosylation in the neutralizing epitope of GP5.

In one aspect of the immunization protocol against a PPRSV infection, a PAD comprising a GP5-M heterodimer of PRRSV of the present invention with glycosylation at position 44 of GP5 in a North American strain is administered, followed by administration of a PAD comprising a GP5-M heterodimer of PRRSV of the present invention without glycosylation at position 44 of GP5 in a North American strain, and then challenged with a strain of PRRSV having glycosylation in the neutralizing epitope of GP5. In another aspect, a PAD comprising a GP5-M heterodimer of PRRSV of the present invention with glycosylation at position 46 of a GP5 in a European strain is administered, followed by administration of a PAD comprising a GP5-M heterodimer of PRRSV of the present invention without glycosylation at position 46 of GP5 in a European strain, and then challenged with a strain of PRRSV having glycosylation in the neutralizing epitope of GP5.

In one embodiment of the invention, a PAD of GP5 may have no glycans from amino acids 1-35 in the NA PRRSV GP5 protein. In another aspect, a PAD of GP5 may have a glycan at position 44 in the NA PRRSV GP5 protein. In another aspect, a PAD of GP5 may have a glycan at position 44 in the NA PRRSV GP5 and have glycans present or absent in amino acids 1-35 in the NA PRRSV GP5 protein, for example, as found in some NA PRRSV strains.

In one embodiment of the invention, a PAD of GP5-M heterodimer may have no glycans from amino acids 1-35 in the NA PRRSV GP5 protein. In another aspect, a PAD of GP5-M heterodimer may have a glycan at position 44 in the NA PRRSV GP5 protein. In another aspect, a PAD of GP5-M heterodimer may have a glycan at position 44 in the NA PRRSV GP5 and have glycans present or absent in amino acids 1-35 in the NA PRRSV GP5 protein, for example, as found in some NA PRRSV strains.

In one embodiment of the invention, a PAD of GP5 may have no glycans from amino acids 1-37 in the EU PRRSV GP5 protein, as found in Lelystad. In another aspect, a PAD of GP5 may have a glycan at position 46 in the EU PRRSV GP5 protein. In another aspect, a PAD of GP5 may have a glycan at position 46 in the EU PRRSV GP5 and have glycans present or absent in amino acids 1-37 in the EU PRRSV GP5 protein, for example, as found in some EU PRRSV strains.

In one embodiment of the invention, a PAD of GP5-M heterodimer may have no glycans from amino acids 1-37 in the EU PRRSV GP5 protein, as found in Lelystad. In another aspect, a PAD of GP5-M heterodimer may have a glycan at position 46 in the EU PRRSV GP5 protein. In another aspect, a PAD of GP5-M heterodimer may have a glycan at position 46 in the EU PRRSV GP5 and have glycans present or absent in amino acids 1-37 in the EU PRRSV GP5 protein, for example, as found in some EU PRRSV strains.

The present immunization process against PRRSV is advantageous in that it results in the generation of high levels of neutralizing antibodies in an early antibody response when challenged with PRRSV of various strains that provides heterologous reactivity. It is believed that immunization protocols described herein may be applicable to the treatment and prevention of other viral infections, including, but not limited to HIV and influenza.

Thus, strains including and similar to HLV013 may or may not provide direct protection against all other glycantypes but rather indirect protection by readying the immune system to progressively encounter PRRSV PADs with varying degrees of glycan masking By contrast, subsequent inoculation of PADs of different strains similar to HLV093 in glycosylation of the hypervariable ectodomain of GP5 may provide access to important neutralizing epitopes in all PRRSV strains, such as those more glycosylated in the hypervariable ectodomain of GP5. In this way, the glycantyping of PRRSV creates a ranking or order or combination of PRRSV administration effective in generating an immune response to multiple PRRSV. In one aspect of the present invention, multiple GP5-M heterodimers (glycantypes) may be needed to induce widespread protection against a variety of PRRSV strains.

Without wishing to be bound by this theory, the present inventors believe that all immunogens representing the various glycantypes of GP5 may need to be given together due to the concept of "original antigenic sin" (OAS) where the antibody response elicited in response to a second viral infection reacts more strongly than the original variant infection. Thus, the present inventors contemplate the pig's immune system can be primed with a single PAD or immunization with multiple PAD to obtain a broader and more reactive immune response than does immunization with a single PAD. The use of a multivalent vaccine strategy may circumvent original antigenic sin. Thus, according to the invention, multiple PRRSV strains or PAD may be administered simultaneously or sequentially. For treatment of PRRSV or inducement of protective antibody to all epitopes of PAD, pigs may require exposure to multiple GP5, M, or GP5-M heterodimer glycantypes.

In one embodiment of the invention, a method of identifying GP5-M heterodimers that elicit protection against PRRSV is provided. This method also includes fragments, derivatives, or homologs of the GP5 and M protein or GP5-M heterodimers. In one aspect, the method comprises administering to a test pig a first GP5-M heterodimer, where the GP5 has glycosylation at position 44 of the GP5 of a North American (NA) porcine reproductive and respiratory syndrome virus (PSSRV) or glycosylation at position 46 of the GP5 of a European (EU) PRRSV. The administration of the first GP5-M heterodimer to the test pig is followed by administration of a second GP5-M heterodimer, where the GP5 of the second GP5-M heterodimer does not have glycosylation at position 44 of GP5 of a North American (NA) PRRSV or at position 46 of the GP5 of a European (EU) PRRSV. The test and control pigs are subsequently challenged with an infectious amount of a virus that causes PRRS, for example, Lelystad. One skilled in the art would be familiar with the PRRS strains that cause PRRS and the route and dosage necessary to achieve infection. The method also includes determining whether the first and second administered GP5-M heterodimers are effective in protecting a pig against the challenge PRRSV.

Various methods and techniques for determining whether the GP5-M heterodimers provided protection against PRRSV infection are known to those skilled in the art, including but not limited to, observing a difference between the test and control pig in the symptoms of PRRS, for example, the clinical signs or symptoms of PRRS comprising weight loss, decreased weight gain, lethargy, respiratory distress, "thumping" (forced expiration), fevers, roughened haircoats, sneezing, coughing, eye edema, conjunctivitis, gross lesions microscopic lung lesions, myocarditis, lymphadenitis, encephalitis and rhinitis. A decrease in any of the symptoms of PRRS observed in the test pig compared to the control pig indicates that the first and second administered GP5-M heterodimers provide a degree of protection against PRRS. Similar symptoms or an increase in any of the symptoms of PRRS observed in the test pig compared to those observed in the control pig indicate that the first and second administered GP5-M heterodimers do not provide protection against PRRS.

In another aspect, determining whether the GP5-M heterodimers provided protection against PRRSV infection includes determining the presence or absence of challenge PRRSV in the test pig by electron microscopy or antibody or assays such as the fluorescent focusing neutralizing (FFN) test or Western blot assay for the heterodimer may be used to give an indication of heterologous antibody production and protection. The presence of the challenge PRRSV indicates that the first and second administered GP5-M heterodimers are not effective in protecting against PRRS and the absence of the challenge PRRSV indicates that the first and second administered GP5-M heterodimers are effective in protecting against PRRS.

The present inventors also contemplate that the GP5-M heterodimers of the present invention may be delivered using various vectors and viruses, for example, PRRSV. Thus, another aspect of the invention includes a method for identifying viruses that elicit protection against PRRSV. These identified GP5-M heterodimers or viruses may be used in an PRRSV immunization protocol or vaccine. For example, a PRRSV comprising a GP5-M heterodimer with N-glycosylation in the ectodomain of GP5, in particular a glycan at position 44 for a NA PRRSV or 46 for a EU PRRSV may be administered to a pig. The method also includes administering a NA or EU PRRSV strain having no glycosylated amino acids at position 44 or 46 in the GP5. To determine if the viruses provide protection a pig administered these "test" viruses may be challenged with a PRRSV, or any virus causing PRRS, and any PRRS symptoms observed and compared to a control pig that receive the challenge virus to determine if the "test" virus provides PRRSV protection.

In another aspect, a method of the invention includes identifying a virus or PAD that elicits protection against PRRSV for use in an immunization protocol or vaccine by administering fragments, derivatives, or homologs of GP5 having a glycan at position 44 for a NA PRRSV or 46 for a EU PRRSV as a heterodimer, for example, with a M protein of PRRSV followed by administering a GP5 heterodimer that has no glycosylated amino acids at position 44 or 46 in the GP5. To determine if the PADs provide protection a pig administered these "test" PAD may be challenged with a PRRSV, for example, Lelystad or any virus causing PRRS, and observing any PRRS symptoms and comparing the symptoms to a control pig that receive the challenge virus to determine if the "test" PADs provides PRRSV protection. Protection may also be determined using an incidence of morbidity and mortality.

The present inventors contemplate that any combination of killed (inactivated) PRRSV, attenuated (live modified) PRRSV, subunit, DNA, or recombinant vector based having a GP5, M, or GP5-M heterodimer may be glycantyped and used in the progressive or sequential or combinatorial immunization protocol or scheme described herein. In one aspect, the immunization protocol or scheme induces antibodies to the PAD.

The present inventors contemplate that European like PRRSV strains may be analogously glycantyped (Table 7) and used in an immunization protocol for pigs as described for the American like PRRSV.

According to the present invention, one embodiment of a PRRS vaccine includes an attenuated PRRSV with a GP5, M, or GP5-M heterodimer as described herein. The property of an attenuated strain to induce PRRS-associated disease conditions as described above are significantly reduced or completely absent if the strain is a live attenuated virus. Therefore, it is desirable that particular live PRRSV vaccines comprise an attenuated PRRSV strain that generates an immune response to the GP5, M, or heterodimer of GP5-M of the attenuated PRRSV strain without causing disease.

Methods for making attenuated viruses are well known in the art and include such methods as serial passage in cell culture on a suitable cell line or chemical mutagenesis. For example, attenuated variants of PRRSV may be produced by serial passage of the virus on a cell line, for example, Marc 145, CL2621, MA-104 cells, or porcine alveolar macrophages for between about 10 and 100 passages so that mutations accumulate that confer attenuation on the strain. Serial passaging refers to the infection of a cell line with a virus isolate, the recovery of the viral progeny from the host cells, and the subsequent infection of host cells with the viral progeny to generate the next passage. During passage on the cell line, the virus loses its ability to cause disease in the pig, e.g., becomes apathogenic or non-pathogenic, while maintaining its ability to replicate in the pig and produce a protective immune response.

Therefore, to make a vaccine, the attenuated PRRSV isolate is grown in cell culture on a suitable cell line, i.e., Marc 145, CL2621 or MA-104 cells, to titers sufficient for producing a vaccine. The PRRSV is harvested according to methods well known in the art. For example, the virus may be removed from cell culture and separated from cellular components, typically by well known clarification procedures, e.g., centrifugation, and may be further purified as desired using procedures well known to those skilled in the art. The PRRSV may then be concentrated, frozen, and stored at $-70°$ C. or freeze-dried and stored at $4°$ C.

The isolation of an attenuated virus may be followed by a sequence analysis of its genome to determine the basis for the attenuated phenotype. This is accomplished by sequencing the viral DNA and identifying nucleotide changes in the attenuated isolate relative to the genomic sequence of a control virus. Therefore, the molecular changes that confer attenuation on a virulent PRRSV strain can be characterized.

One embodiment of the invention provided herein, includes the introduction of sequence changes at any of the positions alone or in combination, in order to generate attenuated virus progeny in known PRRSV strains or those yet to be identified and isolated. Viral genomes with such alterations can be produced by any standard recombinant DNA techniques known to those skilled in the art (Ausubel et al., Current Protocols in Molecular Biology, Greene Publishing Associates & Wiley Interscience, New York, 1989) for introduction of nucleotide changes into cloned DNA. A genome may then be ligated into an appropriate vector for transfection into host cells for the production of viral progeny.

The PRRSV prior to vaccination is mixed to an appropriate dosage and may include a pharmaceutically acceptable carrier, such as a saline solution and/or an adjuvant, such as aluminum hydroxide. Thus, PRRSV vaccines of the invention may include an immunogenically effective amount of one or more attenuated PRRSV as described herein.

The attenuated virus composition may be introduced into a pig, with a physiologically acceptable vehicle and/or adjuvant. Useful vehicles are well known in the art, and include, e.g., water, buffered water, saline, glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

Administration of the live attenuated viruses disclosed herein may be carried out by any suitable means, including both parenteral injection (such as intraperitoneal, subcutaneous, or intramuscular injection), and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the virus as an aerosol suspension, and then causing the subject to inhale the respirable particles. Methods and apparatus for administering respirable particles of pharmaceutical formulations are well known, and any conventional technique can be employed. As a result of the vaccination the host becomes at least partially or completely immune to PRRSV infection of the serotypes administered, or resistant to developing moderate or severe PRRSV infection.

In another embodiment, the attenuated PRRSV of one particular strain having a desired PADs as described herein can be combined with attenuated viruses of other strains of PRRSV having the desired PADs as described herein to achieve protection against multiple PRRSV. According to the present invention, the different PRRSVs may be administered sequentially or progressively or alternately administered simultaneously in an admixture. Sequential or progressive administration of the vaccine compositions of the invention may be required to elicit sufficient levels of immunity to multiple PRRSV strains. Single or multiple administration of the vaccine compositions of the invention can be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection. The property of an attenuated strain to induce PRRS-associated disease conditions as described above are significantly reduced or completely absent if the strain is in an inactivated form.

According to the present invention, one embodiment of a PRRSV vaccine includes an inactivated (killed) PRRSV with a GP5, M, or GP5-M protein heterodimer. The property of an inactivated strain to induce PRRS-associated disease conditions as described above are significantly reduced or completely absent if the strain is inactivated (killed). Inactivation of a PRRSV strain may be accomplished by a variety of methods including freeze-thawing, chemical treatment (for example, treatment with thimerosal or formalin), sonication, radiation, heat or any other convention means sufficient to prevent replication or growth of the virus while maintaining the immunogenicity of the PRRSV strain.

The inactivated vaccine is made by methods well known in the art. For example, once the virus is propagated to high titers, it would be readily apparent by those skilled in the art that the virus antigenic mass could be obtained by methods well known in the art. For example, the PRRSV antigenic mass may be obtained by dilution, concentration, or extraction. The PRRSV may be inactivated by treatment with formalin or with binary ethyleneimine (BEI), both methods are well known to those skilled in the art. For example, inactivation of a PRRSV strain by formalin may be performed by mixing the PRRSV suspension with 37% formaldehyde to a final formaldehyde concentration of 0.05%. The PRRSV-formaldehyde mixture is mixed by constant stirring for approximately 24 hours at room temperature. The inactivated PRRSV mixture is then tested for residual live virus by assaying for growth on a suitable cell line, for example, Marc 145, CL2621 or MA-104 cells.

Inactivation of a PRRSV strain by BEI may be performed, for example, by mixing the PRRSV suspension of the present invention with 0.1 M BEI (2-bromo-ethylamine in 0.175 N NaOH) to a final BEI concentration of 1 mM. The PRRSV-BEI mixture is mixed by constant stirring for approximately 48 hours at room temperature, followed by the addition of 1.0 M sodium thiosulfate to a final concentration of 0.1 mM. Mixing is continued for an additional two hours. The inactivated PRRSV mixture is tested for residual live PRRSV by assaying for growth on a suitable cell line, for example, Marc 145 cells. The aforementioned inactivated PRRSV of the present invention may be mixed with any one of the pharmaceutically acceptable adjuvants or physiological carriers for formulating inactivated virus vaccines to the appropriate dosage level. Suitable formulations and modes of administration of the killed PRRSV vaccine are described below.

In one embodiment, a PRRSV vaccine of the present invention may be a subunit vaccine. In one aspect, the subunit is a GP5, M, or GP5-M heterodimer of PRRSV. Viral subunits may be obtained from PRRSV using biochemical methods or they can be expressed by recombinant means in suitable cells, for example, eukaryotic cells. Methods of expressing viral subunits are common in the art. For example, methods of expressing viral subunits are described in the following articles and in the references cited therein: Possee, 1986, Virus research 5:43; Kuroda et al., 1986, EMBO J. 5: 1359; Doerfler, 1986, Curr. Topics Microbiol. Immunol. 131:51; Rigby, 1983, J. Gen. Virol. 64:255; Mackett et al., 1985, In: DNA Cloning, A Practical Approach, Vol II, Ed. D. M. Glover, IRL Press, Washington, D.C.; Rothestein, 1985, In: DNA Cloning, A Practical Approach, Supra; Kinney et al., 1988, J. Gen. Virol. 69:3005; Panical et al., 1983, Proc. Natl. Acad. Sci. USA 80:5364; Small et al., 1985, In: Vaccinia Viruses as Vectors for Vaccine Antigens, pp. 175-178, Ed. J. Quinnan, Elsevier, N.Y.

In the practice of one embodiment of this invention, the GP5, M, or GP5-M heterodimer subunit may be produced in vitro by recombinant techniques in large quantities sufficient for use in a subunit vaccine.

In another aspect, the GP5, M, or GP5-M heterodimer subunit may be expressed by a recombinant vector, viral vector, or virus. In another aspect, the recombinant vector, viral vector, or virus expressing the subunit may itself serve as a vaccine component acting as a as an antigen or an adjuvant and eliciting or enhancing the pig's immune response to a GP5, M, or GP5-M protein heterodimer alone.

In a further embodiment of the present invention, the vaccine comprises a recombinant virus vector containing a nucleic acid encoding the antigen of a GP5, M, or GP5-M heterodimer or immunogenic fragment thereof from a PRRSV strain. Suitable recombinant virus vectors include but are not limited to live adenovirus, poxvirus, baculovirus, pseudorabies virus (PRV), Venezuelan equine encephalitis (VEE) vectors such as strains V3526 or TC-83, and viral replicon particles (VRPs) derived from VEE, equine arteritis virus (EAV), or transmissible gastroenteritis virus (TGE).

The recombinant virus of the present invention may also contain multiple copies of one glycantype of a GP5, M, or GP5-M heterodimer subunit. Alternatively, the recombinant virus may contain more than one GP5, M, or GP5-M heterodimer subunit glycantype, so that the virus may express two or more differing GP5, M, or GP5-M heterodimer subunits. In one aspect, the GP5, M, or GP5-M heterodimer subunits may vary in glycosylation of the ectodomain of the GP5 protein.

In the construction of the virus vector of the present invention, the GP5, M, or GP5-M protein heterodimer subunit sequence is preferably inserted in a viral strain under the control of an expression control sequence in the virus itself. The techniques employed to insert the GP5, M, or GP5-M heterodimer subunit sequence into the viral vector and make ether alterations in the viral DNA, e.g., to insert linker sequences and the like, are known to one of skill in the art. See, e.g., T. Maniatis et al, "Molecular Cloning. A Laboratory Manual", Cold Spring Harbor Laboratory, Cold Spring Harbor, N.Y. (1982). Thus, given the disclosures contained herein the construction of suitable virus expression vectors for expression of a GP5, M, or GP5-M heterodimer subunit protein is within the skill of the art. The recombinant virus itself, constructed as described above, may be used directly as a vaccine component. According to this embodiment of the invention, the recombinant virus, containing the GP5, M, or GP5-M heterodimer subunit, is introduced directly into the subject pig by vaccination. The recombinant virus, when introduced into a subject pig directly, infects the pig's cells and produces the GP5, M, or GP5-M heterodimer subunit in the pig's cells.

To make a recombinant virus vector that expresses the GP5, M, or GP5-M heterodimer antigen or immunogenic fragment thereof, a cDNA encoding the GP5, M, or GP5-M heterodimer antigen or immunogenic fragment thereof is inserted into the genome of a virus vector, for example, live adenovirus, poxvirus, baculovirus, pseudorabies virus (PRV), Venezuelan equine encephalitis (VEE) vectors such as strains V3526 or TC-83, and viral replicon particles (VRPs) derived from VEE, equine arteritis virus (EAV), or transmissible gastroenteritis virus (TGE). Recombinant viral vectors can be produced by any standard recombinant DNA techniques known to those skilled in the art (Ausubel et al., Current Protocols in Molecular Biology, Greene Publishing Associates & Wiley Interscience, New York, 1989) for introduction of nucleotide changes into cloned DNA. A viral genome may then be ligated into an appropriate vector for transfection into host cells for the production of viral progeny.

For any of the aforementioned recombinant virus vectors, the cDNA encoding the GP5, M, or GP5-M heterodimer antigen or immunogenic fragment thereof is operably linked to a eukaryote promoter at the 5' end of the cDNA encoding the antigen and an eukaryote termination signal and poly(A) signal at the 3' end of the cDNA encoding the antigen. As used herein, the term "operably linked" means that the polynucleotide of the present invention (as a cDNA molecule) and a polynucleotide (DNA) containing an expression control sequence, e.g., transcription promoter and termination sequences, are situated in a vector or cell such that expression of the antigen encoded by the cDNA is regulated by the expression control sequence. Methods for cloning DNA such as the cDNA encoding the GP5, M, or GP5-M heterodimer antigen or immunogenic fragment thereof and operably linking DNA containing expression control sequences thereto are well known in the art. Examples of promoters suitable for expressing the GP5, M, or GP5-M heterodimer antigen or immunogenic fragment thereof in the recombinant virus vectors are the cytomegalovirus immediate-early (CMV) promoter, the Rous sarcoma virus long terminal repeat (RSV-LTR) promoter, the simian virus 40 (SV40) immediate-early promoter, and inducible promoters such as the metallothionein promoter. An example of a DNA having a termination and poly(A) signal is the SV40 late poly(A) region. Another example of a viral expression system suitable for producing the antigen is the Sindbis Expression system available from Invitrogen. The use of these commercially available expression vectors and systems are well known in the art.

In an embodiment further still of the present invention, the vaccine is provided as a nucleic acid or DNA molecule vaccine that elicits an active immune response in the pig. The DNA molecule vaccine consists of DNA having a nucleic acid sequence which encodes the GP5, M, or GP5-M heterodimer antigenic determinant or immunogenic fragment thereof. The nucleic acid encoding the GP5, M, or GP5-M heterodimer antigenic determinant or immunogenic fragment thereof is operably linked at or near the start codon for the GP5, M, or GP5-M heterodimer antigenic determinant to a promoter that enables transcription of the GP5, M, or GP5-M heterodimer antigenic determinant or immunogenic fragment thereof from the nucleic acid when the nucleic acid is inoculated into the cells of the pig. Preferably, the DNA molecule is in a plasmid. Promoters that are useful for DNA vaccines are well known in the art and include, but are not limited to, the RSV LTR promoter, the CMV immediate early promoter, and the SV40 T antigen promoter. In one aspect, the nucleic acid be operably linked at or near the termination codon of the sequence encoding the GP5, M, or GP5-M heterodimer antigenic determinant or immunogenic fragment thereof to a nucleic acid fragment comprising a transcription termination signal and poly(A) recognition signal. The DNA vaccine is provided to the pig in an accepted pharmaceutical carrier or in a lipid or liposome carrier similar to those disclosed in U.S. Pat. No. 5,703,055 to Felgner. The DNA vaccine can be provided to the pig by a variety of methods such as intramuscular injection, intrajet injection, or biolistic bombardment. Making DNA vaccines and methods for their use are provided in U.S. Pat. Nos. 5,589,466 and 5,580,859, both to Felgner. Finally, a method for producing pharmaceutical grade plasmid DNA is taught in U.S. Pat. No. 5,561,064 to Marquet et al.

Therefore, using any suitable methods including those mentioned above, DNA vaccines that express the GP5, M, or GP5-M heterodimer antigen or immunogenic fragment thereof are used to immunize pigs against PRRSV. The advantage of the DNA vaccine is that the DNA molecule is conveniently propagated as a plasmid which is a simple and inexpensive means for producing a vaccine, and since the vaccine is not live, many of the regulatory issues associated with live recombinant virus vector vaccines are not an issue with DNA vaccines. One skilled in the art would appreciate that the DNA vaccine of the present invention can comprise synthetically produced nucleic acids which are made by chemical synthesis methods well known in the art.

In an embodiment further still of the present invention, the vaccine consists of the isolated and purified GP5, M, or GP5-M heterodimer antigen or immunogenic fragment thereof. Preferably, the GP5, M, or GP5-M heterodimer antigen or immunogenic fragment thereof is produced in a recombinant bacterium or eukaryote expression vector which produces the antigen which is isolated and purified to make the vaccine. For example, the GP5, M, or GP5-M heterodimer antigen or immunogenic fragment thereof is produced in a microorganism such as bacteria, yeast, or fungi; in a eukaryote cell such as a mammalian or an insect cell; or, in a recombinant virus vector such as adenovirus, poxvirus, herpesvirus, Simliki forest virus, baculovirus, bacteriophage, sindbis virus, sendai virus, live Venezuelan equine encephalitis (VEE) vectors such as strains V3526 or TC-83, and viral replicon particles (VRPs) derived from VEE, equine arteritis virus (EAV), or transmissible gastroenteritis virus (TGE). Suitable bacteria for producing the GP5, M, or GP5-M heterodimer antigen or immunogenic fragment thereof include *Escherichia coli, Bacillus subtilis*, or any other bacterium that is capable of expressing heterologous polypeptides. Suitable yeast types for expressing the GP5, M, or GP5-M heterodimer antigen or immunogenic fragment thereof include *Saccharomyces cerevisiae, Schizosaccharomyces pombe, Candida*, or any other yeast capable of expressing heterologous polypeptides. Methods for using the aforementioned bacteria, recombinant virus vectors, eukaryote cells to produce antigens for vaccines are well known in the art.

To produce the vaccine consisting of the GP5, M, or GP5-M heterodimer antigen or immunogenic fragment thereof, the nucleic acid encoding the GP5, M, or GP5-M heterodimer antigen or immunogenic fragment thereof is in a plasmid and the nucleic acid is operably linked to a promoter which effects the expression of the GP5, M, or GP5-M heterodimer antigen or immunogenic fragment thereof in a microorganism. Suitable promoters include, but are not limited to, T7 phage promoter, T3 phage promoter, beta-galactosidase promoter, and the Sp6 phage promoter. Expression of the GP5, M, or GP5-M heterodimer antigenic determinant or immunogenic fragment thereof in a microorganism enables the GP5, M, or GP5-M heterodimer antigenic determinant to be produced using fermentation technologies which are used commercially for producing large quantities of recombinant antigenic polypeptides. Methods for isolating and purifying antigens are well known in the art and include methods such as gel filtration, affinity chromatography, ion exchange chromatography, or centrifugation.

To facilitate isolation of the GP5, M, or GP5-M heterodimer antigenic determinant or immunogenic fragment thereof, a fusion polypeptide may be made wherein the GP5, M, or GP5-M heterodimer or immunogenic fragment thereof is linked to another polypeptide which enables isolation by affinity chromatography. Preferably, a fusion polypeptide is made using one of the expression systems infra For example, the cDNA nucleic acid sequence encoding the GP5, M, or GP5-M heterodimer antigenic determinant or immunogenic fragment thereof is linked at either the 5' end or 3' end to a nucleic acid encoding a polypeptide. The nucleic acids are linked in the proper codon reading frame to enable production of a fusion polypeptide wherein the amino and/or carboxyl terminus of the GP5, M, or GP5-M heterodimer antigenic determinant or portion thereof is fused to a polypeptide which allows for the simplified recovery of the antigen as a fusion polypeptide.

An example of a prokaryote expression system for producing the GP5, M, or GP5-M heterodimer antigenic determinant or immunogenic fragment thereof for use in vaccines is the Glutathione S-transferase (GST) Gene Fusion System available from Amersham Pharmacia Biotech, Piscataway, N.J., which uses the pGEX-4T-1 expression vector plasmid. The cDNA encoding the GP5, M, or GP5-M heterodimer antigenic determinant or immunogenic fragment thereof is fused in the proper codon reading frame with the DNA encoding GST. The GST part of the fusion polypeptide allows the rapid purification of the fusion polypeptide using glutathione Sepharose 4B affinity chromatography. After purification, the GST portion of the fusion polypeptide can be removed by cleavage with a site-specific protease such as thrombin or factor Xa to produce an antigenic determinant free of the GST polypeptide. The GP5, M, or GP5-M heterodimer antigenic determinant or immunogenic fragment thereof free of the GST polypeptide is produced by a second round of glutathione Sepharose 4B affinity chromatography.

Another method for producing a vaccine comprising the GP5, M, or GP5-M heterodimer antigenic determinant or immunogenic fragment thereof is a method which links in-frame with the cDNA encoding the antigenic determinant, DNA codons that encode polyhistidine. The polyhistidine preferably comprises six histidine residues which allows purification of the fusion polypeptide by metal affinity chromatography, preferably nickel affinity chromatography. To produce the GP5, M, or GP5-M heterodimer antigenic determinant or immunogenic fragment thereof free of the polyhistidine, a cleavage site such as an enterokinase cleavage site is fused in the proper reading frame between the codons encoding the polyhistidine and the codons encoding the antigen. The antigen free of the polyhistidine is made by removing the polyhistidine by cleavage with enterokinase. The antigen free of the polyhistidine is produced by a second round of metal affinity chromatography which binds the free polyhistidine. See Motin et al. Infect. Immun. 64: 4313-4318 (1996). The Xpress System, available from Invitrogen, Carlsbad, Calif., is an example of a commercial kit which is available for making and then isolating polyhistidine-polypeptide fusion protein.

Immunogenic compositions including vaccines may be prepared in a variety of formulations, for example, injectibles, liquid solutions or emulsions. The immunogens, for example, GP5, M, or GP5-M protein heterodimer may be mixed with pharmaceutically acceptable excipients which are compatible with the immunogens. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

Immunogenic compositions and vaccines may be administered parenterally, by injection subcutaneously or intramuscularly or in any other suitable manner. The immunogenic preparations and vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner. However, suitable dosage ranges are readily determinable by one skilled in the art and may be of the order of micrograms of the immunogens. Suitable regimes for initial administration and booster doses are also variable, but may include an initial administration followed by subsequent administrations. The dosage may also depend on the route of administration and will vary according to the size of the host.

The concentration of the immunogens in an immunogenic composition according to the invention is in general about 1 to about 95%. Immunogenicity can be significantly improved if the antigens are co-administered with adjuvants, commonly used as 0.005 to 0.5 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. The vaccines of the present invention may be used in conjunction with an adjuvants, for example, lipopolysaccharides, aluminum hydroxide and aluminum phosphate (alum), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. Desirable characteristics of ideal adjuvants include: (1) lack of toxicity; (2) ability to stimulate a long-lasting immune response; (3) simplicity of manufacture and stability in long-term storage; (4) ability to elicit both CMI and HIR to antigens administered by various routes; (5) synergy with other adjuvants; (6) capability of selectively interacting with populations of antigen presenting cells (APC); (7) ability to specifically elicit appropriate T-cell helper 1 (TH 1) or TH 2 cell-specific immune responses; and (8) ability to selectively increase appropriate antibody isotype levels (for example, IgA) against antigens. An adjuvant used with the present invention need not possess all these characteristics to be used with the present invention.

The route of administration for any one of the embodiments of the vaccine of the present invention includes, but is not limited to, oronasal, intramuscular, intraperitoneal, intradermal, subcutaneous, intravenous, intraarterial, intraocular, and oral as well as transdermal or by inhalation or suppository. The vaccine can be administered by any means which includes, but is not limited to, syringes, nebulizers, misters, needleless injection devices, or microprojectile bombardment gene guns (Biolistic bombardment).

In one aspect of the invention, when the vaccine is subunit, DNA or recombinant based, the present inventors contemplate that it may be possible to use a single M protein and vary only the GP5 protein, for example, its glycantype, and still obtain protection against PRRSV.

Alternatively, more than one glycan type of GP5, M, or GP5-M heterodimer of PRRSV may be employed in a vaccine according to the teachings of the present invention. This includes GP5, M, or GP5-M heterodimers from differing PRRSV as well as multiple copies of the same or similar GP5, M, or GP5-M heterodimer according to glycantyping. The present inventor contemplates that any vaccine for treating PRRS of the present invention may further include at least one other vaccine to a pig pathogen, for example, swine influenza virus (SIV), porcine circovirus (PCV), *Mycoplasma hyopneumoniae*, or *Haemophilus parasuis*.

As one measure of vaccine potency, an ELISA can be performed on a sample collected from an individual vaccinated to determine whether antibodies to a vaccine comprising a PAD polypeptide, a derivative, a homologue or a variant or fragment thereof generated anti-PAD antibodies. The individual's sample is measured against a reference anti-PAD antibody.

The present vaccine's potency may also be measured by determining whether the vaccination protects a pig against infection by PRRSV. A vaccine protects a pig against infection by a PRRSV if, after administration of the vaccine to one or more unaffected pigs, a subsequent challenge with a biologically pure virus isolate (e.g., VR 2385, VR 2386, or other virus isolate described below) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 1-4 weeks), challenging with a large sample ($10^{3-7}$ TCID$_{50}$) of a biologically pure PRRSV isolate. A blood sample is then drawn from the challenged pig after about one week, and an attempt to isolate the virus from the blood sample is then performed. Isolation of the virus is an indication that the vaccine may not be effective, and failure to isolate the virus is an indication that the vaccine may be effective.

Thus, the effectiveness of the present vaccine may also be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoperoxidase assay method, etc.). The symptoms of the porcine reproductive and respiratory disease may be evaluated quantitatively (e.g., temperature/fever), semi-quantitatively (e.g., severity of respiratory distress, or qualitatively (e.g., the presence or absence of one or more symptoms or a reduction in severity of one or more symptoms, such as cyanosis, pneumonia, heart and/or brain lesions, etc.).

Thus, the present invention also provides a method for vaccinating a susceptible host, for example, a pig, to PRRSV comprising administering to the host a PAD polypeptide, a derivative, a homologue or a variant or a fragment thereof in an amount effective for protecting against PRRSV infection. It will also be recognized by one of ordinary skill in the art that nucleic acids expressing a PAD polypeptide, a derivative, a homologue or a variant or a fragment thereof may also be used in vaccination. In another embodiment, a method for preventing or treating PRRSV in an animal is provided wherein a therapeutically effective amount of a vaccine, PAD polypeptides or nucleic acids encoding PAD, as described above, is administered to said animal. In one aspect, the animal is a pig.

The present invention also contemplates that a novel PAD polypeptide, a derivative, a homologue or a variant or a fragment thereof or nucleic acids encoding PAD polypeptides of this invention, either alone or with other immunogenic polypeptides, may be administered to an animal, for example, a pig, using any number of delivery systems or methods. These include but are not limited to a liposome delivery system, naked delivery system, electroporation, viruses, vectors, viral vectors, or an ingestible delivery system wherein the PAD polypeptide or nucleic acids encoding PAD are consumed, for example, in feed or water. Moreover, the PAD polypeptides, derivative, a homologue or a variant or fragment thereof or nucleic acids encoding PAD polypeptides may be administered (or formulated for administration) peritoneally, orally, intranasally, subcutaneously, intradermally, intramuscularly, topically or intravenously, but may be administered or formulated for administration by any pharmaceutically effective route (i.e., effective to produce immunity). In another aspect, the method further comprises the PAD polypeptide, a derivative, a homologue or a variant or fragment thereof or nucleic acids encoding a PAD polypeptide being present in a physiologically-acceptable carrier in an amount effective for protecting against PRRSV infection.

In addition to use as vaccines, the PAD polypeptides and nucleic acids encoding PAD polypeptides disclosed herein are available for use as antigens to generate the production of antibodies for use in passive immunotherapy, for use as diagnostic reagents, and for use as reagents in other processes such as affinity chromatography.

According to a still related aspect, the invention also includes so-called "passive immunization" methods for preventing or treating PRRSV. For example, an antiserum comprising antibodies produced by immunizing a heterologous host with PRRSV or mutant thereof, or immunogenic fragment thereof, is used for the therapeutic treatment of a PRRSV-infected pig. However, even vaccines which provide active immunity, i.e., vaccines comprising PRRSV or mutants thereof, or immunogenic fragments thereof, have been shown in certain cases to be effective when given as a therapeutic treatment against various diseases. Thus, the immunity that is provided by the present invention can be either active immunity or passive immunity and the intended use of the vaccine and antiserum can be either prophylactic or therapeutic.

According to this aspect of the invention, animal subjects, e.g. pigs, are given an effective dosage of an antibody that specifically binds to a PAD polypeptide, a derivative, a homologue or a variant or fragment thereof of the present invention. According to a related embodiment, such methods and compositions may include combinations of antibodies that bind at least one or more PAD polypeptides. The antibodies may also be administered with a carrier, as described herein. In general, in accordance with this aspect of the invention, such antibodies, will be administered (or formulated for administration) peritoneally, orally, intranasally, subcutaneously, intramuscularly, topically or intravenously, but can be administered or formulated for administration by any pharmaceutically effective route (i.e., effective to produce the indicated therapeutic levels). Thus, among others, antibodies against PRRSV may be employed to inhibit and/or treat PRRSV infections.

The invention further relates to diagnostic and pharmaceutical kits comprising one or more containers filled with one or more of the ingredients of the aforementioned compositions of the invention, for example, nucleic acids encoding a PAD polypeptide, a PAD polypeptide, a derivative, a homologue or a variant or fragment thereof, or an antibody directed towards a PAD polypeptide, a derivative, a homologue or a variant or a fragment thereof or a vaccine including a PAD polypeptide or a nucleic acid encoding a PAD polypeptide. Thus, the polynucleotides, polypeptides, and antibodies, and vaccines of the present invention may be employed as research reagents and materials for treatments of and diagnostics for PRRSV. In particular, it is contemplated that the kits may be used to determine whether a pig was successfully vaccinated so that antibodies directed towards PAD are present in the collected sample. For example, a biological sample from an animal, e.g. a pig, vaccinated with a PAD polypeptide described above is collected and incubated with a PAD polypeptide or other anti-PAD antibody preparation for a time sufficient for antibody binding to take place. The antibody binding to the PAD polypeptide or other anti-PAD antibody preparation is detected using methods known to one of ordinary skill in the art, for example Western Blot analysis and/or ELISA assays.

The anti-PAD antibodies of the invention have various utilities. For example, anti-PAD antibodies may be used in diagnostic assays for PRRSV, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases (Zola, *Monoclonal Antibodies: A Manual of Techniques*, CRC Press, Inc. (1987) pp. 147-158). The antibodies used in the diagnostic assays can be labeled with a detectable moiety. Detection of an antibody of the present invention can be facilitated by coupling (i.e., physically linking) the antibody to a detectable moiety. Examples of detectable moieties include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $I^{125}$, $I^{131}$, $S^{35}$ or $H^3$. The detectable moiety should be capable of producing, either directly or indirectly, a detectable signal. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982). The present inventors contemplate that such diagnostic kits would be of value in eradication programs for PRRSV at multiple levels, including but not limited to an individual (farm), regional, and/or national level.

Anti-PAD antibodies also are useful for the affinity purification of PAD from recombinant cell culture or natural sources. In this process, the antibodies against PAD are immobilized on a suitable support, such a Sephadex resin or filter paper, using methods well known in the art. The immobilized antibody then is contacted with a sample containing the PAD to be purified, and thereafter the support is washed with a suitable solvent that will remove substantially all the material in the sample except the PAD, which is bound to the immobilized antibody. Finally, the support is washed with another suitable solvent that will release the PAD from the antibody.

While the invention has been described with reference to PAD polypeptides, it is to be understood that this covers a derivative, a homologue or a variant or fragment thereof and similar proteins with additions, deletions or substitutions which do not substantially affect the protective antigenic properties of the recombinant protein.

The vaccine composition containing the attenuated PRRSV of the invention are administered to a pig susceptible to or otherwise at risk of PRRSV infection to enhance the pig's own immune response capabilities. Such an amount is defined to be an "immunogenically effective dose". In this use, the precise amount again depends on the pig's state of health and weight, the mode of administration, the nature of the formulation, etc. Vaccine compositions may further incorporate additional substances to stabilize pH, or to function as adjuvants, wetting agents, or emulsifying agents, which can serve to improve the effectiveness of the vaccine. Vaccines are generally formulated for parenteral administration and are injected either subcutaneously or intramuscularly. Such vaccines can also be formulated as suppositories or for oral administration, using methods known in the art.

The amount of vaccine sufficient to confer immunity to PRRSV is determined by methods well known to those skilled in the art. This quantity will be determined based upon the characteristics of the vaccine recipient and the level of immunity required. Typically, the amount of vaccine or dosage to be administered will be determined based upon the judgment of a skilled veterinarian or can be readily determined by routine experimentation. The amount of virus vaccine of each strain may be adjusted, i.e. increased or decreased, to result in a formulation which provides sufficient protection from infection with the desired PRRSV. The present inventors contemplate that different strains may be combined in any amount determined to be effective in preventing or treating PRRSV infection of a strain in the vaccine formulation, and possibly other strains if crossprotection occurs. Cross-protection to infection by other PRRSV strains my depend on the order in which PRRSV strains are administered or whether the pig has been subjected to a prior PRRSV infection as described above.

According to the present invention, the different PRRSV or PADs of PRRSV of the invention, for example, PADs of GP5, M, and/or GP5-M heterodimer with the same or varying glycosylation patterns in the GP5 ectodomain, may be administered sequentially or progressively or alternately administered simultaneously in an admixture. Sequential or progressive administration of the vaccine compositions of the invention may be required to elicit sufficient levels of immunity to multiple PRRSV strains. Single or multiple administration of the vaccine compositions of the invention can be carried out. Multiple administration may be required to elicit sufficient levels of immunity. Levels of induced immunity can be monitored by measuring amount of neutralizing secretory and serum antibodies, and dosages adjusted or vaccinations repeated as necessary to maintain desired levels of protection.

In one aspect of the immunization protocol against a PPRSV infection, a virus having a PAD of a GP5-M heterodimer of PRRSV of the present invention with glycosylation at position 44 of GP5 in a North American strain is administered, followed by administration of a virus having a PAD of a GP5-M heterodimer of PRRSV of the present invention without glycosylation at position 44 of GP5 in a North American strain, and then challenged with a PRRSV having glycosylation in the neutralizing epitope of GP5.

In another aspect, a virus having a PAD of a GP5-M heterodimer of PRRSV of the present invention with glycosylation at position 46 in GP5 in a European strain is administered, followed by administration of a virus having a PAD of a GP5-M heterodimer of PRRSV of the present invention without glycosylation at position 46 in GP5 in a European strain, and then challenged with a PRRSV having glycosylation in the neutralizing epitope of GP5.

In one aspect of the immunization protocol against a PPRSV infection, a PAD comprising a GP5-M heterodimer of PRRSV of the present invention with glycosylation at position 44 of GP5 in a North American strain is administered, followed by administration of a PAD comprising a GP5-M heterodimer of PRRSV of the present invention without glycosylation at position 44 of GP5 in a North American strain, and then challenged with a strain of PRRSV having glycosylation in the neutralizing epitope of GP5. In another aspect, a PAD comprising a GP5-M heterodimer of PRRSV of the present invention with glycosylation at position 46 of a GP5 in a European strain is administered, followed by administration of a PAD comprising a GP5-M heterodimer of PRRSV of the present invention without glycosylation at position 46 of GP5 in a European strain, and then challenged with a strain of PRRSV having glycosylation in the neutralizing epitope of GP5.

In one embodiment of the invention, a PAD of GP5 may have no glycans from amino acids 1-35 in the NA PRRSV GP5 protein. In another aspect, a PAD of GP5 may have a glycan at position 44 in the NA PRRSV GP5 protein. In another aspect, a PAD of GP5 may have a glycan at position 44 in the NA PRRSV GP5 and have glycans present or absent in amino acids 1-35 in the NA PRRSV GP5 protein, for example, as found in some NA PRRSV strains.

In one embodiment of the invention, a PAD of GP5-M heterodimer may have no glycans from amino acids 1-35 in the NA PRRSV GP5 protein. In another aspect, a PAD of GP5-M heterodimer may have a glycan at position 44 in the NA PRRSV GP5 protein. In another aspect, a PAD of GP5-M heterodimer may have a glycan at position 44 in the NA PRRSV GP5 and have glycans present or absent in amino acids 1-35 in the NA PRRSV GP5 protein, for example, as found in some NA PRRSV strains.

In one embodiment of the invention, a PAD of GP5 may have no glycans from amino acids 1-37 in the EU PRRSV GP5 protein, as found in Lelystad. In another aspect, a PAD of GP5 may have a glycan at position 46 in the EU PRRSV GP5 protein. In another aspect, a PAD of GP5 may have a glycan at position 46 in the EU PRRSV GP5 and have glycans present or absent in amino acids 1-37 in the EU PRRSV GP5 protein, for example, as found in some EU PRRSV strains.

In one embodiment of the invention, a PAD of GP5-M heterodimer may have no glycans from amino acids 1-37 in the EU PRRSV GP5 protein, as found in Lelystad. In another aspect, a PAD of GP5-M heterodimer may have a glycan at position 46 in the EU PRRSV GP5 protein. In another aspect, a PAD of GP5-M heterodimer may have a glycan at position 46 in the EU PRRSV GP5 and have glycans present or absent in amino acids 1-37 in the EU PRRSV GP5 protein, for example, as found in some EU PRRSV strains.

EXAMPLES

Example 1

The solution to identification of the PAD of PRRSV was not obvious because others have not synthesized the information concerning North American and European strains of PRRSV and Equine Arteritis Virus (EAV) into knowledge. For example, the modified live vaccine (MLV) for EAV is very efficacious while the MLV for PRRSV is not. Thus many scientists apparently have concluded that a comparison of the similarities and differences between the two viruses would not be of value regarding the development of a vaccine for PRRSV. Beginning in early February 2005, the inventors studied numerous publications, synthesized the various important information, and by deductive reasoning identified the protective antigenic determinants of PRRSV as the Matrix-Glycoprotein 5 (M-GP5) heterodimer.

One of the most interesting and puzzling aspects of PRRS epidemiology is the variation between North American and European isolates and the fact that at least before introduction of PRRSV live vaccine into Europe from the U.S., PRRS was relatively mild disease in western Europe. In addition, in some small traditional U.S. farms, the PRRSV spontaneously disappears for no apparent reason. Whereas in the U.S., PRRS has always caused more devastating economic losses (especially in large herds). For this reason the inventors compared the N-Glycosylation sites on VR2332 (the common N. American strain) and Lelystad virus (the common European strain) See Table 1. Please note the similarity of HLV013 and Lelystad virus; however, these 2 viruses are not identical in that the GP5 signal sequence and hypervariable regions of GP5 are very different. According to publications, there is evidence that live Lelystad virus may protect pigs against PRRS to a higher degree than VR 2332. The lack of glycosylation at AA 1-43 is the reason that PRRS has been less severe in part of Europe and in some farms in the U.S. That is, Lelystad virus has been naturally immunizing pigs in Europe and strains similar to HLV013 have been doing the same on a limited number of farms in the U.S. The fact that N. American strains VR2332 and Mn184 are quite different regarding glycosylation led us to compare antibody reactivity of VR2332 and Leylstad strains (Table 2). Since antibody to the Lelystad virus reacts with the GP5-M heterodimer of Lelystad we hypothesized that the GP5-M heterodimer contains the protective antigenic determinants of PRRSV and could be the basis for resistance to the PRRS.

TABLE 1

Comparison of AA sequence and N-glycosylation of various PRRSV strains

| N-Glycosylation Sites | VR 2332* | HLV092 | HLV013 | Lelystad | HLV093 | HLV094 |
|---|---|---|---|---|---|---|
| 1-43 or 45 | + | + | − | − | + | + |
| 44 or 46 | + | + | + | + | − | + |
| 51 or 53 | + | + | + | + | + | − |

*Ingelvac MLV, Ingelvac ATP, and PrimePac MLV all similar to VR2332

TABLE 2

Comparison of the antibody reactivity of VR2332 and Leystad strains by Western Blot

| Sera from infected pigs with | Nucleocapsid | | Matrix | | GP5 | | GP5-M Heterodimer | |
|---|---|---|---|---|---|---|---|---|
| | VR | L | VR | L | VR | L | VR | L |
| Ab to VR2332 (VR) | + | + | + | + | − | − | ?* | ? |
| Ab to Lelystad (L) | + | + | + | + | −** | + | ? | + |

* ? indicates that the result has not been published
** Positive by peptide ELISA

TABLE 3

Comparison of PRRSV and EAV with regard to deducing the protective antigenic determinants of PRRSV

| Characteristics | PRRSV | EAV |
|---|---|---|
| Host | Swine | Equine |
| Cultivatable in vitro | Yes | Yes |
| GP5 main virus neutralizing (VN) epitope | Yes | Yes |
| Antibody to GP5 induces immunity | No | No |
| Weak VN activity on nucleocapsid (N) and matrix (M) | Yes | Yes |
| Antibody to N, M, and other GPs induces immunity | No | No |
| Modified live vaccine (MLV) induces immunity to all strains of the virus | No | Yes |
| MLV induces antibody to N of all strains | Yes | No* |
| MLV induces antibody to M of all strains | Yes | Yes |
| MLV induces antibody to GP5 of all strains | No | Yes |
| MLV induces antibody to M-GP5 heterodimer of all strains | ?** | Yes |
| Antibody to GP5-M heterodimer protects against disease | ?** | Yes |
| M-GP5 heterodimer has been synthesized | No | Yes |
| Heparin receptor on M | Yes | ? |
| Sialic acid on GP5 | Yes | ? |
| N-glycosylation of asparagines on signal sequence and hypervariable regions which are to the left of the conserved VN epitope of the AA sequence of the GP-5 protein | Yes | No |
| N-glycosylation of asparagines on the conserved VN epitope of the AA sequence of the GP-5 protein | Yes | Yes |
| A cysteine residue is in the AA sequence of the GP-5 protein | Yes | Yes |
| M and GP-5 are connected by a disulfide bond | Yes | Yes |

*The horse appears not to respond to the nucleocapsid of EAV; males which carry the virus in their testes may have antibodies to N.
**Has not been published
†Since EAV has no N-glycosylation sites to the left of the VN conserved epitope, the GP5-M heterodimer contains the protective antigenic determinants of PRRS by deductive reasoning.

Note that GP5 in PRRSV is synonymous with the envelope protein $G_L$ in EAV. By synthesis and deduction, the identification of protective antigenic determinants (PAD) were identified. The PAD of PRRSV are the antigens associated with the GP5-M heterodimer and thus the basis of this disclosure. Plagemann, Faaberg, and Osorio have been focused simply on the virus neutralizing (VN) aspects of PRRSV associated the inventors were aware that the MLV vaccine for EAV was quite efficacious. Therefore the inventors compared the various immunological and genomic aspects of PRRSV to EAV (Table 3).

with GP5 protein. But antibodies are not simply virus neutralizing, thus in PRRSV protection, antibodies interfere with the heparin receptor on the matrix protein and the sialic acid component of GP5 which prevent attachment and entry into porcine alveolar macrophages (Table 3). The concept of antibody inhibition in this disclosure is not virus neutralization per se. In summary, Strains Lelystad and HLV013 of PRRSV have no glycans at residues 1-43 amino acids (AA) (in the signal sequence or the hypervariable region upstream of the conserved neutralizing epitope)

Antibodies to virulent and vaccine viruses of PRRSV do not react with the GP5-M heterodimer of all PRRSV isolates because of the presence of glycans at 1-43 AA The glycans at 1-43 AA of the PRRSV on GP5 are the decoy epitope A (Osorio) and the excess glycans (Plagemann) but these workers believe the decoy glycans only interfere with the production of virus neutralizing (VN) antibodies against the conserved region in GP5 (they make no mention of the importance of matrix protein).

In reality, the decoy glycans interfere with the production of antibodies to the GP5-M heterodimer rather than just interference with the production of VN antibodies to GP5. Antibodies to GP5-M heterodimer prevent the attachment and entry of PRRSV to porcine alveolar macrophages (not just virus neutralization). Antibodies are only induced by live PRRSV if AA 1-43 are devoid of glycans thus the reason current MLV PRRSV vaccines are ineffective.

PRRSV researchers have focused on the classical approaches to developing vaccines for viruses which involve mechanisms associated with either cell mediated immunity (CMI) and/or virus neutralizing (VN) antibodies. Plagemann, Faaberg, and Osorio have identified a conserved epitope on GP5 which is associated with VN antibodies. However, antibodies to GP5 conserved epitope alone do not induce sufficient protective antibodies to PRRSV. Plagemann and Faaberg have suggested that the glycans on GP5 may interfere with the production of VN antibodies and Osorio has suggested that a decoy epitope prevents the production of VN antibodies. Osorio has injected sows with serum containing VN antibodies and protected their piglets against PRRSV; however, when young piglets were injected with the antibody preparation, they were not protected. Young piglets were not protected because Osorio's antiserum lacked a complete set of antibodies to PAD (all the viruses used by Osorio to induce VN antibodies contained glycans in AA 1-43 of GP5). Thus, the antibodies to PAD are very different than the VN antibodies directed towards the GP5 protein only.

Murtaugh has evidence that VN antibodies are not involved in elimination of the virus in naturally affected pigs and favors a mechanism involving CMI. Murtaugh stated at a recent meeting in Toronto (5 Mar. 2005) that the protective determinants of PRRSV have not been described. Publications by these experts and others in PRRSV research (attached) have repeatedly stated that PRRSV is unique virus that produces some resistance to homologous virus and very little protection to heterologous virus challenge and that CMI and VN responses are slow to develop and are not necessarily associated with resistance to the virus. What has not been obvious to other scientists is that the PAD are a combination of the conserved region of the GP5 protein attached to the matrix in a heterodimer form. Furthermore, the GP5 protein must not contain N-glycosylated asparagines between amino acids 1-43. It has been published that the matrix protein (heparin receptors) is involved in virus attachment to porcine alveolar macrophages (PAM) of the pig and that the GP5 protein contains sialic acid residues which allow entry to PAM. Thus, antibodies to PAD (GP5-M heterodimer) prevents PRRSV attachment and entry rather than just performing virus neutralization. Currently available vaccines do not produce antibodies to PAD of the PRRSV.

Example 2

Figure 3:
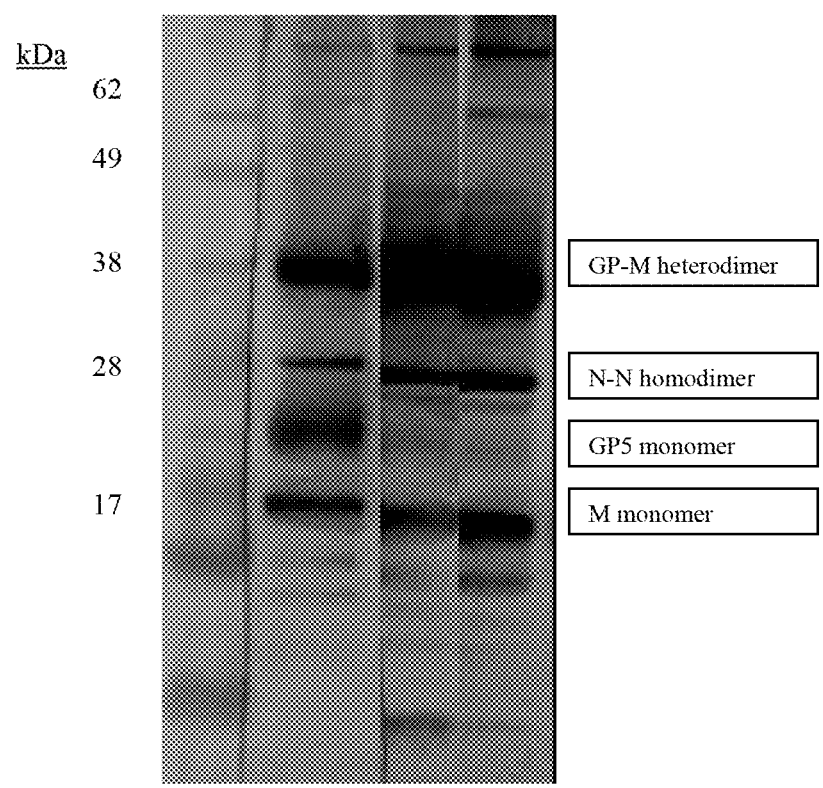
FIG. 3: Non-reduced western blot of different serum samples from pig after live PRRSV inoculation. As the neutralizing antibody (FFN) titers increase, so does the intensity of antibody reaction to the GP-M heterodimer indicating the protective role of GP-M specific antibodies. The intensity of the antibody reaction to GP5 monomer however decreases. A very slight increase in reaction density can also be seen for N—N homodimer and Matrix monomer however previous studies have shown that antibodies specific for these proteins are not protective. Lane 1—ladder, Lane 2—neut titer=256, Lane 3—neut titer=1024, Lane 4—neut titer=2048.

Recent work in our lab showed that a live strain of PRRSV (FIG. 2, Strain HLV013) lacking the glycans prior to amino acid 44 of GP5 would induce high titers to the GP neutralizing epitope as determined by a neutralizing peptide ELISA assay. Further analysis of HLV013 via Western immunoblotting indicated a stronger, earlier antibody response to GP5 and GP5-M heterodimer when compared to VR2332 and sera from HLV013 infected pigs showed more cross-reaction with PRRSV strain IA97-7895 than did sera from VR2332 infected pigs (FIGS. 2 and 3). Results from these studies have led us to believe that N-glycosylation patterns in association with the GP5-M heterodimer are important components of a more effective neutralizing antibody response.

Figure 4:
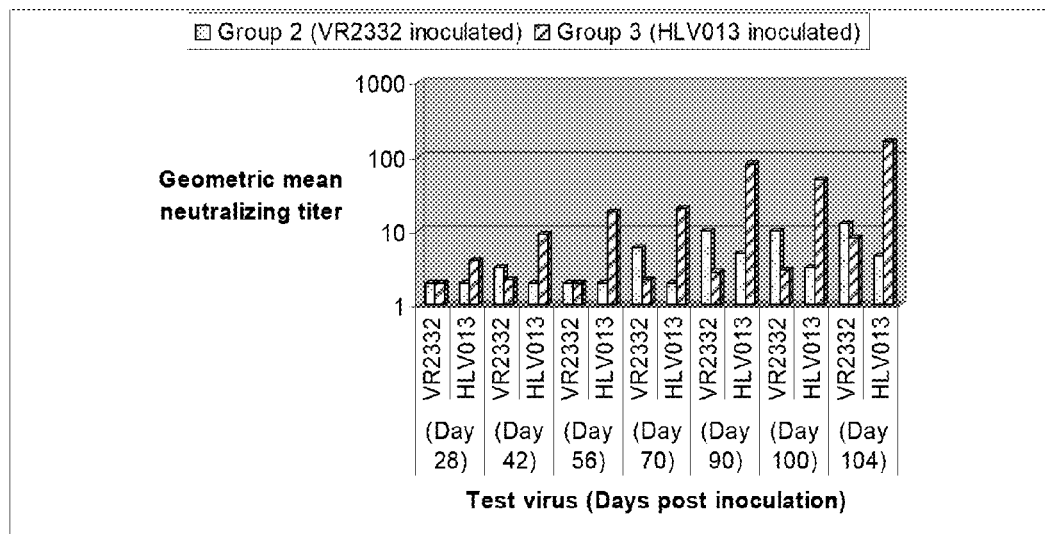
FIG. 4: Neutralizing antibody response in pigs given either 2 inoculations of HLV013 or VR2332. Geometric mean titers of 6 pigs per group. *Group 1 pigs (control) remained negative for neutralizing antibodies throughout the study. Compared to Group 2 pigs, Group 3 pigs had a quicker, more robust onset of neutralizing antibodies to homologous and heterologous virus.

The influence of glycosylation on the evolution of neutralizing antibodies was first shown in this experiment. In this experiment, 3 groups of 6 PRRSV negative pigs were treated as shown in Table A. Pigs were inoculated on Day 0 and again on Day 28 followed by inoculation with a heterologous strain on Day 90. Serum was collected during the course of the study and assayed for neutralizing antibodies against the inoculating and heterologous strains (FIG. 4).

TABLE A

| Pig inoculation Trial 1 design | | |
|---|---|---|
| Group # | Day 0 (prime) | Day 42 (boost) |
| 1 | PBS | PBS |
| 2 | VR2332 | VR2332 |
| 3 | HLV013 | HLV013 |

This trial provides evidence that there is a large difference between the protective antibody responses to strains that differ in glycosylation. See FIG. 5. HLV013 lacking glycans prior to aa44 had a faster, more robust antibody response pre-challenge with more cross-reactivity when compared to VR2332. Post-challenge pigs inoculated with HLV013 had a faster anamnestic response and a faster response time in generating antibodies to the challenge strain.

Figure 5:
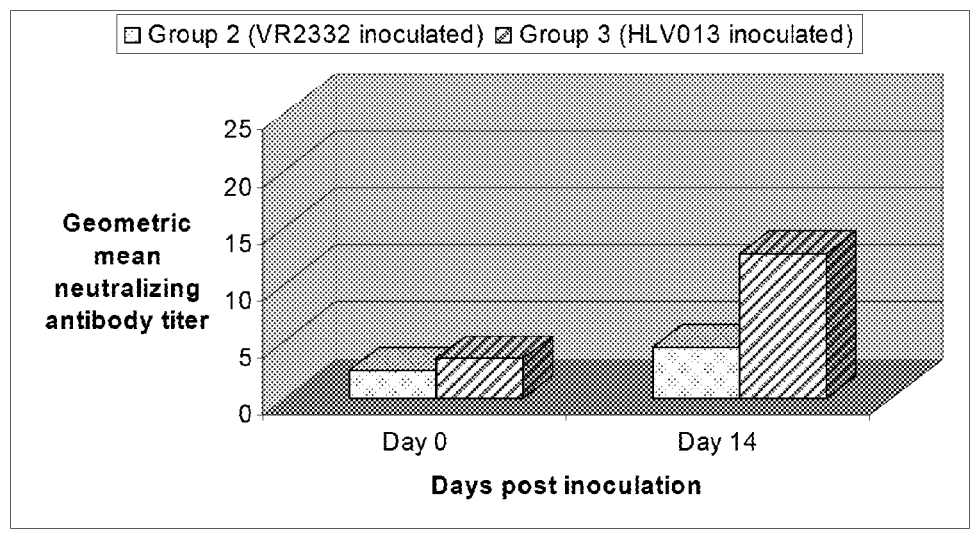
FIG. 5: Neutralizing antibody responses after inoculation with a heterologous strain (MN184). Please refer to Example 2 for a description of the individual lanes. This trial provides evidence that there is a large difference between the protective antibody responses to strains that differ in glycosylation. HLV013 lacking glycans prior to aa44 had a faster, more robust antibody response pre-challenge with more cross-reactivity when compared to VR2332. Post-challenge pigs inoculated with HLV013 had a faster anamnestic response and a faster response time in generating antibodies to the challenge strain. Note that the GP5-M heterodimer of MN184 and VR2332 are slightly higher (kDa) due to presence of additional N-glycans

The below table corresponds to the Western blot in FIG. 5.

| Lane # | Primary antibody source | Protein | HLV013 FFN | MN184 FFN | VR2332 FFN |
|---|---|---|---|---|---|
| 1 | NA | Ladder | NA | NA | NA |
| 2 | Group 1 | Purified PRRSV HLV013 | 128 | 8 | 16 |
| 3 | Group 1 | Purified PRRSV MN184 | 128 | 8 | 16 |
| 4 | Group 1 | Purified PRRSV VR2332 | 128 | 8 | 16 |
| 5 | Group 2 | Purified PRRSV HLV013 | 2048 | 256 | 256 |
| 6 | Group 2 | Purified PRRSV MN184 | 2048 | 256 | 256 |
| 7 | Group 2 | Purified PRRSV VR2332 | 2048 | 256 | 256 |

Each lane contains 10 ug of purified PRRSV. Primary antibodies were diluted 1:100 and secondary antibody was diluted 1:2000.

Example 3

Animal Inoculation

Two 2-3 week old pigs were obtained from a source with no detectable presence of PRRSV and housed at ISU research facilities. Following acclimatization, pigs were infected intranasally with $10^5$ TC-ID$_{50}$ of the desired strain. Pigs were bled on days −7, 0, 7, 21, 35, and 70 post-inoculation to allow adequate time for production of neutralizing antibodies followed by humane euthanasia. Sera was aliquoted and sent to ISU Diagnostic Lab for anti-N antibody ELISA (Herdcheck, IDEXX), SDSU Diagnostic Lab for MARC 145 serum neutralization assay (FFN), and University of Minnesota for neutralizing peptide ELISA (Plagemann). Remaining sera was used for inhibition of AM infection testing at ISU.

This experiment was conducted in order to further evaluate the ability of strains deficient in GP5 N-glycans to generate high titers of neutralizing antibodies and their cross-reactivity. Pigs negative for PRRSV were obtained and randomized into 3 groups as shown in Table B. At the termination of the trial, serum was collected from all pigs and assayed for virus neutralizing antibodies against a variety of different PRRSV strains (Table C).

TABLE B

| Group # | Day 0 | Day 70 | Day 103 |
|---|---|---|---|
| 1 | HLV013 | HLV013 | NA |
| 2 | HLV013 | HLV093 | NA |
| 3 | HLV013 | HLV093 | NVSL 97-7895 |

All doses of PRRSV were 1 ml given IM at a dose of $1 \times 10^6$ TCID$_{50}$/ml
NA = not applicable

TABLE C

Neutralizing antibody titers (geometric means) against various strains of PRRSV

| Group | HLV013 | ISU-P | NVSL 97-7895 | PrimePac | SD23983 | VR2332 | MN184 |
|---|---|---|---|---|---|---|---|
| 1 | 140.4 | 91.2 | 54.3 | 14.7 | 16.1 | 4.8 | 3.7 |
| 2 | 1216 | 512 | 363.1 | 363.1 | 64.7 | 128.8 | 108.4 |
| 3 | 363.1 | 363.1 | 257 | 216.3 | 91.2 | 91.2 | 76.7 |

Although all 3 groups generated homologous and heterologous neutralizing titers, Group 2 had clearly higher titers. Addition of a third glycantype in Group 3 did not enhance the antibody response beyond what was demonstrated in Group 2. This indicates that the combination of HLV013 and HLV093 are best suited for a universal vaccine to elicit heterologous neutralizing antibody.

Figure 6:
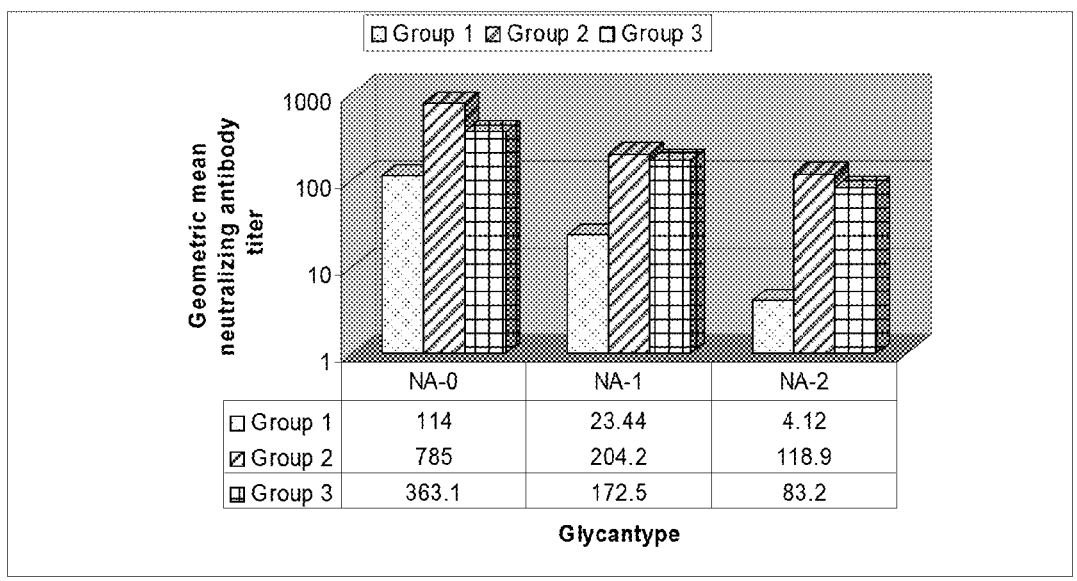
FIG. 6: Comparison of geometric mean neutralizing antibody titers generated in example 3 against different PRRSV glycantype groups.
Figure 7:
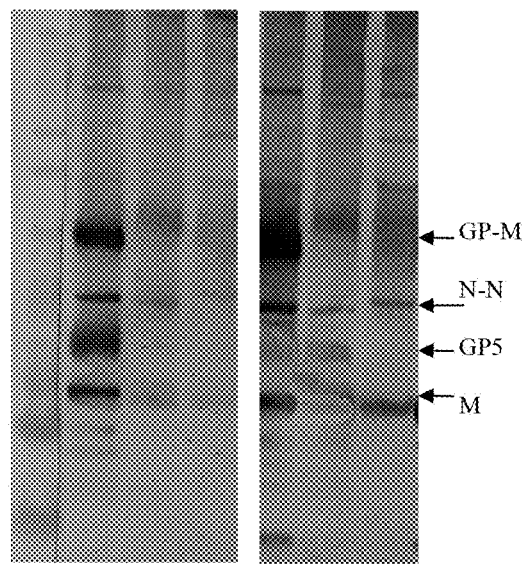
FIG. 7: Non-reduced western blot comparing the antibody reactivity of pigs from Groups 1 and 2. See table in example 3 for description of lane contents. This figure shows that the increase in protective antibodies generated in the HLV013-HLV093 scheme compared to HLV013 alone is due to an increased reactivity to the GP5-M heterodimer.
Figure 8:
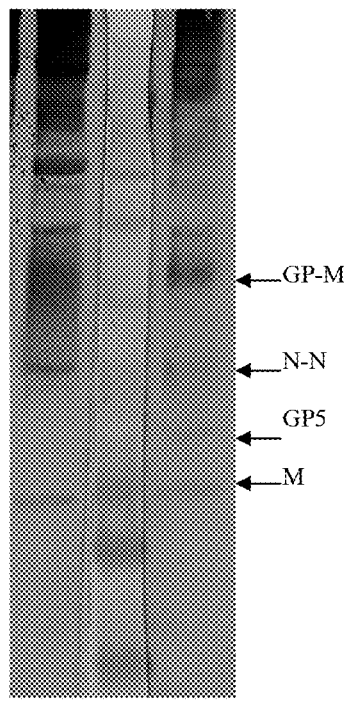
FIG. 8: Non-reduced western blot comparing antibody profiles of HLV013-HLV093 inoculated pig (Lane 1) to a VR2332-VR2332 inoculated pig (Lane 3). A ladder is shown in Lane 2. Purified VR2332 protein was used as the test antigen (10 ug per lane). Primary antibody dilution was 1:100 and secondary was 1:2000. The anti-VR2332FFN titer in Lane 1 was 256 and in Lane 3 was 16. Thus the HVL013-HLV093 inoculated pigs developed a higher anti-VR2332 neutralizing titer than pigs inoculated with VR2332-VR2332 itself. A clear difference in reaction to the GP-M heterodimer is also seen on the western blot.

The effect of the glycan shield can be further demonstrated by comparing the geometric means of the geometric means against strain groups with the same number of N-glycans prior to aa44. The 7 different strains used in the FFN assay were divided into 3 different groups based on glycantype; NA-0, NA-1, and NA-2. We would expect to see the highest titers against NA-0 strains and the lowest against NA-2 strains regardless of GP5 sequence homology. This is indeed what we saw as shown in FIG. 6. This ability to predict cross-reaction of protective antibodies supports the use of glycan-typing to define heterology amongst PRRSV strains.

Example 4

Collection of Alveolar Macrophages

AMs will be collected for culture as previously described (Mengeling, Thacker). Pigs (4-6 weeks old) will be anesthetized and euthanized by exsanguation. Lungs will be removed from the thoracic cavity for pulmonary lavage. Lavage fluid will consist of Dulbecco Modified Eagles Medium (DMEM) supplemented with gentamicin (0.5 mg/ml), penicillin (25 U/ml), streptomycin (25 µg/ml), polymyxin B sulfate (3 U/ml), and amphotericin B (25 ug/ml). The lavage fluid will be dispensed and aspirated several times in order to collect the AMs. We expect to collect 100-200 ml of lavage fluid per pig by pooling the aspirated fluid from individual pigs. Fluid from different pigs will not be mixed to avoid immune reactions and to identify any differences in AM susceptibility to PRRSV. Harvested fluid will be centrifuged at 1000 g for 15 min, resuspended in 50 ml of PBS, and washed two more times. AMs will be counted and resuspended in PBS at a concentration of approximately $5 \times 10^7$ AMs/1.5 ml followed by storage in liquid nitrogen. Batches will be validated by infecting AMs with PRRSV strain VR2332 and performing immunoperoxidase monolayer assay (IPMA) with known positive and negative sera to determine the $TCID_{50}$.

Example 5

Effect of Antibody Inhibition of Infection of Alveolar Macrophages

Polyclonal or monoclonal(s) antibodies will be diluted 2-fold and added to $10^5$ $TCID_{50}$ of various homologous and heterologous PRRSV strains. The mixtures will be incubated for 1 hour at 37 C and then inoculated onto alveolar macrophages (AMs) seeded in 96 well culture plates. Cells will be incubated for 1 hour at 37 C with 5% $CO_2$, washed, and incubated again until 10 hours post inoculation (Delputte). Cells will be fixed and the percentage of infected cells will be calculated based on immunoperoxidase staining. The t test will be used to compare percentage of infected cells between treatment and control wells.

Example 6

Immunoperoxidase Monolayer Assay

IPMA will be used to determine the percentage of infected cells as described by Delputte et al. Briefly, fixed cells will incubated for 1 hour at 37° C. with anti-nucleocapsid monoclonal antibody and 1/100 diluted in PBS with 10% goat serum, followed by incubation for 1 hour at 37° C. with peroxidase labeled goat anti-mouse Ig. Infected cells will be visualized by a substrate solution of 3-amino-9-ethylcarbazole in 0.05 M acetate buffer (pH 5) with 0.05% $H_2O_2$. Reaction will be blocked by washing with acetate buffer. Viral positive cells and total cells will be counted by light microscope to determine percentage of infected cells.

Example 7

Sodium Dodecyl Sulfate PolyAcrylamide Gel Electrophoresis (SDS-PAGE)

Equal volume of antigen will be mixed with 2×LDS loading buffer (Invitrogen) either including reducing agent or without reducing agent. All samples will be boiled for 5 minutes. Using 4-12% pre-made gradient Novex Nu-PAGE gels (Invitrogen) and an XCell SureLock mini-cell (Invitrogen), 15 µl of each sample will be loaded into their respective wells. SeeBlue Plus2 pre-stained ladder will be loaded in the first and last wells at a volume of 10 µl. Once the gel is loaded and both the buffer core and the lower buffer chamber are filled with 1×MES buffer (Invitrogen), the power supply current is set to 200 V and allowed to run for 45 minutes.

Example 8

Western Immunoblotting

Western blots will be used to further analyze and identify protective epitopes. Four blotting pads will be soaked in transfer buffer, consisting of 25 mM Bis-Tris, 25 mM Bicine, 1 mM Ethylenediaminetetraacetic acid (EDTA) with 10% Methanol. The Polyvinylidene fluoride (PVDF) will be briefly soaked in methanol and then placed in transfer buffer. Two blotting filter paper sheets will be soaked in transfer buffer. All are placed at 4° C. with remaining transfer buffer until the gel has finished. Once SDS-PAGE is completed, the gel cassette is removed and opened. After loading blotting materials, the blot module is filled with transfer buffer and the buffer chamber is filled with Nano purified water. The current will be set to 170 mA and 30 V and allowed to run for 75 minutes. The membrane will be removed from the blotting sandwich and transferred to a tray and covered in blocking buffer, ELISA wash with Fish Gelatin (1.5 mM $KH_2PO_4$, 20 mM $Na_2HPO_4$, 134 mM NaCl, 2.7 mM KCl, 0.05% Tween-20 with 0.25% Fish Gelatin). The membrane will be left in the blocking buffer overnight at 4° C. A 1:4000 dilution of swine serum will be made in 20 ml of blocking buffer. Blocking buffer will be poured off and swine serum dilution is added and allowed to rock at room temperature for 60 minutes. The swine serum dilution will be poured off and the membrane will be washed in 20 ml of ELISA wash for 10 minutes, rocking at room temperature. Wash will be poured off and the wash steps will be repeated twice for a total of three washes. During the last wash step, Biotin-SP conjugated Affinipure goat anti-swine IgG (Jackson Immuno Research) will be diluted 1:2000 in 20 ml of blocking buffer. After the final wash, goat anti-swine dilution will be poured onto the membrane and allowed to rock at room temperature for 60 minutes. Three wash steps will be repeated as previously described. A 1:2000 dilution of streptavidin Hrp (Zymed) in 20 ml of blocking buffer is prepared and poured onto the PVDF membrane, rocking at room temperature for 60 minutes. Three wash steps are repeated again. During the final wash step, TMB Membrane Peroxidase Substrate System (KPL) will be prepared by mixing in a small tray 12.5 ml of TMB Peroxidase Substrate, 12.5 ml Peroxidase Solution B and 2.5 ml TMB Membrane Enhancer. Once washing is complete, wash is poured off and the membrane is submerged in the substrate for 1 minute or until desired color of horseradish peroxidase is achieved without intense background. PVDF membrane will be dried and covered in clear plastic and scanned for electronic record of western blot.

Example 9

Quantitative Real-Time PCR

Quantitative real-time PCR (qRT-PCR) will be used as another method to compare the ability of antibodies to prevent binding and infection of AMs. Following infection and incubation of AM with antibody and PRRSV as described above, cells will be washed three times to remove extracellular, unbound virus and antibody-virus complexes. AMs will be harvested, lysed, and viral RNA extracted using the Qiagen Virus Spin Kit. Extract will then be assayed by qRT-PCR (Tetracore) on the Bio-Rad iCycler iQ and compared to a standard curve. The cycling conditions will be as follows: 1) RT step: 52° C. for 1800 seconds 2) Enzyme activation step: 95° C. for 900 seconds, 3) 3-step PCR: 40 cycles (changed from Tetracore's recommended 50 cycles) of (94° C. for 30 seconds, 61° C. for 60 seconds, and 72° C. for 60 seconds).

Example 10

Production of Antibodies Against PRRSV in Pigs

Twenty 5 to 6 week old conventional PRRSV-free pigs will be injected with a vaccine against PAD of PRRSV. Serum from each pig will be evaluated bi-weekly for antibody to PRRSV detectable by ELISA, and infection inhibition of alveolar macrophages (Erdman). Pigs will be injected repeatedly on bi-weekly occasions if adequate antibody levels are not attained. It is anticipated that pigs will be killed and blood collected for pooled serum 6 to 12 weeks post exposure. Twenty pigs of the same age will serve as uninfected controls and be the source of normal swine serum.

Example 11

Production of Antibodies Against PRRSV in Horses

Two horses will receive PAD polypeptide mixed in Freund's incomplete adjuvant by intramuscular injection followed by CVA only at bi-weekly intervals for 8 weeks. Serum from horses will be evaluated by infection inhibition of alveolar macrophages and Western blot analysis. Normal horse serum will be collected by repeated samplings prior to the immunization with CVA.

Example 12

Concentration of Antibodies to PAD of PRRSV

Plasma containing antibodies to PRRSV will be concentrated by removal of lipids and albumin by precipitation and subsequent ultrafiltration to 90% globulin content.

Example 13

Challenge Model for Evaluation of Antibodies for Protection Against PRRSV

Hysterectomy-derived, colostrums-deprived (HDCD) pigs will be procured from the Rexanne Struve Laboratory at 4-6 hours of age. Pigs will be fed a diet of Esbilac milk replacer. The milk replacer of pigs in principal groups will be supplemented with either pig or horse globulin containing antibodies to PAD of PRRSV. Control pigs will receive normal porcine or horse globulin of the same concentration as pigs in the principal groups. Esbilac containing globulin will not be fed after 36 hours of age. All pigs will be challenged intranasally with PRRSV strain HLV092 at 3 days of age. Each test preparation or combination will be evaluated in 10 HDCD pigs which are simultaneously challenged with 10 control pigs. One-half the pigs will be killed and necropsied 14 days after challenge and tissues (blood, lung, lymph nodes, tonsil) collected and assayed for presence of PRRSV by qPCR and virus isolation. Sentinel pigs will be placed with the remaining ½ pigs in each group to determine if challenged pigs are capable of transmission of the virus over the next 2 week time period.

Example 14

Field Experiment on PRRSV Positive Farm

A PRRSV positive farm will be selected with the following approximate mortality rates—farrowing 15-20% and nursery 10-15%. Pigs within each litter will be randomly assigned to 2 groups. Concentrated normal globulin (NG—Group 1) and PRRSV Ab concentrate generated against PAD (Group 2) will be orally administered prior to 24 hours of age and subsequently by intraperitoneal injection based on half-life determinations in the ISU experiments. The total number of pigs per group will be based on the number of pigs required to test a decrease in mortality rate by 10% in both farrowing and nursery. Statistical software (JMP 5.1.2, SAS Institute, Inc., Cary, N.C.) was used to determine the sample size for comparing proportions of two independent groups. At a power of 90%, 672 animals (336 per group) would be required to detect a 10% difference in mortality (from 20% to 10%) at the $p<0.05$ level of significance. To detect a 10% difference in mortality (from 15% to 5%) at the same power and p level, 536 animals (268 per group) are required. Cause of death will be determined by complete necropsy and submission of samples for qPCR.

Example 15

Statistical Analysis

The quantitative data collected (virus titration, qPCR, antibody titers) will be analyzed using ANOVA. Chi square test for proportions will be used for categorical data (mortality rate, % lung involvement, presence or absence of PRRSV). Analysis will be conducted using SAS statistical software and significance set at $p<0.05$.

Example 16

Supportive Data from Laboratory and Pig Studies

Figure 15:
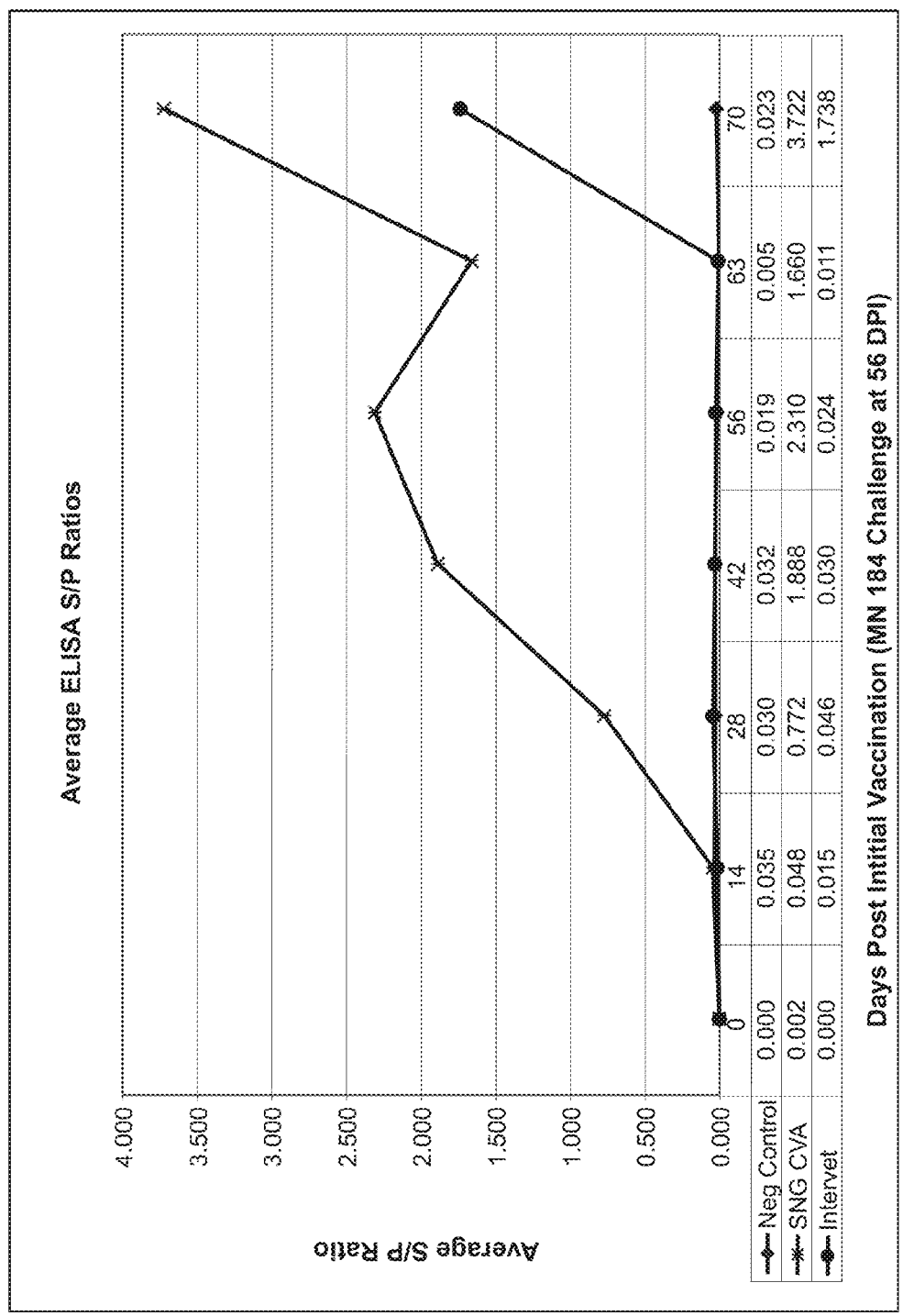
FIG. 15: Average IDEXX ELISA response in pigs inoculated with either HLV013 crude viral antigen (CVA) or Intervet's killed vaccine.

We have injected pigs with inactivated crude viral antigen comprising GP5, M, and GP5-M heterodimer prepared from HLV013 and compared the ELISA response (FIG. 15) to that of pigs injected with a commercial inactivated PRRS vaccine (Intervet). HLV013 induced rapid and high antibody titers as compared to the commercial vaccine.

A challenge study was conducted in which live HLV013 and VR2332 were inoculated in experimental pigs and later challenged with a heterologous strain (HLV092) of PRRSV (Table 6). Results indicated protection was induced by both viruses; however, resistance appeared to be induced more rapidly by HLV013. In experiment 1, strain HLV 093 was detected in the HLV013 group at 28 days post inoculation with HLV013.

One method of immunization with live PRRSV is as follows:

Step 1—inject pigs with live HLV013 (FIG. 10) on Day 1

Step 2—inject pigs with live HLV093 (FIG. 11) on Day 21

Step 3—inject pigs with live HLV092 (FIG. 12) on Day 42

Pigs immunized in these progressive steps will produce antibody to all the protective components of PAD and thus heterologous protection against most if not all of the current preponderant isolates of PRRSV in North America. Injection of animals with HLV092 first will not result in heterologous protection. For protection against European isolates, a similar scheme may be needed but using isolates of the European glycantypes, e.g. priming or administering with an European PRRSV strain that has little or no glycosylation among amino acids 31-39 in the GP5 ectodomain. For example, injection of pigs with LV does not induce antibodies to the GP 5 protein of VR2332 but it does induce antibodies to GP5 and the GP5-M heterodimer of LV.

TABLE 4

FFN data. Virus neutralization was tested on Marc 145 cells. Values indicate the reciprocal of the highest serum dilution exhibiting neutralization activity. Pigs (n = 6 per group) were inoculated on Day 0 with a sham control, HLV013, or VR2332 PRRSV strains. On Day 14, HLV013 group pigs were boostered (booster vaccinate shot) with HLV093. By day 42 dpi, only the HLV013 group showed VN activity. All groups were challenged with HLV092 on Day 90. The VN activity of the HLV013 group continued to increase when tested against homologous and heterologous virus.

| | | | | | FFN - Values <4 = Negative Result | | | | | | | |
|---|---|---|---|---|---|---|---|---|---|---|---|---|
| | FFN | 42 dpi* | 42 dpi | 42 dpi | 90 dpi/0 dpc** | | | | 104 dpi/14 dpc | | | |
| Group | virus | VR2332 | VR2332 | HLV013 | SD23983 | VR2332 | HLV092 | HLV013 | SD23983 | VR2332 | HLV092 | HLV013 |
| Control | 2544 | 2 | ND*** | ND | 2 | 2 | 2 | 2 | 2 | 2 | 2 | 2 |
| | 2545 | 2 | ND | ND | 2 | 2 | 2 | 2 | 2 | 2 | 2 | 2 |
| | 2547 | 2 | ND | ND | 2 | 2 | 2 | 2 | 2 | 2 | 4 | 2 |
| | 2548 | 2 | ND | ND | 2 | 2 | 2 | 2 | 2 | 2 | 2 | 2 |
| | 2550 | 2 | ND | ND | 2 | 2 | 2 | 2 | 4 | 4 | 2 | 2 |
| HLV013 | 2582 | 2 | 2 | 16 | 4 | 4 | 4 | 128 | 4 | 2 | 2 | 128 |
| | 2583 | 2 | 2 | 8 | 4 | 2 | 4 | 128 | 4 | 4 | 2 | 16 |
| | 2584 | 2 | 2 | 8 | 2 | 2 | 4 | 32 | 8 | 8 | 8 | 256 |
| | 2585 | 2 | 2 | 4 | 2 | 2 | 2 | 64 | 8 | 8 | 64 | >256 |
| | 2586 | 2 | 2 | 4 | 8 | 8 | 8 | 256 | 8 | 8 | 16 | 128 |
| | 2587 | 4 | 2 | 32 | 2 | 2 | 2 | 32 | 32 | 64 | 128 | >256 |
| VR2332 | 2594 | 2 | 4 | 2 | 4 | 8 | 2 | 4 | 32 | 32 | 8 | 16 |
| | 2595 | 4 | 2 | 2 | 4 | 8 | 2 | 8 | 8 | 8 | 4 | 4 |
| | 2596 | 4 | 2 | 2 | 8 | 16 | 8 | 8 | 4 | 8 | 2 | 2 |
| | 2597 | 2 | 2 | 2 | 4 | 8 | 2 | 4 | 8 | 8 | 2 | 2 |
| | 2598 | 4 | 4 | 2 | 8 | 16 | 2 | 4 | 64 | 32 | 32 | 4 |
| | 2599 | 4 | 2 | 2 | 2 | 8 | 2 | 4 | 4 | 8 | 2 | 2 |

*Days post inoculation
**Days post challenge
***Not Determined

TABLE 7

Glycantyping Scheme developed by the inventors. According to the present invention, PRRSV strains within the North American and European genotypes are grouped based on their glycosylation patterns. This discovery is referred to by the inventors as a glycantyping scheme. Glycantyping is a more accurate means of discerning heterologous PRRSV strains as new strains emerge in the population than sequence homology of ORF5. The present inventors contemplate that the discernment of glycosylation patterns can be used in single or multivalent vaccines or in the development of vaccination schemes and protocols.

| PRRSV Glycantype[a] | Number of predicted glycans[b,c] |
|---|---|
| NA-0 | 0[d] |
| NA-1 | 1 |
| NA-2 | 2 |
| NA-3 | 3 |
| NA-4 | 4 |
| NA-n | n |
| EU-0 | 0 |
| EU-1 | 1 |
| EU-2 | 2 |
| EU-3 | 3 |
| EU-4 | 4 |
| EU-n | n |

[a]NA = North American, EU = European.
[b]Number of glycans located on the ectodomain of GP5 excluding highly conserved glycans located at aa44 and 51 for NA strains and aa46 and 53 for EU strains. When these glycans are absent they should be noted as follows: if an NA-1 strain lacks a glycan at aa44 it is described as NA-1 (Δ44).
[c]As the number of predicted glycans increases so does the resistance to inducing protective (neutralizing) antibodies and/or susceptibility to such antibodies.
[d]NA-0 and EU-0 are predicted to be the parent strains for all NA and EU strains respectively. Thus these viruses should be included in attempts to generate cross-reacting antibodies. After NA-0 and EU-0, glycantyping may be a predictor of heterology which is currently poorly defined for PRRSV.
* This scheme may be applicable to other RNA viruses.

TABLE 7a

FFN data from pigs inoculated with HLV013 (two logs higher than in Table 5). Blood was collected 42 days after inoculation. Virus neutralization was tested on Marc 145 cells. Values indicate the reciprocal of the highest serum dilution exhibiting neutralization activity.

| Pig ID# | Virus used in neutralization assay | | |
|---|---|---|---|
|  | HLV013 | SD 23983 | VR2332 |
| 1 | 64 | 16 | 8 |
| 2 | 32 | 4 | 4 |
| 3 | 16 | 32 | 4 |
| 4 | 64 | 64 | 8 |
| 5 | 64 | 8 | 8 |
| 6 | 256 | 8 | 8 |
| 7 | 64 | 8 | 4 |
| 8 | 16 | 4 | <4 |
| 9 | 128 | 16 | 8 |
| 10 | 64 | 8 | 4 |
| 11 | 16 | <4 | <4 |
| 12 | 32 | <4 | <4 |
| 13 | 64 | 32 | 8 |
| 14 | 64 | 8 | <4 |
| 15 | 64 | 8 | <4 |
| 16 | 64 | 4 | 4 |
| 17 | 256 | 4 | <4 |
| 18 | 128 | 4 | 4 |
| 19 | 64 | 32 | 4 |
| 20 | >256 | 16 | 16 |

TABLE 8

Data from virulent PRRSV (HLV092) challenge of pigs described in FIG. 16 and Tables 6-7.

| Treatment | Severity of IP[a] | Pathology[b] | qPCR[c] |
|---|---|---|---|
| Controls—Non-vacc | 4/5 | PLH: 2 mild, 1 moderate | 5 × 10⁷ |
| Vacc—HLV013 | 0/5 | PLH: 3 mild | 0.00 |
| Vacc—VR2332 | 0/5 | PLH: 2 mild, 3 severe | 0.00 |

[a]Number of pigs with an interstitial pneumonia (IP) lung score >2 on a scale of 1 to 6.
[b]Number of pigs with either mild, moderate, or severe peribronchiolar lymphoid hyperplasia (PLH) based on histopathology.
[c]Quantitative PCR (average viral copies per ml) from serum 10 days post challenge.

TABLE 9

PRRSV ORF 5 Sequencing. Nucleotide sequences were translated into amino acid sequences[1] and N-glycosylation sites were predicted[2]. Only the first 80 aa are shown, however genotypic relatedness (percent homology) is based on entire sequence (200 aa). Potential N-glycosylation sites are underlined.
Please amend Table 9 at page 73 as follows:

| Inoculating Virus | First 80 Amino Acids (N-glycosylation sites in red highlighting) | Glycans | SEQ ID NO: |
|---|---|---|---|
| HLV094 | MLGRCLTAGC CSRLLSLWCI VPFCFAALVN ANSNSSSHLQ LIYNLTLCEL NGTDWLKDKF DWAVETFVIF PVLTHIVSYG | 33, 44, 51 | 95 |
| HLV013 | MLGRCLTAGC CSRLLSLWCI VPFCFVALVN ANSNSGSHLQ LIYNLTLCEL NGTDWLKDKF DWAVETFVIF PVLTHIVSYS | 44, 51 | 96 |
| HLV093 | MLGKCLTAGY CSQLPFLWCI VPFCLAALVN ANNDSSSHLQ LIYSLTICEL NGTEWLNEHF SWAVETFVIF PALTHIVSYG | 33, 51 | 97 |
| VR2332 | MLEKCLTAGC CSRLLSLWCI VPFCFAVLAN ASNDSSSHLQ LIYNLTLCEL NGTDWLANKF DWAVESFVIF PVLTHIVSYG | 30, 33, 44, 51 | 98 |

| Pig Serum | First 80 Amino Acids | Genotypic Relatedness |
|---|---|---|

TABLE 9-continued

PRRSV ORF 5 Sequencing. Nucleotide sequences were translated into amino acid sequences[1] and N-glycosylation sites were predicted[2]. Only the first 80 aa are shown, however genotypic relatedness (percent homology) is based on entire sequence (200 aa). Potential N-glycosylation sites are underlined.
Please amend Table 9 at page 73 as follows:

| Group ID | # | Seq. # | DPI | (N-glycosylation sites in red highlighting) | Glycans | to HLV013 | |
|---|---|---|---|---|---|---|---|
| HLV013 2582 | 5436 | HLV079 | 14 | MLGRCLTAGC CSRLLSLWCI VPFCFVALVN ANSNSGSHLQ LIYNLTLCEL NGTDWLKDKF DWAVETFVIF PVLTHIVSYS | 44, 51 | 100% | 99 |
| HLV013 2582 | 5465 | HLV083 | 28 | MLGRCLTAGC CSRLLSLWCI VPFCFVALVN ANSNSSSHLQ LIYNLTLCEL NGTDWLKDKF DWAVETFVIF PVLTHIVSYS | 34, 44, 51 | 99.67% | 100 |
| HLV013 2586* | 5440 | HLV080 | 14 | MLGKCLTAGY CSQLPFLWCI VPFCLAALVN ANNDSSSHLQ LIYNLTICEL NGTEWLNEHF SWAVETFVIF PALTHIVSYG | 33, 44, 51 | 85.57% | 101 |
| HLV013 2586 | 5469 | | 28 | No PCR Product – two runs for sequencing | | | |
| HLV013 2587 | 5441 | HLV081 | 14 | MLGRCLTAGC CSRLLSLWCI VPFCFVALVN ANSNSGSHLQ LIYNLTLCEL NGTDWLKDKF DWAVETFVIF PVLTHIVSYS | 44, 51 | 100% | 102 |
| HLV013 2587 | 5470 | HLV086 | 28 | MLGRCLTAGC CSRLLSLWCI VPFCFVALVN ANSNNGSHLQ LIYNLTLCEL NGTDWLKDKF DWAVETFVIF PVLTHIVSYS | 44, 51 | 98.83% | 103 |
| HLV094 2581* | 5464 | HLV082 | 28 | MLGKCLTAGY CSQLPFLWCI VPFCLAALVN ANNDSSSHLQ LIYNLTICEL NGTEWLNEHF SWAVETFVIF PALTHIVSYG | 33, 44, 51 | | 104 |
| HLV093 2588* | 5471 | HLV087 | 28 | MLGKCLTAGY CSQLPFLWCI VPFCLAALVN ANNDSSSHLQ LIYNLTICEL NGTEWLNEHF SWAVETFVIF PALTHIVSYG | 33, 41, 51 | | 105 |
| | | | | | | Genotypic Relatedness to HLV093 | |
| HLV013 2586 | 5440 | HLV080 | 14 | MLGKCLTAGY CSQLPFLWCI VPFCLAALVN ANNDSSSHLQ LIYNLTICEL NGTEWLNEHF SWAVETFVIF PALTHIVSYG | 33, 44, 51 | 99.84% | 105 |
| HLV094 2581 | 5464 | HLV082 | 28 | MLGKCLTAGY CSQLPFLWCI VPFCLAALVN ANNDSSSHLQ LIYNLTICEL NGTEWLNEHF SWAVETFVIF PALTHIVSYG | 33, 44, 51 | 99.84% | 105 |
| HLV093 2588 | 5471 | HLV087 | 28 | MLGKCLTAGY CSQLPFLWCI VPFCLAALVN ANNDSSSHLQ LIYNLTICEL NGTEWLNEHF SWAVETFVIF PALTHIVSYG | 33, 44, 51 | 99.84% | 105 |

*Identical genotypes
[1]ExPASy-Translate Tool
[2]NetNGlyc 1.0 Server

DEPOSITS

A deposit of the viruses of HLV013, HLV092, HLV093, and MN184 is and has been maintained by Dr. Delbert Harris, Room 45, Kildee Hall, Iowa State University, Ames, Iowa 50011, since prior to the filing date of this application. Access to this deposit will be available during the pendency of the application to the Commissioner of Patents and Trademarks and person determined by the Commissioner to be entitled thereto upon request. Upon allowance of any claims in the application, the Applicant(s) will make available to the public without restriction a deposit of at least 25 frozen or freeze-dried samples (1 ml each) of HLV013, HLV092, HLV093, HLV094, and MN184 viruses with the American Type Culture Collection (ATCC), Manassas, Va. 20110. The 25 frozen or freeze-dried samples (1 ml each) of PRRSV of HLV013, HLV092, HLV093, HLV094, and MN184 viruses deposited with the ATCC will be taken from the same deposit maintained at Room 45, Kildee Hall, Iowa State University and described above. Additionally, Applicant(s) will meet all the requirements of 37 C.F.R. §1.801-1.809, including providing an indication of the viability of the sample when the deposit is made. This deposit of 25 frozen or freeze-dried samples (1 ml each) of HLV013, HLV092, HLV093, HLV094, and MN184 viruses will be maintained without restriction in the ATCC Depository, which is a public depository, for a period of 30 years, or 5 years after the most recent request, or for the enforceable life of the patent, whichever is longer, and will be replaced if it ever becomes nonviable during that period.

What is claimed is:

1. A method for treating a porcine reproductive respiratory syndrome virus—(PRRSV) infection in a pig comprising:
    administering to said pig a therapeutically effective amount of a vaccine comprising a first heterodimer of a matrix protein (M protein) of porcine reproductive and respiratory syndrome virus (PRRSV) and a glycoprotein 5 (GP5) of PRRSV (GP5-M heterodimer), wherein the GP5 of the first GP5-M heterodimer has glycosylation at position 44 of the GP5 in a North American (NA) PRRSV or glycosylation at position 46 of the GP5 in a European (EU) PRRSV; and
    administering to said pig a second GP5-M heterodimer, wherein the GP5 of the second GP5-M heterodimer does not have glycosylation at position 44 of GP5 in a North American (NA) PRRSV or at position 46 of the GP5 in a European (EU) PRRSV, thereby treating a PRRSV infection in a pig, wherein the position number of 44 is determined from sequence alignment with the amino acid sequence of SEQ ID NO: 1, and the position number 46 is determined from the amino acid sequence of SEQ ID NO: 4.

2. A multivalent vaccine comprising GP5-M protein heterodimers of PRRSV:
    comprising a heterodimer of a matrix protein (M protein) of porcine reproductive and respiratory syndrome virus (PRRSV) and a glycoprotein 5 (GP5) of PRRSV, wherein said GP5 protein has N-glycosylation of asparagine amino acid located at position 44 of the GP5 protein in North American PRRSV strains or at position 46 of the GP5 protein in European PRRSV strains; and
    comprising a heterodimer of a matrix protein (M protein) of porcine reproductive and respiratory syndrome virus (PRRSV) and a glycoprotein 5 (GP5) of PRRSV, wherein said GP5 protein does not have N-glycosylation of asparagine amino acid located at position 44 of the GP5 protein in North American PRRSV strains or at position 46 of the GP5 protein in European PRRSV strains, wherein the position number of 44 is determined from sequence alignment with the amino acid sequence of SEQ ID NO: 1, and the position number 46 is determined from the amino acid sequence of SEQ ID NO: 4.

3. A GP5-M heterodimer subunit vaccine comprising:
comprising a heterodimer of a matrix protein (M protein of porcine reproductive and respiratory syndrome virus (PRRSV) and a glycoprotein 5 (GP5) of PRRSV, wherein said GP5 protein has N-glycosylation of asparagine amino acid located at position 44 of the GP5 protein in North American PRRSV strains or at position 46 of the GP5 protein in European PRRSV strains; and
comprising a heterodimer of a matrix protein (M protein) of porcine reproductive and respiratory syndrome virus (PRRSV) and a glycoprotein 5 (GP5) of PRRSV, wherein said GP5 protein does not have N-glycosylation of asparagine amino acid located at position 44 of the GP5 protein in North American PRRSV strains or at position 46 of the GP5 protein in European PRRSV strains, wherein the position number of 44 is determined from sequence alignment with the amino acid sequence of SEQ ID NO: 1, and the position number 46 is determined from the amino acid sequence of SEQ ID NO: 4.

4. The subunit vaccine of claim 3 wherein the vaccine further comprises a heterodimer of said M protein of PRRSV and said GP5 of PRRSV, wherein the GP5 protein is linked to the M protein by a disulfide bond, wherein the disulfide bond results from bond between a cysteine amino acid in the M protein located at position 9 in North American PRRSV strains or at position 8 in EU PRRSV strains with a cysteine amino acid at position 48 of the GP5 protein in North American PRRSV strains or at position 50 in European PRRSV strains, thereby producing a GP5-M heterodimer, wherein the amino acid positions 9 and 48 in North American PRRSV strains are relatively to the amino acid reference sequence to the SEQ ID NO: 1 and the amino acid position of 8 and 50 in European PRRSV strains are relative to the reference amino acid sequence of SEQ ID NO: 4.

5. The subunit vaccine of claim 3 wherein said GP5 further comprises at least one glycosylated amino acid from amino acids 1-43 of the GP5 ectodomain in North American PRRSV strains or from amino acids 1-45 of the GP5 ectodomain in European PRRSV strains, wherein the amino acids 1-43 of North American PRRSV strains are relatively to the amino acid reference sequence to the SEQ ID NO: 1 and amino acids position 1-45 in European PRRSV strains are relative to the reference amino acid sequence of SEQ ID NO: 4.

* * * * *

UNITED STATES PATENT AND TRADEMARK OFFICE
CERTIFICATE OF CORRECTION

| | | |
|---|---|---|
| PATENT NO. | : 8,771,670 B2 | Page 1 of 1 |
| APPLICATION NO. | : 13/533167 | |
| DATED | : July 8, 2014 | |
| INVENTOR(S) | : Harris et al. | |

It is certified that error appears in the above-identified patent and that said Letters Patent is hereby corrected as shown below:

In the Claims

Col. 125, Claim 3, Line 6:
ADD after (M protein --)--

Col. 126, Claim 4, Line 10:
DELETE after are "relatively"
ADD after are --relative--

Col. 126, Claim 5, Line 19:
DELETE after are "relatively"
ADD after are --relative--

Signed and Sealed this
Fourth Day of November, 2014

Michelle K. Lee
*Deputy Director of the United States Patent and Trademark Office*

SEQUENCE LISTING

<160> NUMBER OF SEQ ID NOS: 105

<210> SEQ ID NO 1
<211> LENGTH: 60
<212> TYPE: PRT
<213> ORGANISM: porcine reproductive and respiratory syndrome virus

<400> SEQUENCE: 1

Met Leu Gly Arg Cys Leu Thr Ala Gly Cys Cys Ser Gln Leu Pro Phe
1               5                   10                  15

Leu Trp Cys Ile Val Pro Phe Cys Leu Val Ala Leu Val Asn Ala Asn
            20                  25                  30

Ser Asn Ser Gly Ser His Leu Gln Leu Ile Tyr Asn Leu Thr Leu Cys
        35                  40                  45

Glu Leu Asn Gly Thr Asp Trp Leu Lys Asp Lys Phe
    50                  55                  60

<210> SEQ ID NO 2
<211> LENGTH: 60
<212> TYPE: PRT
<213> ORGANISM: porcine reproductive and respiratory syndrome virus

<400> SEQUENCE: 2

Met Leu Gly Arg Cys Leu Thr Ala Cys Tyr Cys Leu Arg Leu Leu Ser
1               5                   10                  15

Leu Trp Cys Ile Val Pro Phe Trp Phe Ala Val Leu Val Ser Ala Asn
            20                  25                  30

Ser Asn Ser Ser Ser His Leu Gln Ser Ile Tyr Lys Leu Thr Leu Cys
        35                  40                  45

Glu Leu Asn Gly Thr Glu Trp Leu Asn Glu Arg Phe
    50                  55                  60

<210> SEQ ID NO 3
<211> LENGTH: 60
<212> TYPE: PRT
<213> ORGANISM: porcine reproductive and respiratory syndrome virus

<400> SEQUENCE: 3

Met Leu Gly Arg Cys Leu Thr Ala Gly Tyr Cys Ser Gln Leu Pro Ser
1               5                   10                  15

Leu Trp Cys Ile Val Pro Phe Trp Phe Ala Val Leu Val Ser Ala Asn
            20                  25                  30

Ser Thr Ser Ser Ser Tyr Ser Gln Leu Ile Tyr Asn Leu Thr Ile Cys
        35                  40                  45

Glu Leu Asn Gly Pro Asp Trp Leu Asn Glu Lys Phe
    50                  55                  60

<210> SEQ ID NO 4
<211> LENGTH: 60
<212> TYPE: PRT
<213> ORGANISM: porcine reproductive and respiratory syndrome virus

<400> SEQUENCE: 4

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
        35                  40                  45

```
Ile Cys Glu Leu Asn Gly Thr Asp Trp Leu Ser Ser
    50                  55                  60

<210> SEQ ID NO 5
<211> LENGTH: 60
<212> TYPE: PRT
<213> ORGANISM: porcine reproductive and respiratory syndrome virus

<400> SEQUENCE: 5

Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Asn
                20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asn His Phe
    50                  55                  60

<210> SEQ ID NO 6
<211> LENGTH: 60
<212> TYPE: PRT
<213> ORGANISM: porcine reproductive and respiratory syndrome virus

<400> SEQUENCE: 6

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
                20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe
    50                  55                  60

<210> SEQ ID NO 7
<211> LENGTH: 60
<212> TYPE: PRT
<213> ORGANISM: porcine reproductive and respiratory syndrome virus

<400> SEQUENCE: 7

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
                20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe
    50                  55                  60

<210> SEQ ID NO 8
<211> LENGTH: 60
<212> TYPE: PRT
<213> ORGANISM: porcine reproductive and respiratory syndrome virus

<400> SEQUENCE: 8

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
                20                  25                  30

Ser Asn Ser Ser Ser His Leu Gln Leu Ile Tyr Asn Leu Thr Leu Cys
        35                  40                  45
```

```
Glu Leu Asn Gly Thr Asp Trp Leu Lys Asp Lys Phe
    50                  55                  60
```

<210> SEQ ID NO 9
<211> LENGTH: 60
<212> TYPE: PRT
<213> ORGANISM: porcine reproductive and respiratory syndrome virus

<400> SEQUENCE: 9

```
Met Leu Gly Lys Cys Leu Thr Ala Gly Cys Cys Ser Arg Leu Leu Ser
1               5                   10                  15

Phe Trp Cys Ile Val Pro Phe Cys Phe Ala Val Leu Val Asn Ala Ser
            20                  25                  30

Tyr Ser Ser Ser Ser His Leu Gln Leu Ile Tyr Asn Leu Thr Leu Cys
        35                  40                  45

Glu Leu Asn Gly Thr Asp Trp Leu Ala Asn Lys Phe
    50                  55                  60
```

```
<210> SEQ ID NO 13
<211> LENGTH: 36
<212> TYPE: PRT
<213> ORGANISM: porcine reproductive and respiratory syndrome virus

<400> SEQUENCE: 13

Asn Ala Ser Asn Asp Ser Ser His Leu Gln Leu Ile Tyr Asn Leu
1               5                   10                  15

Thr Leu Cys Glu Leu Asn Gly Thr Asp Trp Leu Ala Asn Lys Phe Asp
                20                  25                  30

Trp Ala Val Glu
            35

<210> SEQ ID NO 14
<211> LENGTH: 26
<212> TYPE: PRT
<213> ORGANISM: porcine reproductive and respiratory syndrome virus

<400> SEQUENCE: 14

Met Gly Ser Ser Leu Asp Asp Phe Cys His Asp Ser Thr Ala Pro Gln
1               5                   10                  15

Lys Val Leu Leu Ala Phe Ser Ile Thr Tyr
            20                  25

<210> SEQ ID NO 15
<211> LENGTH: 20
<212> TYPE: PRT
<213> ORGANISM: porcine reproductive and respiratory syndrome virus

<400> SEQUENCE: 15

Asp Thr Ala Gly Leu Val Thr Val Ser Thr Ala Gly Phe Tyr His Gly
1               5                   10                  15

Arg Tyr Val Leu
            20

<210> SEQ ID NO 16
<211> LENGTH: 36
<212> TYPE: PRT
<213> ORGANISM: porcine reproductive and respiratory syndrome virus

<400> SEQUENCE: 16

Asn Ala Asn Ser Asn Ser Gly Ser His Leu Gln Leu Ile Tyr Asn Leu
1               5                   10                  15

Thr Leu Cys Glu Leu Asn Gly Thr Asp Trp Leu Lys Asp Lys Phe Asp
                20                  25                  30

Trp Ala Val Glu
            35

<210> SEQ ID NO 17
<211> LENGTH: 26
<212> TYPE: PRT
<213> ORGANISM: porcine reproductive and respiratory syndrome virus

<400> SEQUENCE: 17

Met Gly Ser Ser Leu Asp Asp Phe Cys Tyr Asp Ser Thr Ala Pro Gln
1               5                   10                  15

Lys Val Leu Leu Ala Phe Ser Ile Thr Tyr
            20                  25

<210> SEQ ID NO 18
<211> LENGTH: 20
<212> TYPE: PRT
```

```
<213> ORGANISM: porcine reproductive and respiratory syndrome virus

<400> SEQUENCE: 18

Asp Thr Val Gly Leu Ile Thr Val Ser Thr Ala Gly Tyr Tyr His Lys
1               5                   10                  15

Arg Tyr Val Leu
            20

<210> SEQ ID NO 19
<211> LENGTH: 36
<212> TYPE: PRT
<213> ORGANISM: porcine reproductive and respiratory syndrome virus

<400> SEQUENCE: 19

Asn Ala Asn Asn Asp Ser Ser Ser His Leu Gln Leu Ile Tyr Ser Leu
1               5                   10                  15

Thr Ile Cys Glu Leu Asn Gly Thr Glu Trp Leu Asn Glu His Phe Ser
            20                  25                  30

Trp Ala Val Glu
        35

<210> SEQ ID NO 20
<211> LENGTH: 26
<212> TYPE: PRT
<213> ORGANISM: porcine reproductive and respiratory syndrome virus

<400> SEQUENCE: 20

Met Gly Ser Ser Leu Asp Asp Phe Cys His Asp Ser Thr Ala Pro Gln
1               5                   10                  15

Lys Val Leu Leu Ala Phe Ser Ile Thr Tyr
            20                  25

<210> SEQ ID NO 21
<211> LENGTH: 20
<212> TYPE: PRT
<213> ORGANISM: porcine reproductive and respiratory syndrome virus

<400> SEQUENCE: 21

Asp Thr Val Gly Leu Ile Thr Val Ser Thr Ala Gly Tyr Tyr His Ala
1               5                   10                  15

Arg Tyr Val Leu
            20

<210> SEQ ID NO 22
<211> LENGTH: 36
<212> TYPE: PRT
<213> ORGANISM: porcine reproductive and respiratory syndrome virus

<400> SEQUENCE: 22

Asn Ala Ser Ser Asn Ser Ser Ser His Leu Gln Leu Ile Tyr Asn Leu
1               5                   10                  15

Thr Leu Cys Glu Leu Asn Gly Thr Asp Trp Leu Asn Asp His Phe Ser
            20                  25                  30

Trp Ala Val Glu
        35

<210> SEQ ID NO 23
<211> LENGTH: 20
<212> TYPE: PRT
<213> ORGANISM: porcine reproductive and respiratory syndrome virus

<400> SEQUENCE: 23
```

Phe Phe Asp Ala Leu Gly Leu Gly Ala Val Ser Thr Ala Gly Phe Val
1               5                   10                  15

Gly Gly Arg Tyr
            20

<210> SEQ ID NO 24
<211> LENGTH: 36
<212> TYPE: PRT
<213> ORGANISM: porcine reproductive and respiratory syndrome virus

<400> SEQUENCE: 24

Ala Asp Gly Asn Gly Asp Ser Ser Thr Tyr Gln Tyr Ile Tyr Asn Leu
1               5                   10                  15

Thr Ile Cys Glu Leu Asn Gly Thr Asp Trp Leu Ser Ser His Phe Gly
            20                  25                  30

Trp Ala Val Glu
            35

<210> SEQ ID NO 25
<211> LENGTH: 603
<212> TYPE: DNA
<213> ORGANISM: porcine reproductive and respiratory syndrome virus

<400> SEQUENCE: 25
atgttgggga gatgcttgac cgcgggctgt tgctcgcgat tgctttcttt gtggtgtatc      60
gtgccatttt gttttgttgc gctcgtcaac gccaacagca acagcggctc tcatcttcag    120
ttaatttaca acttgacgct atgtgagctg aatggcacag attggctgaa agacaaattt    180
gattgggcag tggagacttt tgtcatcttt cccgtgttga ctcacattgt ctcatatagt    240
gcactcacca ctagccattt ccttgacaca gccggtctgg ttactgtgtc tactgccggg    300
ttctaccacg gcggtatgt tctgagtagc atctacgcgg tctgcgctct ggccgcattg    360
acttgcttcg tcattaggct tgcgaagaac tgcatgtcct ggcgctactc ttgtaccaga    420
tatactaact tccttctgga cactaagggc agactctatc gctggcggtc gcccgttatc    480
atagagaaag ggggtaaggt tgaggtcgaa ggtcacctga tcgacctcaa aagagttgtg    540
cttgatggtt ccgtggcaac ccctttaacc agagtttcag cggaacaatg gggtcgtctt    600
tag                                                                 603

<210> SEQ ID NO 26
<211> LENGTH: 200
<212> TYPE: PRT
<213> ORGANISM: porcine reproductive and respiratory syndrome virus

<400> SEQUENCE: 26

Met Leu Gly Arg Cys Leu Thr Ala Gly Cys Cys Ser Arg Leu Leu Ser
1               5                   10                  15

Leu Trp Cys Ile Val Pro Phe Cys Phe Val Ala Leu Val Asn Ala Asn
            20                  25                  30

Ser Asn Ser Gly Ser His Leu Gln Leu Ile Tyr Asn Leu Thr Leu Cys
        35                  40                  45

Glu Leu Asn Gly Thr Asp Trp Leu Lys Asp Lys Phe Asp Trp Ala Val
    50                  55                  60

Glu Thr Phe Val Ile Phe Pro Val Leu Thr His Ile Val Ser Tyr Ser
65                  70                  75                  80

Ala Leu Thr Thr Ser His Phe Leu Asp Thr Ala Gly Leu Val Thr Val
                85                  90                  95

```
Ser Thr Ala Gly Phe Tyr His Gly Arg Tyr Val Leu Ser Ser Ile Tyr
            100                 105                 110

Ala Val Cys Ala Leu Ala Ala Leu Thr Cys Phe Val Ile Arg Leu Ala
            115                 120                 125

Lys Asn Cys Met Ser Trp Arg Tyr Ser Cys Thr Arg Tyr Thr Asn Phe
            130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
            195                 200

<210> SEQ ID NO 27
<211> LENGTH: 525
<212> TYPE: DNA
<213> ORGANISM: porcine reproductive and respiratory syndrome virus

<400> SEQUENCE: 27
atggggtcgt ctttagacga cttttgctat gatagcacgg ctccacaaaa ggtgcttttg      60
gcgttttcca ttacctacac gccagtgatg atatatgctc taaaggtaag tcgcggccga     120
cttttagggc ttctgcacct tttgatcttt ctgaattgtg cttttacctt cgggtacatg     180
acattcgtgc actttaatag cacaaataag gtcgcgctca ctatgggagc agtagttgca     240
cttctttggg gggtgtactc agccatagaa acctggaagt tcatcacctc cagatgtcgt     300
ttgtgcttgc taggccgcaa gtacattctg gcccccgccc accacgtcga agtgccgcg      360
ggctttcatc cgatcgcggc aaatgataac cacgcatttg tcgtccggcg tcccggctcc     420
actacggtta acggcacatt ggtgcccggg ttgaaaagcc tcgtgttggg tggcagaaaa     480
gctgttaaac agggagtggt aaaccttgtc aaatatgcca ataa                      525

<210> SEQ ID NO 28
<211> LENGTH: 174
<212> TYPE: PRT
<213> ORGANISM: porcine reproductive and respiratory syndrome virus

<400> SEQUENCE: 28

Met Gly Ser Ser Leu Asp Asp Phe Cys Tyr Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
            35                  40                  45

Ile Phe Leu Asn Cys Ala Phe Thr Phe Gly Tyr Met Thr Phe Val His
        50                  55                  60

Phe Asn Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
            115                 120                 125
```

Asp Asn His Ala Phe Val Val Arg Arg Pro Gly Ser Thr Thr Val Asn
130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 29
<211> LENGTH: 174
<212> TYPE: PRT
<213> ORGANISM: porcine reproductive and respiratory syndrome virus

<400> SEQUENCE: 29

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
                20                  25                  30

Ala Leu Lys Val Ser Arg Gly Arg Leu Leu Gly Leu Leu His Leu Leu
            35                  40                  45

Ile Phe Leu Asn Cys Ala Phe Thr Phe Gly Tyr Met Thr Phe Ala His
50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Arg Phe His Pro Ile Ala Ala Asn
        115                 120                 125

Asp Asn His Ala Phe Val Val Arg Arg Pro Gly Ser Thr Thr Val Asn
130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 30
<211> LENGTH: 174
<212> TYPE: PRT
<213> ORGANISM: porcine reproductive and respiratory syndrome virus

<400> SEQUENCE: 30

Met Gly Ser Ser Leu Asp Asp Phe Cys His Asp Ser Thr Ala Pro Glu
1               5                   10                  15

Lys Val Leu Leu Ala Phe Ser Ile Thr Tyr Thr Pro Val Met Ile Tyr
                20                  25                  30

Ala Leu Lys Val Ser Arg Gly Arg Leu Leu Gly Leu Leu His Leu Leu
            35                  40                  45

Ile Phe Leu Asn Cys Ala Phe Thr Phe Gly Tyr Met Thr Phe Ala His
50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
            115                 120                 125

Asp Asn His Ala Phe Val Arg Arg Pro Gly Ser Thr Thr Val Asn
        130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 31
<211> LENGTH: 172
<212> TYPE: PRT
<213> ORGANISM: porcine reproductive and respiratory syndrome virus

<400> SEQUENCE: 31

Met Gly Ser Leu Asp Asp Phe Cys Asn Asp Ser Thr Ala Ala Gln Lys
1               5                   10                  15

Leu Val Leu Ala Phe Ser Ile Thr Tyr Thr Pro Ile Met Ile Tyr Ala
            20                  25                  30

Leu Lys Val Ser Arg Gly Arg Leu Leu Gly Leu Leu His Ile Leu Ile
        35                  40                  45

Phe Leu Asn Cys Ser Phe Thr Phe Gly Tyr Met Thr Tyr Val His Phe
    50                  55                  60

Gln Ser Thr Asn Arg Val Ala Leu Thr Leu Gly Ala Val Val Ala Leu
65                  70                  75                  80

Leu Trp Gly Val Tyr Ser Phe Thr Glu Ser Trp Lys Phe Val Thr Ser
                85                  90                  95

Arg Cys Arg Leu Cys Leu Gly Arg Arg Tyr Ile Leu Ala Pro Ala His
            100                 105                 110

His Val Glu Ser Ala Ala Gly Leu His Ser Ile Pro Ala Ser Gly Asn
        115                 120                 125

Arg Ala Tyr Ala Val Arg Lys Pro Gly Leu Thr Ser Val Asn Gly Thr
    130                 135                 140

Leu Val Pro Gly Leu Arg Ser Leu Val Leu Gly Gly Lys Arg Ala Val
145                 150                 155                 160

Lys Arg Gly Val Val Asn Leu Val Lys Tyr Gly Arg
                165                 170

<210> SEQ ID NO 32
<211> LENGTH: 174
<212> TYPE: PRT
<213> ORGANISM: porcine reproductive and respiratory syndrome virus

<400> SEQUENCE: 32

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Thr His
    50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Ser Trp Arg Phe Ile Thr
                85                  90                  95

```
Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
            115                 120                 125

Asp Asn His Ala Phe Val Val Arg Arg Pro Gly Ser Thr Thr Val Asn
        130                 135                 140

Gly Thr Leu Val Pro Gly Leu Lys Ser Leu Val Leu Gly Gly Lys Lys
145                 150                 155                 160

Ala Val Lys Gln Gly Val Val Asn Leu Val Lys Tyr Ala Lys
                165                 170

<210> SEQ ID NO 33
<211> LENGTH: 174
<212> TYPE: PRT
<213> ORGANISM: porcine reproductive and respiratory syndrome virus

<400> SEQUENCE: 33

Met Gly Ser Ser Leu Asp Asp Phe Cys Tyr Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Thr Phe Thr Phe Gly Tyr Met Thr Phe Val His
    50                  55                  60

Phe Asn Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
            115                 120                 125

Asp Asn His Ala Phe Val Val Arg Arg Pro Gly Ser Thr Thr Val Asn
        130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 34
<211> LENGTH: 174
<212> TYPE: PRT
<213> ORGANISM: porcine reproductive and respiratory syndrome virus

<400> SEQUENCE: 34

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Val His
    50                  55                  60

Phe Gln Ser Thr Asn Arg Val Ala Leu Thr Met Gly Ala Val Val Ala
65                  70                  75                  80
```

```
Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Thr Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 35
<211> LENGTH: 174
<212> TYPE: PRT
<213> ORGANISM: porcine reproductive and respiratory syndrome virus

<400> SEQUENCE: 35

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Val Phe Thr Phe Gly Tyr Met Thr Phe Val His
    50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 36
<211> LENGTH: 174
<212> TYPE: PRT
<213> ORGANISM: porcine reproductive and respiratory syndrome virus

<400> SEQUENCE: 36

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Val His
    50                  55                  60
```

```
Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170
```

<210> SEQ ID NO 37
<211> LENGTH: 174
<212> TYPE: PRT
<213> ORGANISM: porcine reproductive and respiratory syndrome virus

<400> SEQUENCE: 37

```
Met Gly Ser Ser Leu Asp Asp Phe Cys His Asp Ser Thr Ala Pro Gln
  1               5                  10                  15

Lys Val Leu Leu Ala Phe Ser Ile Thr Tyr Thr Pro Val Met Ile Tyr
                 20                  25                  30

Ala Leu Lys Val Ser Arg Gly Arg Leu Leu Gly Leu Leu His Leu Leu
             35                  40                  45

Ile Phe Leu Asn Cys Ala Phe Thr Phe Gly Tyr Met Thr Phe Ala His
 50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
            100                 105                 110

Ala His His Val Glu Ser Ala Ala Gly Phe His Pro Ile Ala Ala Asn
        115                 120                 125

Asp Asn His Ala Phe Val Val Arg Arg Pro Gly Ser Thr Thr Val Asn
    130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170
```

<210> SEQ ID NO 38
<211> LENGTH: 174
<212> TYPE: PRT
<213> ORGANISM: porcine reproductive and respiratory syndrome virus

<400> SEQUENCE: 38

```
Met Gly Ser Ser Leu Asp Asp Phe Cys Tyr Asp Ser Thr Ala Pro Gln
  1               5                  10                  15

Lys Val Leu Leu Ala Phe Ser Ile Thr Tyr Thr Pro Val Met Ile Tyr
                 20                  25                  30

Ala Leu Lys Val Ser Arg Gly Arg Leu Leu Gly Leu Leu His Leu Leu
             35                  40                  45
```

Ile Phe Leu Asn Cys Thr Phe Thr Phe Gly Tyr Met Thr Phe Val His
 50                  55                  60

Phe Asn Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
                100                 105                 110

Ala His His Val Glu Ser Ala Ala Gly Phe His Pro Ile Ala Ala Asn
             115                 120                 125

Asp Asn His Ala Phe Val Val Arg Arg Pro Gly Ser Thr Thr Val Asn
130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 39
<211> LENGTH: 173
<212> TYPE: PRT
<213> ORGANISM: porcine reproductive and respiratory syndrome virus

<400> SEQUENCE: 39

Met Gly Gly Leu Asp Asp Phe Cys Asn Asp Pro Thr Ala Ala Gln Lys
 1               5                  10                  15

Leu Val Leu Ala Phe Ser Ile Thr Tyr Thr Pro Ile Met Ile Tyr Ala
                20                  25                  30

Leu Lys Val Ser Arg Gly Arg Leu Leu Gly Leu Leu His Ile Leu Ile
                35                  40                  45

Phe Leu Asn Cys Ser Phe Thr Phe Gly Tyr Met Thr Tyr Val His Phe
 50                  55                  60

Gln Ser Ala Asn Arg Val Ala Leu Thr Leu Gly Ala Val Val Ala Leu
 65                  70                  75                  80

Leu Trp Gly Val Tyr Ser Leu Thr Glu Ser Trp Lys Phe Ile Thr Ser
                 85                  90                  95

Arg Cys Arg Leu Cys Cys Leu Gly Arg Arg Tyr Ile Leu Ala Pro Ala
                100                 105                 110

His His Val Glu Ser Ala Ala Gly Leu His Ser Ile Ser Ala Ser Gly
             115                 120                 125

Asn Arg Ala Tyr Ala Val Arg Lys Pro Gly Leu Thr Ser Val Asn Gly
130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170

<210> SEQ ID NO 40
<211> LENGTH: 174
<212> TYPE: PRT
<213> ORGANISM: porcine reproductive and respiratory syndrome virus

<400> SEQUENCE: 40

Met Gly Ser Ser Leu Asp Asp Phe Cys His Asp Ser Thr Ala Pro Glu
 1               5                  10                  15

Lys Val Leu Leu Ala Phe Ser Ile Thr Tyr Thr Pro Val Met Ile Tyr
                20                  25                  30

```
Ala Leu Lys Val Ser Arg Gly Arg Leu Leu Gly Leu Leu His Leu Leu
            35                  40                  45

Ile Phe Leu Asn Cys Ala Phe Thr Phe Gly Tyr Met Thr Phe Ala His
 50                  55                  60

Phe Gln Ser Thr Asn Lys Val Ala Leu Thr Met Gly Ala Val Val Ala
 65                  70                  75                  80

Leu Leu Trp Gly Val Tyr Ser Ala Ile Glu Thr Trp Lys Phe Ile Thr
                 85                  90                  95

Ser Arg Cys Arg Leu Cys Leu Leu Gly Arg Lys Tyr Ile Leu Ala Pro
                100                 105                 110

Ala His His Val Glu Ser Ala Ala Gly Phe His Pro Ile Ala Ala Asn
            115                 120                 125

Asp Asn His Ala Phe Val Val Arg Arg Pro Gly Ser Thr Thr Val Asn
130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 41
<211> LENGTH: 173
<212> TYPE: PRT
<213> ORGANISM: porcine reproductive and respiratory syndrome virus

<400> SEQUENCE: 41

Met Gly Gly Leu Asp Asp Phe Cys Asn Asp Pro Ile Ala Ala Gln Lys
1               5                  10                  15

Leu Val Leu Ala Phe Ser Ile Thr Tyr Thr Pro Ile Met Ile Tyr Ala
             20                  25                  30

Leu Lys Val Ser Arg Gly Arg Leu Leu Gly Leu Leu His Ile Leu Ile
            35                  40                  45

Phe Leu Asn Cys Ser Phe Thr Phe Gly Tyr Met Thr Tyr Val His Phe
 50                  55                  60

Gln Ser Thr Asn Arg Val Ala Leu Thr Leu Gly Ala Val Val Ala Leu
 65                  70                  75                  80

Leu Trp Gly Val Tyr Ser Phe Thr Glu Ser Trp Lys Phe Ile Thr Ser
                 85                  90                  95

Arg Cys Arg Leu Cys Cys Leu Gly Arg Arg Tyr Ile Leu Ala Pro Ala
                100                 105                 110

His His Val Glu Ser Ala Ala Gly Leu His Ser Ile Ser Ala Ser Gly
            115                 120                 125

Asn Arg Ala Tyr Ala Val Arg Lys Pro Gly Leu Thr Ser Val Asn Gly
130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170

<210> SEQ ID NO 42
<211> LENGTH: 174
<212> TYPE: PRT
<213> ORGANISM: porcine reproductive and respiratory syndrome virus

<400> SEQUENCE: 42

Met Gly Ser Ser Leu Asp Asp Phe Cys His Asp Ser Thr Ala Pro Gln
1               5                  10                  15
```

```
Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Ala His
50                  55                  60

Phe Gln Ser Thr Asn Arg Val Ala Leu Thr Met Gly Ala Val Val Ala
65                  70                  75                  80

Leu Leu Trp Gly Val Tyr Ser Ala Ile Glu Thr Trp Arg Phe Ile Thr
                85                  90                  95

Ser Arg Cys Arg Leu Cys Leu Leu Gly Arg Arg Tyr Ile Leu Ala Pro
                100                 105                 110

Ala His His Val Glu Ser Ala Ala Gly Phe His Pro Ile Thr Ala Asn
            115                 120                 125

Asp Asn His Ala Phe Val Val Arg Arg Pro Gly Ser Thr Thr Val Asn
        130                 135                 140

Gly Thr Leu Val Pro Gly Leu Lys Ser Leu Val Leu Gly Gly Arg Lys
145                 150                 155                 160

Ala Val Lys Arg Gly Val Val Asn Leu Val Lys Tyr Ala Lys
                165                 170

<210> SEQ ID NO 43
<211> LENGTH: 174
<212> TYPE: PRT
<213> ORGANISM: porcine reproductive and respiratory syndrome virus

<400> SEQUENCE: 43

Met Val Ser Ser Leu Asp Asp Phe Cys Asn Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Ala His
50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr
                85                  90                  95

Ser Arg Cys Arg Leu Cys Leu Leu Gly Arg Lys Tyr Ile Leu Ala Pro
                100                 105                 110

Ala His His Val Glu Ser Ala Ala Gly Phe His Pro Ile Ala Ala Ser
            115                 120                 125

Asp Asn His Ala Phe Val Val Arg Arg Pro Gly Ser Thr Thr Val Asn
        130                 135                 140

Gly Thr Leu Val Pro Gly Leu Lys Ser Leu Val Leu Gly Gly Arg Lys
145                 150                 155                 160

Ala Val Lys Arg Gly Val Val Asn Leu Val Lys Tyr Ala Lys
                165                 170

<210> SEQ ID NO 44
<211> LENGTH: 106
<212> TYPE: PRT
<213> ORGANISM: porcine reproductive and respiratory syndrome virus

<400> SEQUENCE: 44
```

```
Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr
            100                 105

<210> SEQ ID NO 45
<211> LENGTH: 106
<212> TYPE: PRT
<213> ORGANISM: porcine reproductive and respiratory syndrome virus

<400> SEQUENCE: 45

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr
            100                 105

<210> SEQ ID NO 46
<211> LENGTH: 106
<212> TYPE: PRT
<213> ORGANISM: porcine reproductive and respiratory syndrome virus

<400> SEQUENCE: 46

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr
            100                 105
```

```
<210> SEQ ID NO 47
<211> LENGTH: 106
<212> TYPE: PRT
<213> ORGANISM: porcine reproductive and respiratory syndrome virus

<400> SEQUENCE: 47

Met Leu Glu Lys Cys Leu Thr Ala Gly Cys Cys Ser Gln Leu Leu Ser
1               5                   10                  15

Leu Trp Cys Ile Val Pro Phe Cys Phe Ala Ala Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr
            100                 105

<210> SEQ ID NO 48
<211> LENGTH: 106
<212> TYPE: PRT
<213> ORGANISM: porcine reproductive and respiratory syndrome virus

<400> SEQUENCE: 48

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Val Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr
            100                 105

<210> SEQ ID NO 49
<211> LENGTH: 106
<212> TYPE: PRT
<213> ORGANISM: porcine reproductive and respiratory syndrome virus

<400> SEQUENCE: 49

Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60
```

```
Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr
            100                 105

<210> SEQ ID NO 50
<211> LENGTH: 106
<212> TYPE: PRT
<213> ORGANISM: porcine reproductive and respiratory syndrome virus

<400> SEQUENCE: 50

Met Leu Glu Lys Cys Leu Thr Ala Gly Cys Cys Ser Gln Leu Leu Ser
 1               5                  10                  15

Leu Trp Cys Ile Val Pro Phe Cys Phe Ala Val Leu Ala Asn Ala Ser
                 20                  25                  30

Asn Asp Ser Ser Ser His Leu Gln Leu Ile Tyr Asn Leu Thr Leu Cys
             35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr
            100                 105

<210> SEQ ID NO 51
<211> LENGTH: 106
<212> TYPE: PRT
<213> ORGANISM: porcine reproductive and respiratory syndrome virus

<400> SEQUENCE: 51

Met Leu Glu Lys Cys Leu Thr Ala Gly Cys Cys Ser Arg Leu Leu Ser
 1               5                  10                  15

Leu Trp Cys Ile Val Pro Phe Cys Phe Ala Val Leu Ala Asn Ala Ser
                 20                  25                  30

Asn Ser Ser Ser His Leu Gln Leu Ile Tyr Asn Leu Thr Leu Cys
             35                  40                  45

Glu Leu Asn Gly Thr Asp Trp Leu Ala Asn Arg Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr
            100                 105

<210> SEQ ID NO 52
<211> LENGTH: 106
<212> TYPE: PRT
<213> ORGANISM: porcine reproductive and respiratory syndrome virus

<400> SEQUENCE: 52

Met Leu Gly Lys Cys Leu Thr Ala Gly Cys Cys Ser Arg Leu Leu Ser
 1               5                  10                  15

Leu Trp Cys Ile Val Pro Phe Trp Phe Ala Val Leu Val Asn Ala Ser
```

```
                20                  25                  30
Ser Asn Ser Ser Ser His Phe Gln Leu Ile Tyr Asn Leu Thr Leu Cys
            35                  40                  45

Glu Leu Asn Gly Thr Asp Trp Leu Ala Asn Lys Phe Asp Trp Ala Val
        50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Phe His Gly Arg Tyr
            100                 105

<210> SEQ ID NO 53
<211> LENGTH: 79
<212> TYPE: PRT
<213> ORGANISM: porcine reproductive and respiratory syndrome virus

<400> SEQUENCE: 53

Met Leu Gly Lys Cys Leu Thr Ala Gly Tyr Cys Ser Gln Leu Pro Phe
 1               5                  10                  15

Leu Trp Cys Ile Val Pro Phe Cys Leu Ala Ala Leu Val Asn Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp His Phe Ser Trp Ala Val
    50                  55                  60

Glu Thr Phe Val Ile Phe Pro Val Leu Thr His Ile Val Ser Tyr
 65                  70                  75

<210> SEQ ID NO 54
<211> LENGTH: 60
<212> TYPE: PRT
<213> ORGANISM: porcine reproductive and respiratory syndrome virus

<400> SEQUENCE: 54

Met Leu Gly Lys Cys Leu Thr Ala Gly Cys Cys Ser Arg Leu Leu Ser
 1               5                  10                  15

Phe Trp Cys Ile Val Pro Phe Cys Phe Ala Val Leu Val Asn Ala Ser
            20                  25                  30

Tyr Ser Ser Ser His Leu Gln Leu Ile Tyr Asn Leu Thr Leu Cys
        35                  40                  45

Glu Leu Asn Gly Thr Asp Trp Leu Ala Asn Lys Phe
    50                  55                  60

<210> SEQ ID NO 55
<211> LENGTH: 106
<212> TYPE: PRT
<213> ORGANISM: porcine reproductive and respiratory syndrome virus

<400> SEQUENCE: 55

Met Leu Gly Lys Cys Leu Thr Ala Gly Cys Cys Ser Gln Leu Pro Phe
 1               5                  10                  15

Leu Trp Cys Ile Val Pro Phe Cys Phe Ala Ala Leu Val Asn Ala Ser
            20                  25                  30

Ser Ser Ser Ser Ser Gln Leu Gln Ser Ile Tyr Asn Leu Thr Ile Cys
        35                  40                  45

Glu Leu Asn Gly Thr Asp Trp Leu Asn Lys Asn Phe Asp Trp Ala Val
    50                  55                  60
```

-continued

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
                85                  90                  95

Ser Thr Ala Gly Tyr Tyr His Gly Arg Tyr
            100                 105

<210> SEQ ID NO 56
<211> LENGTH: 106
<212> TYPE: PRT
<213> ORGANISM: porcine reproductive and respiratory syndrome virus

<400> SEQUENCE: 56

Met Leu Gly Lys Cys Leu Thr Ala Gly Cys Cys Leu Arg Leu Pro Ser
1               5                   10                  15

Leu Trp Cys Ile Val Pro Phe Cys Phe Ala Val Leu Val Asn Ala Asn
                20                  25                  30

Asn Ser Ser Ser His Phe Gln Ser Ile Tyr Asn Leu Thr Leu Cys
            35                  40                  45

Glu Leu Asn Gly Thr Asp Trp Leu Ser Gly Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Leu Arg Glu Arg Tyr
            100                 105

<210> SEQ ID NO 57
<211> LENGTH: 106
<212> TYPE: PRT
<213> ORGANISM: porcine reproductive and respiratory syndrome virus
<220> FEATURE:
<221> NAME/KEY: misc_feature
<222> LOCATION: (98)..(98)
<223> OTHER INFORMATION: Xaa can be any naturally occurring amino acid

<400> SEQUENCE: 57

Met Leu Gly Lys Cys Leu Thr Ala Gly Cys Cys Leu Arg Leu Pro Ser
1               5                   10                  15

Leu Trp Cys Ile Val Pro Phe Cys Phe Ala Val Leu Val Asn Ala Asn
                20                  25                  30

Asn Ser Ser Ser His Phe Gln Ser Ile Tyr Asn Leu Thr Leu Cys
            35                  40                  45

Glu Leu Asn Gly Thr Asp Trp Leu Ser Gly Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Xaa Thr Gly Phe Leu Arg Glu Arg Tyr
            100                 105

<210> SEQ ID NO 58
<211> LENGTH: 80
<212> TYPE: PRT
<213> ORGANISM: porcine reproductive and respiratory syndrome virus

<400> SEQUENCE: 58

```
Met Leu Gly Lys Cys Leu Thr Ala Gly Tyr Cys Ser Arg Leu Leu Ser
1               5                   10                  15

Ser Trp Cys Ile Val Pro Phe Cys Phe Ala Val Leu Val Ser Ala Asn
            20                  25                  30

Asn Ser Ser Ser Tyr Ser Gln Leu Ile Tyr Asn Leu Thr Ile Cys
            35                  40                  45

Glu Leu Asn Gly Thr Asp Trp Leu Asn Asn Lys Phe Asp Trp Ala Val
        50                  55                  60

Glu Thr Phe Val Ile Phe Pro Val Leu Thr His Ile Val Ser Tyr Gly
65                  70                  75                  80
```

<210> SEQ ID NO 59
<211> LENGTH: 106
<212> TYPE: PRT
<213> ORGANISM: porcine reproductive and respiratory syndrome virus

<400> SEQUENCE: 59

```
Met Leu Gly Lys Cys Leu Thr Ala Gly Cys Cys Ser Arg Leu Leu Ser
1               5                   10                  15

Leu Trp Cys Ile Val Pro Phe Cys Phe Ala Val Leu Gly Ser Ala Asn
            20                  25                  30

Ser Ser Ser Ser His Phe Gln Leu Ile Tyr Asn Leu Thr Leu Cys
            35                  40                  45

Glu Leu Asn Gly Thr Asp Trp Leu Ala Glu Lys Phe Asp Trp Ala Val
        50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr
                100                 105
```

<210> SEQ ID NO 60
<211> LENGTH: 80
<212> TYPE: PRT
<213> ORGANISM: porcine reproductive and respiratory syndrome virus

<400> SEQUENCE: 60

```
Met Leu Gly Arg Cys Leu Thr Ala Gly Tyr Cys Ser Arg Leu Leu Ser
1               5                   10                  15

Leu Trp Cys Ile Val Pro Phe Trp Phe Ala Val Leu Val Asn Ala Asn
            20                  25                  30

Ser Ser Ser Ser His Phe Gln Leu Ile Tyr Asn Leu Thr Leu Cys
            35                  40                  45

Glu Leu Asn Gly Thr Glu Trp Leu Ala Asn Lys Phe Asp Trp Ala Val
        50                  55                  60

Glu Thr Phe Val Ile Phe Pro Val Leu Thr His Ile Val Ser Tyr Gly
65                  70                  75                  80
```

<210> SEQ ID NO 61
<211> LENGTH: 106
<212> TYPE: PRT
<213> ORGANISM: porcine reproductive and respiratory syndrome virus

<400> SEQUENCE: 61

```
Met Leu Val Lys Cys Leu Thr Ala Gly Cys Cys Ser Gln Leu Leu Phe
1               5                   10                  15
```

```
Leu Trp Cys Ile Val Ser Ser Cys Phe Val Ala Leu Val Ser Ala Asn
                20                  25                  30

Thr Thr Ser Ser Ser Asn Leu Gln Leu Ile Tyr Asn Leu Thr Leu Cys
            35                  40                  45

Glu Leu Asn Gly Thr Asp Trp Leu Ala Asn Lys Phe Asp Trp Ala Val
 50                  55                  60

Glu Cys Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Val His Gly Arg Tyr
            100                 105

<210> SEQ ID NO 62
<211> LENGTH: 106
<212> TYPE: PRT
<213> ORGANISM: porcine reproductive and respiratory syndrome virus

<400> SEQUENCE: 62

Met Leu Gly Lys Cys Leu Thr Ala Gly Tyr Cys Ser Gln Leu Pro Phe
 1               5                   10                  15

Leu Trp Cys Ile Val Pro Phe Cys Leu Ala Ala Leu Val Asn Ala Asn
                20                  25                  30

Ser Asn Ser Ser Ser His Leu Gln Leu Ile Tyr Asn Leu Thr Ile Cys
            35                  40                  45

Glu Leu Asn Gly Thr Asp Trp Leu Asn Asn His Phe Ser Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Ile Thr Val
                85                  90                  95

Ser Thr Ala Gly Tyr Tyr His Glu Arg Tyr
            100                 105

<210> SEQ ID NO 63
<211> LENGTH: 106
<212> TYPE: PRT
<213> ORGANISM: porcine reproductive and respiratory syndrome virus

<400> SEQUENCE: 63

Met Leu Gly Lys Cys Leu Thr Ala Gly Cys Cys Ser Arg Leu Leu Ser
 1               5                   10                  15

Leu Trp Cys Ile Val Pro Phe Cys Phe Thr Val Leu Val Asp Ala Asn
                20                  25                  30

Gly Asn Ser Ser Ser His Leu Gln Leu Ile Tyr Asn Leu Thr Leu Cys
            35                  40                  45

Glu Leu Asn Gly Thr Asp Trp Leu Ala Asn Arg Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Ile Ala Leu Val Thr Val
                85                  90                  95

Ser Thr Ala Gly Phe Leu His Gly Arg Tyr
            100                 105

<210> SEQ ID NO 64
<211> LENGTH: 106
```

```
<212> TYPE: PRT
<213> ORGANISM: porcine reproductive and respiratory syndrome virus

<400> SEQUENCE: 64

Met Leu Gly Lys Cys Leu Thr Ala Gly Tyr Cys Ser Arg Leu Leu Phe
1               5                   10                  15

Phe Trp Cys Ile Val Pro Phe Cys Phe Ala Val Leu Val Asn Ala Asn
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
        50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Phe His Gly Arg Tyr
            100                 105

<210> SEQ ID NO 65
<211> LENGTH: 106
<212> TYPE: PRT
<213> ORGANISM: porcine reproductive and respiratory syndrome virus

<400> SEQUENCE: 65

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Val
        50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr
            100                 105

<210> SEQ ID NO 66
<211> LENGTH: 106
<212> TYPE: PRT
<213> ORGANISM: porcine reproductive and respiratory syndrome virus

<400> SEQUENCE: 66

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Leu
        50                  55                  60

Glu Thr Phe Val Ile Phe Pro Val Leu Thr His Ile Val Ser Tyr Ser
65                  70                  75                  80

Ala Leu Thr Thr Ser His Phe Leu Asp Thr Val Gly Leu Val Thr Val
```

```
                    85                  90                  95

Ser Thr Ala Gly Phe Tyr His Gly Arg Tyr
            100                 105

<210> SEQ ID NO 67
<211> LENGTH: 106
<212> TYPE: PRT
<213> ORGANISM: porcine reproductive and respiratory syndrome virus

<400> SEQUENCE: 67

Met Leu Gly Lys Cys Leu Thr Ala Gly Cys Cys Ser Gln Leu Leu Phe
1               5                   10                  15

Leu Trp Cys Ile Val Pro Ser Cys Phe Val Ala Leu Val Ser Ala Asn
            20                  25                  30

Ser Asn Ser Ser Ser Asn Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Cys Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Phe His Gly Arg Tyr
            100                 105

<210> SEQ ID NO 68
<211> LENGTH: 106
<212> TYPE: PRT
<213> ORGANISM: porcine reproductive and respiratory syndrome virus

<400> SEQUENCE: 68

Met Leu Gly Lys Cys Leu Thr Ala Gly Cys Cys Ser Gln Leu Leu Phe
1               5                   10                  15

Leu Trp Cys Ile Val Pro Ser Cys Phe Val Ala Leu Val Ser Ala Asn
            20                  25                  30

Ser Asn Ser Ser Ser Asn Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Cys Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Phe His Gly Arg Tyr
            100                 105

<210> SEQ ID NO 69
<211> LENGTH: 106
<212> TYPE: PRT
<213> ORGANISM: porcine reproductive and respiratory syndrome virus

<400> SEQUENCE: 69

Met Leu Gly Lys Cys Leu Thr Ala Gly Cys Cys Ser Gln Leu Leu Phe
1               5                   10                  15

Leu Trp Cys Ile Val Pro Ser Cys Phe Val Ala Leu Val Ser Ala Asn
            20                  25                  30

Ser Asn Ser Ser Ser Asn Leu Gln Leu Ile Tyr Asn Leu Thr Leu Cys
        35                  40                  45
```

```
Glu Leu Asn Gly Thr Asp Trp Leu Ala Asn Lys Phe Asp Trp Ala Val
    50                  55                  60

Glu Cys Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Phe His Gly Arg Tyr
            100                 105

<210> SEQ ID NO 70
<211> LENGTH: 80
<212> TYPE: PRT
<213> ORGANISM: porcine reproductive and respiratory syndrome virus

<400> SEQUENCE: 70

Met Leu Gly Arg Cys Leu Thr Ala Gly Cys Cys Ser Arg Leu Leu Ser
 1               5                  10                  15

Leu Trp Cys Ile Val Pro Phe Cys Phe Ala Ala Leu Val Asn Ala Asn
                 20                  25                  30

Ser Asn Ser Ser Ser His Leu Gln Leu Ile Tyr Asn Leu Thr Leu Cys
             35                  40                  45

Glu Leu Asn Gly Thr Asp Trp Leu Lys Asp Lys Phe Asp Trp Ala Val
    50                  55                  60

Glu Thr Phe Val Ile Phe Pro Val Leu Thr His Ile Val Ser Tyr Gly
 65                  70                  75                  80

<210> SEQ ID NO 71
<211> LENGTH: 106
<212> TYPE: PRT
<213> ORGANISM: porcine reproductive and respiratory syndrome virus

<400> SEQUENCE: 71

Met Leu Gly Arg Cys Leu Thr Ala Gly Cys Cys Ser Arg Leu Leu Ser
 1               5                  10                  15

Ser Trp Cys Ile Val Pro Phe Trp Phe Ala Val Leu Val Asp Ala Asn
                 20                  25                  30

Ser Asn Ser Ser Ser His Phe Gln Leu Ile Tyr Asn Leu Thr Leu Cys
             35                  40                  45

Glu Leu Asn Gly Thr Asp Trp Leu Asn Arg Lys Phe Asp Trp Ala Val
    50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr
            100                 105

<210> SEQ ID NO 72
<211> LENGTH: 106
<212> TYPE: PRT
<213> ORGANISM: porcine reproductive and respiratory syndrome virus

<400> SEQUENCE: 72

Met Leu Gly Lys Cys Leu Thr Ala Gly Cys Cys Ser Arg Leu Pro Ser
 1               5                  10                  15

Leu Trp Cys Ile Val Pro Phe Cys Phe Ala Val Leu Ala Ser Ala Ser
                 20                  25                  30
```

```
Ser Asp Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr
            100                 105
```

<210> SEQ ID NO 73
<211> LENGTH: 70
<212> TYPE: PRT
<213> ORGANISM: porcine reproductive and respiratory syndrome virus

<400> SEQUENCE: 73

```
Met Leu Gly Lys Cys Leu Thr Ala Gly Cys Cys Ser Gln Leu Leu Phe
 1               5                  10                  15

Leu Trp Cys Ile Val Pro Ser Cys Phe Val Ala Leu Val Ser Ala Asn
            20                  25                  30

Gly Asn Ser Gly Ser Asn Leu Gln Leu Ile Tyr Asn Leu Thr Leu Cys
            35                  40                  45

Glu Leu Asn Gly Thr Asp Trp Leu Ala Asn Lys Phe Asp Trp Ala Val
 50                  55                  60

Glu Cys Phe Val Ile Phe
 65                  70
```

<210> SEQ ID NO 74
<211> LENGTH: 100
<212> TYPE: PRT
<213> ORGANISM: porcine reproductive and respiratory syndrome virus

<400> SEQUENCE: 74

```
Met Leu Gly Lys Cys Leu Thr Ala Gly Tyr Cys Ser Ser Leu Leu Phe
 1               5                  10                  15

Phe Trp Cys Ile Val Pro Ser Trp Phe Val Ala Leu Ala Ser Ala Asn
            20                  25                  30

Ser Ile Asn Ser Pro His Leu Gln Leu Ile Tyr Asn Leu Thr Leu Cys
            35                  40                  45

Glu Leu Asn Gly Thr Asp Trp Leu Ala Gly Glu Phe Asp Trp Ala Val
 50                  55                  60

Glu Cys Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly
            100
```

<210> SEQ ID NO 75
<211> LENGTH: 79
<212> TYPE: PRT
<213> ORGANISM: porcine reproductive and respiratory syndrome virus

<400> SEQUENCE: 75

```
Met Leu Gly Arg Cys Leu Thr Ala Gly Cys Cys Ser Gln Leu Pro Phe
 1               5                  10                  15

Leu Trp Cys Ile Val Pro Phe Cys Leu Val Ala Leu Val Asn Ala Asn
```

```
                    20                  25                  30

Ser Asn Ser Gly Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Val
        50                  55                  60

Glu Thr Phe Val Ile Phe Pro Val Leu Thr His Ile Val Ser Tyr
65                  70                  75

<210> SEQ ID NO 76
<211> LENGTH: 100
<212> TYPE: PRT
<213> ORGANISM: porcine reproductive and respiratory syndrome virus

<400> SEQUENCE: 76

Met Leu Gly Lys Cys Leu Thr Ala Gly Cys Cys Ser Arg Leu Leu Ser
1               5                   10                  15

Leu Trp Cys Ile Val Pro Ser Trp Phe Ala Val Leu Val Asn Ala Asn
            20                  25                  30

Ser Ala Ser Ser Ser His Leu Gln Leu Ile Tyr Asn Leu Thr Leu Cys
        35                  40                  45

Glu Leu Asn Gly Thr Asp Trp Leu Ala Asp Lys Phe Asp Trp Ala Val
    50                  55                  60

Glu Thr Phe Val Leu Tyr Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly
        100

<210> SEQ ID NO 77
<211> LENGTH: 60
<212> TYPE: PRT
<213> ORGANISM: porcine reproductive and respiratory syndrome virus

<400> SEQUENCE: 77

Met Leu Gly Arg Cys Leu Thr Ala Cys Tyr Cys Leu Arg Leu Leu Ser
1               5                   10                  15

Leu Trp Cys Ile Val Pro Phe Trp Phe Ala Val Leu Val Ser Ala Asn
            20                  25                  30

Ser Asn Ser Ser Ser His Leu Gln Ser Ile Tyr Lys Leu Thr Leu Cys
        35                  40                  45

Glu Leu Asn Gly Thr Glu Trp Leu Asn Glu Arg Phe
    50                  55                  60

<210> SEQ ID NO 78
<211> LENGTH: 66
<212> TYPE: PRT
<213> ORGANISM: porcine reproductive and respiratory syndrome virus

<400> SEQUENCE: 78

Met Leu Gly Arg Cys Leu Thr Ala Gly Tyr Cys Ser Gln Leu Pro Ser
1               5                   10                  15

Leu Trp Cys Ile Val Pro Phe Trp Phe Ala Val Leu Val Ser Ala Asn
            20                  25                  30

Ser Thr Ser Ser Ser Tyr Ser Gln Leu Ile Tyr Asn Leu Thr Ile Cys
        35                  40                  45

Glu Leu Asn Gly Pro Asp Trp Leu Asn Glu Lys Phe Phe Ser His Gly
    50                  55                  60
```

Arg Tyr
65

<210> SEQ ID NO 79
<211> LENGTH: 80
<212> TYPE: PRT
<213> ORGANISM: porcine reproductive and resp
<210> SEQ ID NO 82
<211> LENGTH: 102
<212> TYPE: PRT
<213> ORGANISM: porcine reproductive and respiratory syndrome virus

<400> SEQUENCE: 82

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Val
            20                  25                  30

Ala Gly Gly Ser Ser Ser Thr Tyr Gln Tyr Ile Tyr Asn Leu Thr Ile
        35                  40                  45

Cys Glu Leu Asn Gly Thr Asp Trp Leu Ser Asn His Phe Asp Trp Ala
    50                  55                  60

Val Glu Thr Phe Val Leu Tyr Pro Val Ala Thr His Ile Leu Ser Leu
65                  70                  75                  80

Gly Phe Leu Thr Thr Ser His Phe Phe Asp Ala Leu Gly Leu Gly Ala
                85                  90                  95

Val Ser Thr Ile Gly Phe
            100

<210> SEQ ID NO 83
<211> LENGTH: 106
<212> TYPE: PRT
<213> ORGANISM: porcine reproductive and respiratory syndrome virus

<400> SEQUENCE: 83

Met Arg Cys Ser Tyr Lys Leu Gly Arg Ser Leu Ile Leu His Ser Cys
1               5                   10                  15

Ser Trp Trp Phe Phe Leu Leu Cys Thr Gly Leu Ser Trp Ser Phe Ala
            20                  25                  30

Asp Gly Asn Gly Asn Asn Ser Thr Tyr Gln Tyr Ile Tyr Asn Leu Thr
        35                  40                  45

Ile Cys Glu Leu Asn Gly Thr Asn Trp Leu Ser Gly His Phe Asp Trp
    50                  55                  60

Ala Val Glu Thr Phe Val Leu Tyr Pro Val Val Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Ile Asp Gly
            100                 105

<210> SEQ ID NO 84
<211> LENGTH: 73
<212> TYPE: PRT
<213> ORGANISM: porcine reproductive and respiratory syndrome virus

<400> SEQUENCE: 84

Asp Gly Asn Gly Asn Ser Ser Thr Tyr Gln Tyr Ile Tyr Asn Leu Thr
1               5                   10                  15

Ile Cys Glu Leu Asn Gly Thr Asp Trp Leu Ser Ser His Phe Gly Trp
            20                  25                  30

Ala Val Glu Thr Phe Val Phe Tyr Pro Val Ala Thr His Ile Leu Ser
        35                  40                  45

Leu Gly Phe Leu Thr Thr Ser His Phe Phe Asp Ala Leu Gly Leu Gly
    50                  55                  60

Ala Val Ser Thr Ala Gly Phe Val Gly

```
                        65                  70

<210> SEQ ID NO 85
<211> LENGTH: 74
<212> TYPE: PRT
<213> ORGANISM: porcine reproductive and respiratory syndrome virus

<400> SEQUENCE: 85

Asp Gly Asn Gly Asn Ser Ser Thr Tyr Gln Tyr Ile Tyr Asn Leu Thr
1               5                  10                  15

Ile Cys Glu Leu Asn Gly Thr Asp Trp Leu Ser Ser His Phe Gly Trp
            20                  25                  30

Ala Val Glu Thr Phe Val Leu Tyr Pro Val Ala Thr His Ile Leu Ser
        35                  40                  45

Leu Gly Phe Leu Thr Thr Ser His Phe Phe Asp Ala Leu Gly Leu Gly
    50                  55                  60

Ala Val Ser Thr Ala Gly Phe Val Gly Gly
65                  70

<210> SEQ ID NO 86
<211> LENGTH: 66
<212> TYPE: PRT
<213> ORGANISM: porcine reproductive and respiratory syndrome virus

<400> SEQUENCE: 86

Asp Gly Asn Gly Ser Ser Ser Thr Tyr Gln Tyr Ile Tyr Asn Leu Thr
1               5                  10                  15

Ile Cys Glu Leu Asn Gly Thr Asp Trp Leu Ser Ser His Phe Gly Trp
            20                  25                  30

Ala Val Glu Thr Phe Val Leu Tyr Pro Val Ala Thr His Ile Leu Ser
        35                  40                  45

Leu Gly Phe Leu Thr Thr Ser His Phe Phe Asp Ala Leu Gly Leu Gly
    50                  55                  60

Ala Val
65

<210> SEQ ID NO 87
<211> LENGTH: 74
<212> TYPE: PRT
<213> ORGANISM: porcine reproductive and respiratory syndrome virus

<400> SEQUENCE: 87

Asp Gly Asn Asp Ser Ser Ser Thr Tyr Gln Tyr Ile Tyr Asn Leu Thr
1               5                  10                  15

Ile Cys Glu Leu Asn Gly Thr Glu Ser Leu Ser Ser His Phe Asp Trp
            20                  25                  30

Ala Val Glu Thr Phe Val Leu Tyr Pro Val Ala Thr His Ile Leu Ser
        35                  40                  45

Leu Gly Phe Leu Thr Thr Ser His Phe Phe Asp Ala Leu Gly Leu Gly
    50                  55                  60

Ala Val Ser Thr Thr Gly Phe Val Gly Gly
65                  70

<210> SEQ ID NO 88
<211> LENGTH: 603
<212> TYPE: DNA
<213> ORGANISM: porcine reproductive and respiratory syndrome virus

<400> SEQUENCE: 88
```

```
atgttgggga aatgcttgac cgcgggctat tgctcgcaat tgcctttttt gtggtgtatc      60
gtgccgttct gtcttgctgc gctcgtcaac gccagcagca acagcagctc ccacttacag     120
ttgatttata acttaacgat atgtgagctg aatggcacag actggctgaa tgatcatttt     180
agttgggcag tggagacttt cgttatcttt cctgtgttga ctcacattgt ttcctacggc     240
gccctcacta ccagccactt ccttgacacg gtcggcctga tcactgtgtc caccgccgga     300
tactaccatg cgcggtatgt cttgagtagc atctatgccg tctgcgccct ggctgcgctg     360
atttgcttcg tcatcaggtt gacgaaaaat tgtatgtcct ggcgctactc catgtaccag     420
tataccaact tccttctgga caccaagggc agactctatc gctggcggtc acccgtcatc     480
atagagaaaa ggggtaaaat tgaggttgga ggtgacctga tcgacctcaa gagagttgtg     540
cttgatggct ccgcggcaac ccctgtaacc aaagtttcag cggaacaatg gggtcgtcct     600
tag                                                                   603
```

```
<210> SEQ ID NO 89
<211> LENGTH: 200
<212> TYPE: PRT
<213> ORGANISM: porcine reproductive and respiratory syndrome virus

<400> SEQUENCE: 89

Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Ser
            20                  25                  30

Ser Asn Ser Ser Ser His Leu Gln Leu Ile Tyr Asn Leu Thr Ile Cys
        35                  40                  45

Glu Leu Asn Gly Thr Asp Trp Leu Asn Asp His Phe Ser Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Ile Thr Val
                85                  90                  95

Ser Thr Ala Gly Tyr Tyr His Ala Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Ile Glu Val Gly Gly Asp Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Gly Arg Pro
        195                 200

<210> SEQ ID NO 90
<211> LENGTH: 603
<212> TYPE: DNA
<213> ORGANISM: porcine reproductive and respiratory syndrome virus

<400> SEQUENCE: 90
atgttgggga aatgcttgac cgcgggctat tgctcgcaat tgcctttttt gtggtgtatc      60
```

```
gtgccgttct gtcttgctgc gctcgtcaac gccaacaacg acagcagctc ccacttacag    120
ttgatttata gcttaacgat atgtgagctg aatggcacag aatggctgaa cgaacatttc    180
agttgggcag tggagacctt cgtcatcttt cctgcgttga ctcatattgt ttcctacggc    240
gccctcacta ccagccactt ccttgacacg gtcggcctga tcactgtgtc caccgccgga    300
tactaccata gcggtatgt cttgagtagc atctatgctg tctgcgccct ggctgcgctg    360
atttgcttcg tcatcaggtt gacgaaaaat tgtatgtcct ggcgctactc atgtaccaga    420
tataccaact ttcttctgga caccaagggc agactctatc gctggcggtc acccgtcatc    480
atagagaaaa agggtaagat tgaggttgga ggtgacctaa tcgacctcaa gagagttgtg    540
cttgatggtt ccgcggcaac ccctgtaacc aaagtttcag cggaacaatg gggtcgtcct    600
tag                                                                  603

<210> SEQ ID NO 91
<211> LENGTH: 200
<212> TYPE: PRT
<213> ORGANISM: porcine reproductive and respiratory syndrome virus

<400> SEQUENCE: 91

Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Asn
            20                  25                  30

Asn Asp Ser Ser Ser His Leu Gln Leu Ile Tyr Ser Leu Thr Ile Cys
        35                  40                  45

Glu Leu Asn Gly Thr Glu Trp Leu Asn Glu His Phe Ser Trp Ala Val
    50                  55                  60

Glu Thr Phe Val Ile Phe Pro Ala Leu Thr His Ile Val Ser Tyr Gly
65                  70                  75                  80

Ala Leu Thr Thr Ser His Phe Leu Asp Thr Val Gly Leu Ile Thr Val
                85                  90                  95

Ser Thr Ala Gly Tyr Tyr His Lys Arg Tyr Val Leu Ser Ser Ile Tyr
            100                 105                 110

Ala Val Cys Ala Leu Ala Ala Leu Ile Cys Phe Val Ile Arg Leu Thr
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Lys Gly Lys Ile Glu Val Gly Gly Asp Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Gly Arg Pro
        195                 200

<210> SEQ ID NO 92
<211> LENGTH: 9
<212> TYPE: PRT
<213> ORGANISM: porcine reproductive and respiratory syndrome virus

<400> SEQUENCE: 92

Ser His Leu Gln Leu Ile Tyr Asn Leu
1               5
```

```
<210> SEQ ID NO 93
<211> LENGTH: 60
<212> TYPE: PRT
<213> ORGANISM: porcine reproductive and respiratory syndrome virus

<400> SEQUENCE: 93

Met Leu Gly Arg Cys Leu Thr Ala Gly Cys Cys Ser Gln Leu Pro Phe
1               5                   10                  15

Leu Trp Cys Ile Val Pro Phe Cys Leu Val Ala Leu Val Asn Ala Asn
            20                  25                  30

Ser Asn Ser Gly Ser His Leu Gln Leu Ile Tyr Asn Leu Thr Leu Cys
        35                  40                  45

Glu Leu Asn Gly Thr Asp Trp Leu Lys Asp Lys Phe
    50                  55                  60

<210> SEQ ID NO 94
<211> LENGTH: 60
<212> TYPE: PRT
<213> ORGANISM: porcine reproductive and respiratory syndrome virus

<400> SEQUENCE: 94

Met Leu Gly Arg Cys Leu Thr Ala Cys Tyr Cys Leu Arg Leu Leu Ser
1               5                   10                  15

Leu Trp Cys Ile Val Pro Phe Trp Phe Ala Val Leu Val Ser Ala Asn
            20                  25                  30

Ser Asn Ser Ser Ser His Leu Gln Ser Ile Tyr Lys Leu Thr Leu Cys
        35                  40                  45

Glu Leu Asn Gly Thr Glu Trp Leu Asn Glu Arg Phe
    50                  55                  60

<210> SEQ ID NO 95
<211> LENGTH: 80
<212> TYPE: PRT
<213> ORGANISM: porcine reproductive and respiratory syndrome virus

<400> SEQUENCE: 95

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Lys Asp Lys Phe Asp Trp Ala Val
    50                  55                  60

Glu Thr Phe Val Ile Phe Pro Val Leu Thr His Ile Val Ser Tyr Gly
65                  70                  75                  80

<210> SEQ ID NO 96
<211> LENGTH: 80
<212> TYPE: PRT
<213> ORGANISM: porcine reproductive and respiratory syndrome virus

<400> SEQUENCE: 96

Met Leu Gly Arg Cys Leu Thr Ala Gly Cys Cys Ser Arg Leu Leu Ser
1               5                   10                  15

Leu Trp Cys Ile Val Pro Phe Cys Phe Val Ala Leu Val Asn Ala Asn
            20                  25                  30

Ser Asn Ser Gly Ser His Leu Gln Leu Ile Tyr Asn Leu Thr Leu Cys
        35                  40                  45
```

```
Glu Leu Asn Gly Thr Asp Trp Leu Lys Asp Lys Phe Asp Trp Ala Val
 50                  55                  60

Glu Thr Phe Val Ile Phe Pro Val Leu Thr His Ile Val Ser Tyr Ser
 65                  70                  75                  80

<210> SEQ ID NO 97
<211> LENGTH: 80
<212> TYPE: PRT
<213> ORGANISM: porcine reproductive and respiratory syndrome virus

<400> SEQUENCE: 97

Met Leu Gly Lys Cys Leu Thr Ala Gly Tyr Cys Ser Gln Leu Pro Phe
  1               5                  10                  15

Leu Trp Cys Ile Val Pro Phe Cys Leu Ala Ala Leu Val Asn Ala Asn
                 20                  25                  30

Asn Asp Ser Ser Ser His Leu Gln Leu Ile Tyr Ser Leu Thr Ile Cys
             35                  40                  45

Glu Leu Asn Gly Thr Glu Trp Leu Asn Glu His Phe Ser Trp Ala Val
 50                  55                  60

Glu Thr Phe Val Ile Phe Pro Ala Leu Thr His Ile Val Ser Tyr Gly
 65                  70                  75                  80

<210> SEQ ID NO 98
<211> LENGTH: 80
<212> TYPE: PRT
<213> ORGANISM: porcine reproductive and respiratory syndrome virus

<400> SEQUENCE: 98

Met Leu Glu Lys Cys Leu Thr Ala Gly Cys Cys Ser Arg Leu Leu Ser
  1               5                  10                  15

Leu Trp Cys Ile Val Pro Phe Cys Phe Ala Val Leu Ala Asn Ala Ser
                 20                  25                  30

Asn Asp Ser Ser Ser His Leu Gln Leu Ile Tyr Asn Leu Thr Leu Cys
             35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

<210> SEQ ID NO 99
<211> LENGTH: 80
<212> TYPE: PRT
<213> ORGANISM: porcine reproductive and respiratory syndrome virus

<400> SEQUENCE: 99

Met Leu Gly Arg Cys Leu Thr Ala Gly Cys Cys Ser Arg Leu Leu Ser
  1               5                  10                  15

Leu Trp Cys Ile Val Pro Phe Cys Phe Val Ala Leu Val Asn Ala Asn
                 20                  25                  30

Ser Asn Ser Gly Ser His Leu Gln Leu Ile Tyr Asn Leu Thr Leu Cys
             35                  40                  45

Glu Leu Asn Gly Thr Asp Trp Leu Lys Asp Lys Phe Asp Trp Ala Val
 50                  55                  60

Glu Thr Phe Val Ile Phe Pro Val Leu Thr His Ile Val Ser Tyr Ser
 65                  70                  75                  80

<210> SEQ ID NO 100
<211> LENGTH: 80
<212> TYPE: PRT
```

<213> ORGANISM: porcine reproductive and respiratory syndrome virus

<400> SEQUENCE: 100

Met Leu Gly Arg Cys Leu Thr Ala Gly Cys Cys Ser Arg Leu Leu Ser
1               5                   10                  15

Leu Trp Cys Ile Val Pro Phe Cys Phe Val Ala Leu Val Asn Ala Asn
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Val
        50                  55                  60

Glu Thr Phe Val Ile Phe Pro Val Leu Thr His Ile Val Ser Tyr Ser
65                  70                  75                  80

<210> SEQ ID NO 101
<211> LENGTH: 80
<212> TYPE: PRT
<213> ORGANISM: porcine reproductive and respiratory syndrome virus

<400> SEQUENCE: 101

Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Asn
                20                  25                  30

Asn Asp Ser Ser Ser His Leu Gln Leu Ile Tyr Asn Leu Thr Ile Cys
            35                  40                  45

Glu Leu Asn Gly Thr Glu Trp Leu Asn Glu His Phe Ser Trp Ala Val
        50                  55                  60

Glu Thr Phe Val Ile Phe Pro Ala Leu Thr His Ile Val Ser Tyr Gly
65                  70                  75                  80

<210> SEQ ID NO 102
<211> LENGTH: 80
<212> TYPE: PRT
<213> ORGANISM: porcine reproductive and respiratory syndrome virus

<400> SEQUENCE: 102

Met Leu Gly Arg Cys Leu Thr Ala Gly Cys Cys Ser Arg Leu Leu Ser
1               5                   10                  15

Leu Trp Cys Ile Val Pro Phe Cys Phe Val Ala Leu Val Asn Ala Asn
                20                  25                  30

Ser Asn Ser Gly Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Val
        50                  55                  60

Glu Thr Phe Val Ile Phe Pro Val Leu Thr His Ile Val Ser Tyr Ser
65                  70                  75                  80

<210> SEQ ID NO 103
<211> LENGTH: 80
<212> TYPE: PRT
<213> ORGANISM: porcine reproductive and respiratory syndrome virus

<400> SEQUENCE: 103

Met Leu Gly Arg Cys Leu Thr Ala Gly Cys Cys Ser Arg Leu Leu Ser
1               5                   10                  15

Leu Trp Cys Ile Val Pro Phe Cys Phe Val Ala Leu Val Asn Ala Asn
                20                  25                  30

-continued

```
Ser Asn Asn Gly Ser His Leu Gln Leu Ile Tyr Asn Leu Thr Leu Cys
            35                  40                  45

Glu Leu Asn Gly Thr Asp Trp Leu Lys Asp Lys Phe Asp Trp Ala Val
    50                  55                  60

Glu Thr Phe Val Ile Phe Pro Val Leu Thr His Ile Val Ser Tyr Ser
65                  70                  75                  80

<210> SEQ ID NO 104
<211> LENGTH: 80
<212> TYPE: PRT
<213> ORGANISM: porcine reproductive and respiratory syndrome virus

<400> SEQUENCE: 104

Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Asn
            20                  25                  30

Asn Asp Ser Ser Ser His Leu Gln Leu Ile Tyr Asn Leu Thr Ile Cys
            35                  40                  45

Glu Leu Asn Gly Thr Glu Trp Leu Asn Glu His Phe Ser Trp Ala Val
    50                  55                  60

Glu Thr Phe Val Ile Phe Pro Ala Leu Thr His Ile Val Ser Tyr Gly
65                  70                  75                  80

<210> SEQ ID NO 105
<211> LENGTH: 80
<212> TYPE: PRT
<213> ORGANISM: porcine reproductive and respiratory syndrome virus

<400> SEQUENCE: 105

Met Leu Gly Lys Cys Leu Thr Ala Gly Tyr Cys Ser Gln Leu Pro Phe
1               5                   10                  15

Leu Trp Cys Ile Val Pro Phe Cys Leu Ala Ala Leu Val Asn Ala Asn
            20                  25                  30

Asn Asp Ser Ser Ser His Leu Gln Leu Ile Tyr Asn Leu Thr Ile Cys
            35                  40                  45

Glu Leu Asn Gly Thr Glu Trp Leu Asn Glu His Phe Ser Trp Ala Val
    50                  55                  60

Glu Thr Phe Val Ile Phe Pro Ala Leu Thr His Ile Val Ser Tyr Gly
65                  70                  75                  80
```